(12) United States Patent
Nagashima et al.

(10) Patent No.: US 9,795,542 B2
(45) Date of Patent: Oct. 24, 2017

(54) PHOTOELECTRIC CONVERSION DEVICE

(75) Inventors: Tomonori Nagashima, Susono (JP);
Yasuhiko Takeda, Aichi-gun (JP);
Nicholas John Ekins-Daukes, Kent
(GB); Daniel James Farrell, London
(GB)

(73) Assignee: **TOYOTA JIDOSHA KABUSHIKI
KAISHA**, Toyota (JP)

( * ) Notice: Subject to any disclaimer, the term of this patent is extended or adjusted under 35 U.S.C. 154(b) by 709 days.

(21) Appl. No.: 14/127,442

(22) PCT Filed: Jul. 6, 2012

(86) PCT No.: PCT/IB2012/001411
§ 371 (c)(1),
(2), (4) Date: Mar. 26, 2014

(87) PCT Pub. No.: WO2013/005103
PCT Pub. Date: Jan. 10, 2013

(65) Prior Publication Data
US 2014/0224305 A1    Aug. 14, 2014

(30) Foreign Application Priority Data
Jul. 7, 2011    (JP) .................... 2011-150844

(51) Int. Cl.
*H01L 31/00*    (2006.01)
*A61K 8/02*    (2006.01)
(Continued)

(52) U.S. Cl.
CPC .......... *A61K 8/0283* (2013.01); *A61K 8/0266* (2013.01); *A61K 8/042* (2013.01);
(Continued)

(58) Field of Classification Search
CPC ..... H01L 31/035218; H01L 31/035227; H01L 31/055; H01L 31/065; Y02E 10/50
(Continued)

(56) References Cited

U.S. PATENT DOCUMENTS

2004/0187912 A1    9/2004  Takamoto et al.
2007/0084505 A1*   4/2007  Zaidi ............... H01L 31/035281
                                                            136/256
(Continued)

FOREIGN PATENT DOCUMENTS

EP    2 184 786 A1    5/2010
JP    A-2001-308365   11/2001
(Continued)

OTHER PUBLICATIONS

Shala V et al., "Luminescent Layers for Enhanced Silicon Solar Cell Performance: Up-Conversion," *Solar Energy Materials & Solar Cells*, 2007, vol. 91, pp. 829-842.
(Continued)

*Primary Examiner* — Thanh-Truc Trinh
(74) *Attorney, Agent, or Firm* — Oliff PLC

(57) ABSTRACT

A photoelectric conversion device includes: a wavelength converting region that absorbs ambient light to generate electrons and holes, and recombines the generated electrons and holes to generate monochromatic light; and a photoelectric conversion region that has a p-n junction or p-i-n junction, absorbs the monochromatic light generated in the wavelength converting region to generate electrons and holes, and separates and moves the electrons and holes generated by absorption of the monochromatic light. The wavelength converting region includes: a carrier generating region that generates the electrons and holes; a light emitting region that generates the monochromatic light; and a carrier selective transfer region that is disposed between the carrier
(Continued)

generating region and the light emitting region and that, of the electrons and holes generated in the carrier generating region, moves those electrons and holes having specific energies difference there between to the light emitting region.

11 Claims, 17 Drawing Sheets

(51) Int. Cl.
 A61K 8/04 (2006.01)
 A61K 8/73 (2006.01)
 A61Q 11/00 (2006.01)
(52) U.S. Cl.
 CPC .............. *A61K 8/731* (2013.01); *A61K 8/732* (2013.01); *A61Q 11/00* (2013.01); *A61K 2800/262* (2013.01); *A61K 2800/594* (2013.01); *A61K 2800/621* (2013.01); *A61K 2800/651* (2013.01)
(58) Field of Classification Search
 USPC .................................................. 136/243–293
 See application file for complete search history.

(56) References Cited

U.S. PATENT DOCUMENTS

| 2010/0258164 | A1 | 10/2010 | Takeda et al. |
| 2010/0288344 | A1* | 11/2010 | Spitzer .................. H01L 31/055 136/255 |
| 2010/0294366 | A1 | 11/2010 | Kanesato et al. |
| 2011/0126889 | A1 | 6/2011 | Bourke, Jr. et al. |

FOREIGN PATENT DOCUMENTS

| JP | A-2004-296658 | 10/2004 |
| JP | A-2006-114815 | 4/2006 |
| JP | A-2006-303033 | 11/2006 |
| JP | A-2009-059915 | 3/2009 |
| JP | A-2010-118491 | 5/2010 |
| JP | A-2012-114378 | 6/2012 |
| WO | WO 2008/047427 A1 | 4/2008 |
| WO | WO 2009/028492 A1 | 3/2009 |
| WO | 2010/036109 A2 | 4/2010 |
| WO | WO 2011/000055 A1 | 1/2011 |
| WO | WO 2012/069926 A2 | 5/2012 |

OTHER PUBLICATIONS

Green, "Third Generation Photovoltaics: Ultra-High Conversion Efficiency at Low Cost," *Progress in Photovoltaics: Research and Applications*, 2001, vol. 9, pp. 123-135.

Trupke et al., "Improving Solar Cell Efficiencies by Down-Conversion of High-Energy Photons," Journal of Applied Physics, Aug. 1, 2002, vol. 92, No. 3, pp. 1668-1674.

Trupke et al., "Improving Solar Cell Efficiencies by Up-Conversion of Sub-Band-Gap Light," *Journal of Applied Physics*, Oct. 1, 2002, vol. 92, No. 7, pp. 4117-4122.

Wurfel et al., "Particle Conservation in the Hot-Carrier Solar Cell," *Progress in Photovoltaics: Research and Applications*, Feb. 18, 2005, vol. 13, pp. 277-285.

Trupke et al., "Efficiency Enhancement of Solar Cells by Luminescent Up-Conversion of Sunlight," *Solar Energy Materials & Solar Cells*, Aug. 2, 2006, vol. 90, pp. 3327-3338.

Conibeer et al., "Progress on Hot Carrier Cells," *Solar Energy Materials & Solar Cells*, Dec. 21, 2008, vol. 93, pp. 713-719.

Takeda et al., "Impact Ionization and Auger Recombination at High Carrier Temperature," *Solar Energy Materials & Solar Cells*, Nov. 29, 2008, vol. 93, pp. 797-802.

Takeda et al., "Hot Carrier Solar Cells Operating Under Practical Conditions," Journal of Applied Physics, Apr. 8, 2009, vol. 105, pp. 074905-1-704905-10.

Takeda et al., "Practical Factors Lowering Conversion Efficiency of Hot Carrier Solar Cells," Applied Physics Express, Oct. 15, 2010, vol. 3, pp. 104301-1-104301-3.

Takeda et al., "Highly Efficient Solar Cells Using Hot Carriers Generated by Two-Step Excitation," *Solar Energy Materials & Solar Cells*, Jun. 2, 2011, vol. 95, pp. 2638-2644.

Farrell et al., "A Hot-Carrier Solar Cell with Optical Energy Selective Contacts," Applied Physics Letters, Sep. 12, 2011, vol. 99, pp. 111102-1-111102-3.

* cited by examiner

PHOTOELECTRIC CONVERSION DEVICE

BACKGROUND OF THE INVENTION

1. Field of the Invention

The invention relates to a photoelectric conversion device, and more particularly to a photoelectric conversion device that uses a wavelength converting mechanism.

2. Description of Related Art

Solar cells capable of converting sunlight energy directly into electricity are expected to serve as a next-generation source of green energy. Because there is a certain limitation to the area for installing a solar cell, the photoelectric conversion efficiency must be increased to obtain a greater amount of electricity. To this end, current development efforts are aimed at, for example, optimizing the device structure and manufacturing operations, and achieving higher levels of quality in the silicon used as the primary material.

Technology relating to such solar cells includes, for example, Japanese Patent Application Publication No. 2009-59915 (JP-2009-59915 A) that discloses art relating to a "hot carrier-type" solar cell that, in order to reduce energy loss of charge carriers (electrons and holes; the same applies below) generated using light having a higher energy than the energy gap of the semiconductor making up a light absorbing layer, promotes energy interactions (transfer) between carriers in the light absorbing layer and extracts electrons having a high energy. Japanese Patent Application Publication No. 2004-296658 (JP-2004-296658 A) discloses art relating to a multi-junction solar cell that uses, as a top cell, a solar cell that is formed of an AlInGaP material and has a p-n junction, and uses, as a bottom cell, a solar cell that is lattice matched with the top cell, formed of an InGaAsN material and has a p-n junction, in which multi-junction solar cell the compositional ratio of aluminum in the group III elements of the AlInGaP material making up the top cell is in the range of 0.05 to 0.15. Japanese Patent Application Publication No. 2006-114815 (JP-2006-114815 A) discloses a solar cell that has a p-i-n structure and contains, in an i layer that is a photodetection layer, quantum dots that exhibit three-dimensional quantum confinement effects, wherein the quantum dots and the barrier layers enclosing them have a type II band structure. International Publication No. 2008/047427 (WO 2008/047427) discloses a solar cell module with a structure that incorporates a plurality of units having a front cover, a back cover and, between these covers, a crystalline silicon cell encapsulated within an encapsulant, wherein the encapsulant between the front cover and the crystalline silicon cell contains a fluorescent resin composition composed of an ethylene-vinyl acetate copolymer containing 0.01 to 10 wt % of an organic rare earth metal complex that fluoresces in the wavelength range of 550 to 900 nm. In addition, *Solar Energy Materials and Solar Cells* (Netherlands), Vol. 91, No. 9, 829-842 (2007) discloses art relating to an "up-conversion type" solar cell that reduces light transmission loss by long-wavelength light having lower energy than the energy gap of the semiconductor making up the light absorption layer by converting the long-wavelength light to a wavelength suitable for the energy gap of the semiconductor making up the light absorption layer.

To obtain a high photoelectric conversion efficiency in a hot carrier solar cell, it is necessary to promote energy interactions (transfer) between the charge carriers and allow the carriers to move from the absorption layer to the electrodes while retaining a high energy. Hence, it is thought to be essential for hot carriers to have a lifetime of at least one nanosecond. Yet, in current semiconductor materials, the lifetime of hot carriers is limited to a range of from several picoseconds up to several hundreds of picoseconds. Hence, even using the art disclosed in JP-2009-59915 A, the photoelectric conversion efficiency increasing effect has tended to be inadequate. In the multi-junction type solar cell disclosed in JP-2004-296658 A, because light of a broad range of wavelengths included in sunlight can be absorbed, it should presumably also be possible to increase the photoelectric conversion efficiency. However, in a multi-junction type solar cell, the number of semiconductor interfaces having a high density of defects that annihilate carriers and cause a decline in the photoelectric conversion efficiency rises due to the increased number of junctions. Also, costs have tended to rise on account of the need to use many expensive III-V compound materials and the increased number of production steps. In the up-conversion solar cell disclosed in *Solar Energy Materials and Solar Cells* (Netherlands), Vol. 91, No. 9, 829-842 (2007) and down-conversion solar cells that reduce energy loss by converting high-energy, short-wavelength light to a wavelength light suitable for the energy gap of the semiconductor making up the light absorbing layer, fluorescent materials that employ rare-earth elements such as those disclosed in WO 2008/047427 are used in many cases. However, because the wavelength range of light that can be absorbed by conventional fluorescent materials that employ rare-earth elements is narrow and energy loss during wavelength conversion is large, the photoelectric conversion efficiency-increasing effects of conventional down-conversion solar cells and up-conversion solar cells have tended to be inadequate. That is, even by combining the teachings of the various art disclosed in JP-2009-59915 A, JP-2004-296658 A, JP-2006-114815 A, WO 2008/047427 and *Solar Energy Materials and Solar Cells* (Netherlands), Vol. 91, No. 9, 829-842 (2007), it is difficult to increase the photoelectric conversion efficiency.

SUMMARY OF THE INVENTION

The invention provides a photoelectric conversion device, with which it is possible to increase the photoelectric conversion efficiency.

A first aspect of the invention is a photoelectric conversion device having a wavelength converting region that absorbs ambient light to generate electrons and holes, and recombines the generated electrons and holes to generate monochromatic light; and a photoelectric conversion region that has a p-n junction or p-i-n junction, absorbs the monochromatic light generated in the wavelength converting region to generate electrons and holes, and separates and moves the electrons and holes generated by absorption of the monochromatic light. The wavelength converting region includes a carrier generating region that generates the electrons and holes, a light emitting region that generates the monochromatic light, and a carrier selective transfer region that is disposed between the carrier generating region and the light emitting region and that moves, of the electrons and holes generated in the carrier generating region, an electron and a hole having a specific energy difference therebetween to the light emitting region.

In the first aspect of the invention and in other aspects of the invention that are subsequently described (collectively referred to below as simply "the invention"), the wavelength converting region has the function of, using a hot carrier mechanism, increasing the efficiency of monochromatic light generation from sunlight, and making it possible to adjust the light wavelength at will. In the invention, the term 'ambient light' means the light that falls on the photoelectric conversion device from the surroundings, or environment, and is therefore, for example, polychromatic light such as sunlight. Moreover, in the invention, "photoelectric conversion device" is a concept that includes not only solar cells, but also photodetectors and the like. In the description of the invention that follows, polychromatic light is also referred to as simply "light."

The wavelength converting region may be disposed on an upstream side of the photoelectric conversion region in a traveling direction of the ambient light. In the invention, "upstream side in a traveling direction of the ambient light" means the upstream side in the direction in which the ambient light (polychromatic light) travels. That is, "the wavelength converting region is disposed on an upstream side of the photoelectric conversion region in a traveling direction of the ambient light" signifies that a wavelength converting region and a photoelectric conversion region are arranged so as to make it possible for ambient light (polychromatic light), before reaching the photoelectric conversion region, to enter the wavelength converting region, and for monochromatic light generated in the wavelength converting region to be absorbed in the photoelectric conversion region. More concretely, this means that the wavelength converting region is situated on the upstream side in the direction in which the ambient light (polychromatic light) travels, and that the photoelectric conversion region is situated on the downstream side of the wavelength converting region in the direction in which the ambient light (polychromatic light) travels. According to a photoelectric conversion device thus configured, electrons and holes (sometimes collectively referred to below as "carriers") are generated by the absorption of ambient light in the wavelength converting region situated on the upstream side of the photoelectric conversion region in the traveling direction of the ambient light, and the monochromatic light generated by recombination of the carriers in the light emitting region is input to the photoelectric conversion region.

For example, by employing a configuration that generates monochromatic light in the wavelength converting region using a hot carrier mechanism, it becomes possible to reduce energy loss of the carriers that move to the light emitting region. Also, by controlling the size and thickness of the carrier generating region (e.g., in cases where the carrier generating region is spherical or cylindrical, setting the diameter to 20 nm or less; in cases where the carrier generating region is in the shape of a film, setting the film thickness to 20 nm or less), the movement length of the earners generated in the carrier generating region can be reduced, and it becomes possible to reduce energy loss of carriers that move to the light emitting region. A purpose of the wavelength converting region in the invention is to allow the carriers to recombine at the light emitting region; it is not intended to extract the generated carriers directly to the exterior. Accordingly, unlike in conventional hot carrier solar cells that use a quantum structure, there is no need to have the carriers move all the way to the electrodes, so that it is made possible to markedly reduce the loss of energy during carrier movement. In addition, by employing a configuration that uses a semiconductor material in the wavelength converting region, the wavelength range of light that can be used to generate carriers can be greatly expanded as compared to conventional down-conversion solar cells that use fluorescent materials. Also, by adjusting the composition and shape of the semiconductor materials used in the carrier selective transfer region or the light emitting region, it is possible to more freely regulate the wavelength of the monochromatic light generated in the light emitting region than in conventional down-conversion solar cells that use fluorescent materials having limited emission wavelengths. In addition, by inputting monochromatic light to the photoelectric conversion region, the energy of the monochromatic light that is input to the photoelectric conversion region is fixed. Hence, by using in the photoelectric conversion region a semiconductor material having an energy gap that corresponds to the energy of the monochromatic light input to the photoelectric conversion region (specifically, an energy gap that is the same as the energy of monochromatic light, or is about 0.1 eV smaller than the energy of monochromatic light; the same applies below), it becomes possible to reduce energy loss. Accordingly, a photoelectric conversion device, with which it is possible to increase the photoelectric conversion efficiency, can be provided. Also the photoelectric conversion efficiency is easily increased by increasing the efficiency of the wavelength converting region that converts ambient light into monochromatic light.

In the above first aspect of the invention, the wavelength converting region may be disposed on a downstream side of the photoelectric conversion region in a traveling direction of the ambient light, and the wavelength converting region may further include a light reflecting region that reflects the monochromatic light toward the photoelectric conversion region side.

Here, in the invention, "downstream side in the traveling direction of the ambient light" means the downstream side in the direction of travel of ambient light (polychromatic light). That is, "the wavelength converting region is disposed on a downstream side of the photoelectric conversion region in the traveling direction of the ambient light" signifies that the wavelength converting region and the photoelectric conversion region are arranged so as to make it possible for ambient light to enter the photoelectric conversion region, for light that has passed through the photoelectric conversion region to enter the wavelength converting region, and for monochromatic light generated in the wavelength converting region using the light that has entered therein to enter the photoelectric conversion region. More concretely, this means that the photoelectric conversion region is situated on the upstream side in the direction of travel of the ambient light entering the photoelectric conversion region, and that the wavelength converting region is situated on the downstream side of the photoelectric conversion region in the traveling direction of the ambient light.

With a photoelectric conversion device of the foregoing configuration, the electrons and holes generated using light that has passed through the photoelectric conversion region situated on the upstream side of the wavelength converting region in the traveling direction of the ambient light are recombined in the light emitting region. That is, light having a higher energy than the energy gap of the semiconductor material included in the photoelectric conversion region is absorbed by the photoelectric conversion region and converted to electricity, and the light that has not been converted to electricity in the photoelectric conversion region enters the wavelength converting region. In the wavelength converting region, using a semiconductor material, for example, carriers are generated by absorbing light having a higher energy than the energy gap of this semiconductor material (energy gap of semiconductor material making up wavelength converting region <energy gap of semiconductor material making up photoelectric conversion region). By having the electrons thus generated mutually interact and the holes thus generated mutually interact using, for example, a hot carrier mechanism, monochromatic light having a larger energy than the energy gap of the semiconductor material making up the photoelectric conversion region is generated. This monochromatic light enters into and is absorbed by the photoelectric conversion region, from which electricity is then extracted. By employing such a configuration, it becomes possible to reduce the energy loss of carriers generated in the carrier generating region. Also, by controlling the size and thickness of the carrier generating region (e.g., in cases where the carrier generating region is spherical or cylindrical, setting the diameter to 20 nm or less; in cases where the carrier generating region is in the shape of a film, setting the film thickness to 20 nm or less), the movement length of earners generated in the carrier generating region can be reduced, and it becomes possible to reduce energy loss of carriers that move to the light emitting region. A purpose of the wavelength converting region is to allow the electrons and holes to recombine in the light emitting region; it is not intended to extract the generated electrons and holes directly to the exterior. Accordingly, unlike in conventional hot carrier solar cells that use a quantum structure, there is no need to have the carriers move all the way to the electrodes, so that it is made possible to significantly reduce the energy loss during carrier movement. In addition, by employing a configuration that uses a semiconductor material in the wavelength converting region, the wavelength range of light that can be used to generate carriers can be greatly expanded as compared to conventional up-conversion solar cells that use fluorescent materials. Also, by adjusting the composition and shape of the semiconductor materials used for the carrier selective transfer region or the light emitting region, it becomes possible to more freely regulate the wavelength of the monochromatic light generated in the light emitting region than in conventional up-conversion solar cells that use fluorescent materials having limited emission wavelengths. In addition, by using, for the photoelectric conversion region, a semiconductor material having an energy gap that corresponds to the energy of the monochromatic light input to the photoelectric conversion region, it becomes possible to reduce energy loss. Accordingly, a photoelectric conversion device, with which it is possible to increase the photoelectric conversion efficiency, can be provided. Also the photoelectric conversion efficiency is readily increased by increasing the efficiency of the wavelength converting region that converts ambient light into monochromatic light.

In the first embodiment of the invention, the wavelength converting region may be disposed within the photoelectric conversion region.

According to a photoelectric conversion device configured in this way, in the wavelength converting region disposed within the photoelectric conversion region, electrons and holes are generated using the light that has passed through the photoelectric conversion region. By then allowing these electrons and holes to recombine in the light emitting region within the wavelength converting region, monochromatic light having a larger energy than the energy gap of the semiconductor material making up the photoelectric conversion region is generated. This monochromatic light enters and is absorbed by the photoelectric conversion region, resulting in the output of electricity. With such a configuration, it becomes possible to achieve effects similar to those of the above-described configuration in which the wavelength converting region is disposed on the downstream side of the photoelectric conversion region in the traveling direction of the ambient light. Accordingly, a photoelectric conversion device, with which it is made possible to increase the photoelectric conversion efficiency, can be provided. Moreover, by increasing the efficiency of the wavelength converting region that converts ambient light to monochromatic light, the photoelectric conversion efficiency is readily increased.

In the first aspect of the invention, a wavelength converting particle having, in sequence concentrically from a center side outward, the carrier generating region, the carrier selective transfer region and the light emitting region may be included in the wavelength converting region. The above-described effects in the first aspect of the invention can be obtained also when such a wavelength converting particle is included in the wavelength converting region.

In the first aspect of the invention in which a wavelength converting particle is included in the wavelength converting region, the wavelength converting particles may be dispersed and held in a transparent material included in the wavelength converting region. The transparent material may be an electrically insulating material and/or a semiconductor material having a larger energy gap than the material making up the carrier generating region of the wavelength converting particles. When the wavelength converting particles are dispersed and held within the transparent material, it is made easy to maintain the above effects in the first aspect of the invention for a long period of time.

In the first aspect of the invention, the wavelength converting region may include a wavelength converting fiber having, in sequence concentrically from a center side outward, the carrier generating region, the carrier selective transfer region, and the light emitting region. The above-described effects in the first aspect of the invention can be obtained also when such a wavelength converting fiber is included in the wavelength converting region.

In the invention, the "wavelength converting fiber" means a substance that, rather than being spherical like the wavelength converting particles, is in a linear form that extends in one direction (axial direction) like carbon nanotubes.

In the first aspect of the invention in which a wavelength converting fiber is included in the wavelength converting region, the wavelength converting fibers may be dispersed and held in a transparent material included in the wavelength converting region. The transparent material may be an electrically insulating material and/or a semiconductor material having a larger energy gap than the material making up the carrier generating region of the wavelength converting fibers. When the wavelength converting fibers are dispersed and held within the transparent material, it is made easy to maintain the above effects in the first aspect of the invention for a long period of time.

In the first aspect of the invention, the wavelength converting region may include a wavelength converting film having the carrier generating region, the carrier selective transfer region and the light emitting region that are stacked so that the carrier selective transfer region is disposed between the carrier generating region and the light emitting region. The above-described effects in the first aspect of the invention can be obtained also when such a wavelength converting film is included in the wavelength converting region.

In the first aspect of the invention, the p-n junction may have sites where a p-type material and an n-type material are three-dimensionally joined. The above-described effects in the first aspect of the invention can be obtained also when the p-n junction includes sites where a p-type material (a material that functions as a p-type semiconductor; the same applies below) and an n-type material (a material that functions as an n-type semiconductor; the same applies below) are three-dimensionally joined. An example of a p-n junction having sites where a p-type material and an n-type material are three-dimensionally joined is a p-n junction having a so-called bulk heterostructure.

In the first aspect of the invention, assuming that $Eg1$, $Ec1$ and $Ev1$ are, respectively, an energy gap, a conduction-band minimum, and a valence-band maximum for a material making up the carrier generating region; $Eg2$, $Ec2$ and $Ev2$ are, respectively, an energy gap, a conduction-band minimum, and a valence-band maximum for a material making up the light emitting region; and $Eg3$, $Ec3$ and $Ev3$ are, respectively, an energy gap, an energy at a lowest discrete energy level in a conduction band, and an energy at a lowest discrete energy level in a valence band for a material making up the carrier selective transfer region in a shape in which the material is incorporated within the wavelength converting region, the following relations may be satisfied: $Eg1<Eg2 \leq Eg3$; $Ec1<Ec2 \leq Ec3$; and $Ev3 \leq Ev2 \leq Ev1$. The above-described effects in the first aspect of the invention can be obtained also in this configuration (type I).

In the invention, "lowest discrete energy level in the conduction band" means, of the discrete energy levels (quantum levels) formed in the conduction band, the discrete energy level (quantum level) having the lowest energy. That is, in the case of a band diagram drawn such that an upper region of the diagram indicates a higher energy of an electron and a lower region of the diagram indicates a higher energy of a hole, the discrete energy level (quantum level) located at the bottom of the conduction band is the lowest discrete energy level in the conduction band. Moreover, the energy gap for the carrier selective transfer region means the energy difference between the lowest discrete energy level in the conduction band and the lowest discrete energy level in the valence band. The energy levels of the conduction band or valence band are sometimes discrete also for the material making up the carrier generating region or for the light emitting region, depending on the size thereof. In the above description, "bottom edge of the conduction band" means the lowest discrete energy level in the conduction band, "top edge of the valence band" means the lowest discrete energy level in the valence band, and "energy gap" means the energy difference between the lowest discrete energy level in the conduction band and the lowest discrete energy level in the valence band. In the invention, "lowest discrete energy level in the valence band" means that discrete energy level (quantum level) having the lowest energy of all the discrete energy levels (quantum levels) formed in the valence band. That is, in the case of a band diagram drawn such that an upper region of the diagram indicates a higher energy of an electron and a lower region of the diagram indicates a higher energy of a hole, the discrete energy level (quantum level) located at the top of the valence band is the lowest discrete energy level in the valence band. Also, in this invention, "an energy gap of a material making up the carrier selective transfer region" means the energy gap of that material having the smallest energy gap of the materials making up the carrier selective transfer region. In the invention, "$Ev3 \leq Ev2 \leq Ev1$" signifies that, in the case of band diagram drawn such that an upper region of the diagram indicates a higher energy of an electron and a lower region of the diagram indicates a higher energy of a hole, $Ev3$ has the same height as $Ev2$ or is positioned lower than $Ev2$, and $Ev2$ has the same height as $Ev1$ or is positioned lower than $Ev1$.

In the above-described first aspect of the invention, assuming that $Eg4$, $Ec4$ and $Ev4$ are, respectively, an energy gap, a conduction-band minimum, and a valence-band maximum for a material making up the earner generating region; $Eg5$, $Ec5$ and $Ev5$ are, respectively, an energy gap, a conduction-band minimum, and a valence-band maximum for a material making up the light emitting region; and $Eg6$, $Ec6$ and $Ev6$ are, respectively, an energy gap, an energy at a lowest discrete energy level in a conduction band, and a valence-band maximum for a material making up the carrier selective transfer region in a shape in which the material is incorporated within the wavelength converting region, the following relations may be satisfied: $Eg4<Eg5<Eg6$; $Ec4<Ec5<Ec6$; and $Ev4<Ev6<Ev5$. The above-described effects in the first aspect of the invention can be obtained also in this configuration (type II). In the invention, "$Ev4<Ev6<Ev5$" signifies that, in the case of a band diagram drawn such that an upper region of the diagram indicates a higher energy of an electron and a lower region of the diagram indicates a higher energy of a hole, $Ev4$ has the same height as $Ev6$ or is positioned lower than $Ev6$, and $Ev6$ has the same height as $Ev5$ or is positioned lower than $Ev5$.

In the first aspect of the invention, a surface of the light emitting region may be covered with an insulator or a semiconductor material having a larger energy gap than the material making up the carrier generating region. With such a configuration, it becomes possible to reduce the defects that may be present at the surface of the light emitting region, and it is therefore made possible to reduce the carriers that are trapped by such defects and thus do not recombine, so that it is made easy to increase the photoelectric conversion efficiency.

In the first aspect of the invention, the light emitting region may include a pair of first semiconductor regions composed of a first semiconductor; and a second semiconductor region that is disposed between the pair of first semiconductor regions, and is composed of a second semiconductor having a smaller energy gap that the first semiconductor. With such a configuration, carrier recombination arises more easily in the second semiconductor region, so that it is made easy to increase the photoelectric conversion efficiency.

In the first aspect of the invention, the carrier selective transfer region may include a pair of wide-gap semiconductor regions composed of a wide-gap semiconductor; and a narrow-gap semiconductor region that is disposed between the pair of wide-gap semiconductor regions, and is composed of a narrow-gap semiconductor having a smaller energy gap than the wide-gap semiconductor. The above-described effects in the first aspect of the invention are more easily achieved with such a configuration.

According to a second aspect, the invention provides a photoelectric conversion device having a wavelength converting region that absorbs ambient light to generate electrons and holes, and recombines the generated electrons and holes to generate monochromatic light; and a photoelectric conversion region that has a p-n junction or p-i-n junction, absorbs the monochromatic light generated in the wavelength converting region to generate electrons and holes, and separates and moves the electrons and holes generated by absorption of the monochromatic light. The wavelength converting region includes a carrier generating region that generates the electrons and holes; a light emitting region that moves, of the electrons and holes generated in the carrier generating region, an electron and a hole having a specific energy difference therebetween to the light emitting region itself, and generates the monochromatic light by recombining the electron and hole moved to the light emitting region itself; and an outside material region that is disposed outside of the light emitting region and is composed of a material having a larger energy gap than a material making up the light emitting region.

The wavelength converting region may be disposed on an upstream side of the light converting region in a traveling direction of the light. With a photoelectric conversion device configured in this way, carriers are generated by the entry and absorption of ambient light at the wavelength converting region disposed on the upstream side of the light converting region in the traveling direction of the ambient light, and monochromatic light generated by recombination of the generated carriers in the light emitting region can be input to the photoelectric conversion region.

For example, by employing a configuration that generates monochromatic light in the light emitting region using a hot carrier mechanism, it is possible to reduce energy loss of the carriers that move to the light emitting region. Also, by controlling the size and thickness of the carrier generating region (e.g., in cases where the carrier generating region is spherical or cylindrical, setting the diameter to 20 nm or less; in cases where the carrier generating region is in the shape of a film, setting the film thickness to 20 nm or less), the movement length of the carriers generated in the carrier generating region can be reduced, and it becomes possible to reduce energy loss of carriers moving to the light emitting region. A purpose of the wavelength converting region in the invention is to allow the carriers to recombine at the light emitting region; it is not intended to extract the generated carriers directly to the exterior. Accordingly, unlike in conventional hot carrier solar cells that use a quantum structure, there is no need to have the carriers move all the way to the electrodes, so that it is made possible to markedly reduce the loss of energy during carrier movement. In addition, by employing a configuration that uses a semiconductor material in the wavelength converting region, the wavelength range of light that can be used to generate carriers can be greatly expanded as compared to conventional down-conversion solar cells that use fluorescent materials. Also, by adjusting the composition and shape of the semiconductor materials used in the light emitting region, it is possible to more freely regulate the wavelength of the monochromatic light generated in the light emitting region than in conventional down-conversion solar cells that use fluorescent materials having limited emission wavelengths. In addition, by inputting monochromatic light to the photoelectric conversion region, the energy of the monochromatic light that is input to the photoelectric conversion region is fixed. Hence, by using in the photoelectric conversion region a semiconductor material having an energy gap that corresponds to the energy of the monochromatic light input to the photoelectric conversion region, it becomes possible to reduce energy loss. Accordingly, with the second aspect of the invention, it is possible to provide a photoelectric conversion device, with which it is possible to increase the photoelectric conversion efficiency. Also by increasing the efficiency of the wavelength converting region that converts ambient light into monochromatic light, the photoelectric conversion efficiency is easily increased.

In the invention, "a material having a larger energy gap than a material making up the light emitting region" includes not only semiconductor materials, but also electrically insulating materials.

In the second aspect of the invention, the wavelength converting region may be disposed on a downstream side of the light converting region in a traveling direction of the ambient light, and the wavelength converting region may further include a light reflecting region that reflects the monochromatic light toward the photoelectric conversion region side.

With a photoelectric conversion device of the foregoing configuration, the electrons and holes generated using light that has passed through the photoelectric conversion region situated on the upstream side of the wavelength converting region in the traveling direction of the ambient light are recombined in the light emitting region. That is, light having a larger energy than the energy gap of the semiconductor material included in the photoelectric conversion region is absorbed by the photoelectric conversion region and converted to electricity; the light that has not been converted to electricity in the photoelectric conversion region enters the wavelength converting region. In the wavelength converting region, using a semiconductor material, for example, carriers are generated by absorbing light having a larger energy than the energy gap of this semiconductor material (energy gap of semiconductor material making up wavelength converting region <energy gap of semiconductor material making up photoelectric conversion region). By having the electrons thus generated mutually interact and the holes thus generated mutually interact using, for example, a hot carrier mechanism, monochromatic light having a larger energy than the energy gap of the semiconductor material making up the photoelectric conversion region is generated. This monochromatic light enters into and is absorbed by the photoelectric conversion region, from which electricity is then extracted. By employing such a configuration, it becomes possible to reduce the energy loss of carriers generated in the carrier generating region. Also, by controlling the size and thickness of the carrier generating region (e.g., in cases where the earner generating region is spherical or cylindrical, setting the diameter to 20 nm or less, in cases where the carrier generating region is in the shape of a film, setting the film thickness to 20, nm or less), the movement length of carriers generated in the carrier generating region can be reduced, and it becomes possible to reduce energy loss of carriers moving to the light emitting region. A purpose of the wavelength converting region is to allow the electrons and holes to recombine at the light emitting region; it is not intended to extract the generated electrons and holes directly to the exterior. Accordingly, unlike in conventional hot carrier solar cells that use a quantum structure, there is no need to have the carriers move all the way to the electrodes, so that it is made possible to significantly reduce the energy loss during carrier movement. In addition, by employing a configuration that uses a semiconductor material in the wavelength converting region, the wavelength range of light that can be used to generate carriers can be greatly expanded as compared to conventional up-conversion solar cells that use fluorescent materials. Also, by adjusting the composition and shape of the semiconductor materials used in the light emitting region, it becomes possible to more freely regulate the wavelength of the monochromatic light generated in the light emitting region than in conventional up-conversion solar cells that use fluorescent materials having limited emission wavelengths. In addition, by using, for the photoelectric conversion region, a semiconductor material having an energy gap that corresponds to the energy of the monochromatic light input to the photoelectric conversion region, it becomes possible to reduce energy loss. Accordingly, a photoelectric conversion device, with which it is possible increase the photoelectric conversion efficiency, can be provided. Also the photoelectric conversion efficiency is easily increased by increasing the efficiency of the wavelength converting region that converts ambient light into monochromatic light.

In the second aspect of the invention, the wavelength converting region may be disposed within the photoelectric conversion region.

According to a photoelectric conversion device configured in this way, in the wavelength converting region disposed within the photoelectric conversion region, electrons and holes are generated using the light that has passed through the photoelectric conversion region. By then allowing these electrons and holes to recombine in the light emitting region within the wavelength converting region, monochromatic light having a larger energy than the energy gap of the semiconductor material making up the photoelectric conversion region is generated. This monochromatic light enters and is absorbed by the photoelectric conversion region, resulting in the output of electricity. With such a configuration, it becomes possible to achieve effects similar to those of the above-described configuration in which the wavelength converting region is disposed on the downstream side of the photoelectric conversion region in the traveling direction of the ambient light. Accordingly, a photoelectric conversion device, with which it is made possible to increase the photoelectric conversion efficiency, can be provided. Moreover, by increasing the efficiency of the wavelength converting region that converts ambient light to monochromatic light, the photoelectric conversion efficiency is readily increased.

In the second aspect of the invention, a wavelength converting particle having, in sequence concentrically from a center side outward, the carrier generating region, the light emitting region and the outside material region may be included in the wavelength converting region. The above-described effects in the second aspect of the invention can be obtained also when such a wavelength converting particle is included in the wavelength converting region.

In the second aspect of the invention in which wavelength converting particle is included in the wavelength converting region, the wavelength converting particles may be dispersed and held in a transparent material included in the wavelength converting region. The transparent material may be an electrically insulating material and/or a semiconductor material having a larger energy gap than the material making up the carrier generating region of the wavelength converting particles. When the wavelength converting particles are dispersed and held within the transparent material, it is made easy to maintain the above-described effects in the second aspect of the invention for a long period of time.

In the second aspect of the invention, the wavelength converting region may include a wavelength converting fiber having, in sequence concentrically from a center side outward, the carrier generating region, the light emitting region and the outside material region. The above-described effects in the second aspect of the invention can be obtained also when such a wavelength converting fiber is included in the wavelength converting region.

In the second aspect of the invention in which a wavelength converting fiber is included in the wavelength converting region, the wavelength converting fibers may be dispersed and held in a transparent material included in the wavelength converting region. The transparent material may be an electrically insulating material and/or a semiconductor material having a larger energy gap than the material making up the carrier generating region of the wavelength converting fibers. When the wavelength converting fibers are dispersed and held within the transparent material, it is made easy to maintain the above-described effects in the second aspect of the invention for a long period of time.

In the second aspect of the invention, the wavelength converting region may include a wavelength converting film having the carrier generating region, the light emitting region and the outside material region that are stacked so that the light emitting region is disposed between the carrier generating region and the outside material region. The above-described effects in the second aspect of the invention can be obtained also when such a wavelength converting film is included in the wavelength converting region.

In the above-described second aspect of the invention, the p-n junction may have sites where a p-type material and an n-type material are three-dimensionally joined. The above-described effects in the second aspect of the invention can be obtained also when the p-n junction includes sites where a p-type material and an n-type material are three-dimensionally joined. An example of a p-n junction having sites where a p-type material and an n-type material are three-dimensionally joined is a p-n junction having a so-called bulk heterostructure.

In the above-described second aspect of the invention, assuming that $Eg7$, $Ec7$ and $Ev7$ are, respectively, an energy gap, a conduction-band minimum, and a valence-band maximum for a material making up the carrier generating region; $Eg8$, $Ec8$ and $Ev8$ are, respectively, an energy gap, an energy at a lowest discrete energy level in a conduction band, and an energy at a lowest discrete energy level in a valence band, for a material making up the light emitting region in a shape in which the material is incorporated within the wavelength converting region; and $Eg9$, $Ec9$ and $Ev9$ are, respectively, an energy gap, a conduction-band minimum, and a valence-band maximum for a material making up the outside material region, the following relations may be satisfied: $Eg7<Eg8<Eg9$; $Ec7<Ec8<Ec9$; and $Ev9<Ev8<Ev7$. The above-described effects in the second aspect of the invention are readily achieved with this configuration. In the invention, "$Ev9<Ev8<Ev7$" signifies that, in the case of a band diagram drawn such that an upper region of the diagram indicates a higher energy of an electron and a lower region of the diagram indicates a higher energy of a hole, $Ev9$ is positioned lower than $Ev8$, and $Ev8$ is positioned lower than $Ev7$.

In the second aspect of the invention, the light emitting region may include a pair of wide-gap semiconductor regions composed of a wide-gap semiconductor; and a narrow-gap semiconductor region that is disposed between the pair of wide-gap semiconductor regions, and is composed of a narrow-gap semiconductor having a smaller energy gap than the wide-gap semiconductor. The above-described effects in the second aspect of the invention are readily achieved with such a configuration.

According to the invention, it is possible to provide a photoelectric conversion device, with which it is possible to increase the photoelectric conversion efficiency.

BRIEF DESCRIPTION OF THE DRAWINGS

Features, advantages, and the technical and industrial significance of exemplary embodiments of the invention will be described below with reference to the accompanying drawings, in which like numerals denote like elements, and wherein.

DETAILED DESCRIPTION OF EMBODIMENTS

Figure 1A:
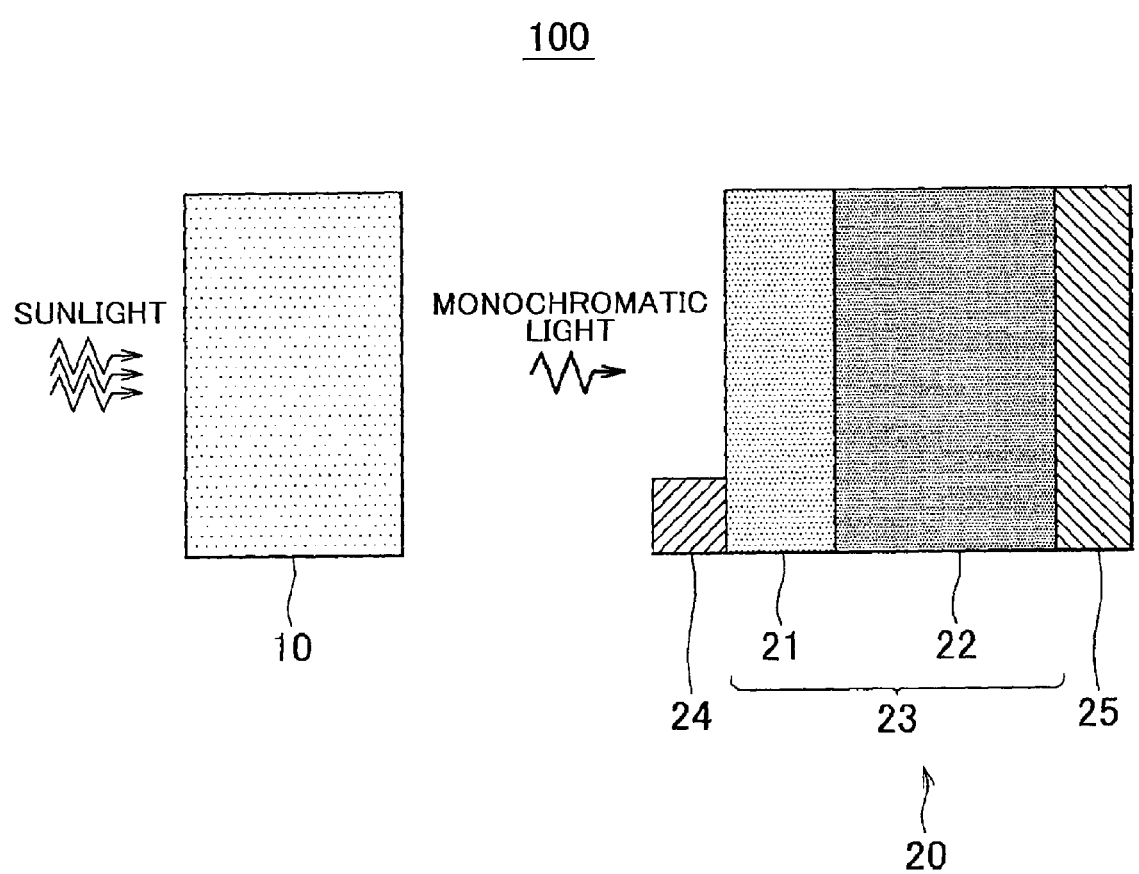
FIG. 1A is a sectional view of a solar cell according to a first embodiment of the invention.

Solar cells serving as embodiments of the invention are described below with reference to the accompanying diagrams. The following embodiments are provided to illustrate the invention, and the invention is not limited to these embodiments. It should be noted that some reference symbols have been omitted from the diagrams.

FIG. 1 A is a sectional view showing a solar cell 100 according to a first embodiment of the invention, and FIG. 1 B is a diagram illustrating the band structure of the solar cell 100. In FIG. 1 A, description of a carrier generating region 11, a carrier selective transfer region 12, and a light emitting region 13 has been omitted. In FIG. 1 B, an upper region of the diagram indicates a higher energy of an electron, and a lower region of the diagram indicates a higher energy of a hole. Also, in FIG. 1 B, the closed circles (•) represent electrons, and the open circles (○) represent holes. In FIG. 1 B, E1 is the energy gap of a semiconductor material included in a wavelength converting region 10. E2 is the energy of monochromatic light generated in the wavelength converting region 10, and E3 is the energy gap of a semiconductor material included in a photoelectric conversion region 20. In FIGS. 1 A and 1 B, sunlight travels from the left side to the right side in the diagram.

Figure 1B:
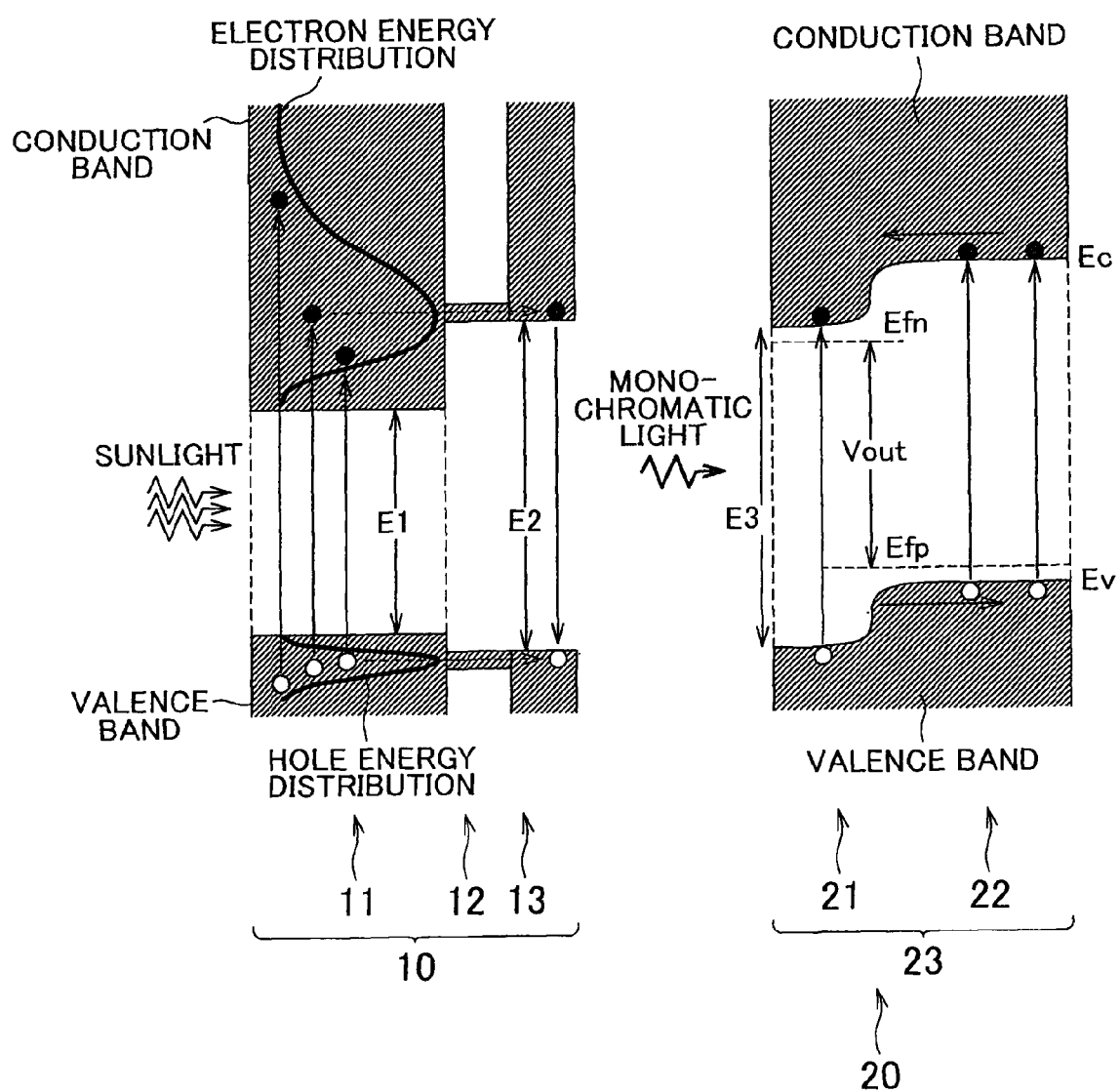
FIG. 1B is a diagram showing the band structure for the solar cell in FIG. 1A.

As shown in FIGS. 1A and 1B, a solar cell 100 is provided with a wavelength converting region 10 containing a semiconductor material and a photoelectric conversion region 20 containing a semiconductor material. The wavelength converting region 10 is disposed on an upstream side of the photoelectric conversion region 20 in the traveling direction of the sunlight. The solar cell 100 is a down-conversion solar cell. The wavelength converting region 10 has a carrier generating region 11 composed of a semiconductor material having an energy gap E1, a light emitting region 13 composed of a semiconductor material having an energy gap E2, and a carrier selective transfer region 12 that selectively transfers electrons and holes having an energy difference E2 to the light emitting region 13. The light emitting region 13 has the function of generating monochromatic light having energy E2 by the combination of electrons and holes having an energy difference E2. The photoelectric conversion region 20 contains a semiconductor material having an energy gap E3. The photoelectric conversion region 20 has an n layer 21 composed of an n-type semiconductor for which the energy gap is E3 and a p layer 22 composed of a p-type semiconductor for which the energy gap is E3; joining the n layer 21 with the p layer 22 results in the formation of a p-n junction 23. A surface electrode 24 is connected to the n layer 21, and a back electrode 25 is connected to the p layer 22.

The sunlight that falls on the solar cell 100 enters the wavelength converting region 10. Light having various energies is included in sunlight. When sunlight enters the carrier generating region 11, only light having an energy at or greater than energy E1 is absorbed by the carrier generating region 11. When light is thus absorbed, electrons having various energies are excited from the valence band to the conduction band, and holes having various energies are formed in the valence band. That is, when light enters the carrier generating region 11, an electron energy distribution like that shown in FIG. 1B forms in the conduction band of the semiconductor material making up the carrier generating region 11, and a hole energy distribution like that shown in FIG. 1B forms in the valence band of the semiconductor material.

As shown in FIG. 1B, the carrier selective transfer region 12 is a region that connects the carrier generating region 11 with the light emitting region 13, and that has the function of selectively transferring to the light emitting region 13, from among the electrons and holes having various energies that are generated in the carrier generating region 11, only those electrons having specific energies and those holes having specific energies that result in an energy difference of E2. Such a function in the carrier selective transfer region 12 can be achieved by using, for example, a quantum well structure. The electrons and holes that have moved from the carrier generating region 11 to the light emitting region 13 through the carrier selective transfer region 12 combine at the light emitting region 13. By means of such a process, the wavelength converting region 10 generates monochromatic light having energy E2.

Of the electrons and holes generated in the carrier generating region 11, those electrons and holes having specific energies, at which the electrons and holes can be transferred through the carrier selective transfer region 12 (sometimes referred to below as "the specific energies for contribution to light emission") pass unchanged through the carrier selective transfer region 12 and reach the light emitting region 13. By combining at the light emitting region 13, these carriers generate monochromatic light having energy E2. By contrast, in the electron distribution in the conduction band of the carrier generating region 11, those electrons having energies that differ from the specific energies for contribution to light emission carry out energy transfer therebetween, yielding some electrons having the specific energies for contribution to light emission. Similarly, in the hole distribution in the valence band of the carrier generating region 11, holes having energies that differ from the specific energies for contribution to light emission carry out energy transfer therebetween, yielding some holes having the specific energies for contribution to light emission. In this way, the electrons that have come to have the specific energies for contribution to light emission and the holes that have come to have the specific energies for contribution to light emission are able to move through the carrier selective transfer region 12 to the light emitting region 13 and, by combining at the light emitting region 13, generate monochromatic light having energy E2. Here, in conventional down-conversion solar cells that use a fluorescent material, the electrons and holes that are capable of interacting have been limited to electrons and holes having separated energy levels. By contrast, because the carrier generating region 11 is composed of a semiconductor material, it is possible, through interactions between electrons and between holes having various energies, to generate electrons having the specific energies for contribution to light emission and holes having the specific energies for contribution to light emission. The monochromatic light that is generated in this way at the light emitting region 13 then travels toward the photoelectric conversion region 20.

The photoelectric conversion region 20 has an n layer 21 and a p layer 22, each with an energy gap of E3. Here, E3 is about 0.1 eV smaller than E2. As a result, monochromatic light having energy E2 generated at the wavelength converting region 10 is absorbed by the photoelectric conversion region 20, creating electrons and holes. Owing to the small difference between E2 and E3 of about 0.1 eV, with substantially no loss of energy, the electrons and holes thus generated are separated by an internal electrical field that is formed by the p-n junction 23. The electrons then move to the n layer 21 side and are collected at the surface electrode 24 connected to the n layer 21. The holes move to the p layer 22 side and are collected at the back electrode 25 connected to the p layer 22.

Thus, within the solar cell 100, the carriers generated at the carrier generating region 11 are transferred via the carrier selective transfer region 12 to the light emitting region 13, and generate monochromatic light at the light emitting region 13. Because it becomes possible, with such an embodiment, to induce the electrons and holes that are excited to high energies in the carrier generating region 11 to move to the light emitting region 13 and combine before the energy is lost, energy loss can be reduced. A purpose of the wavelength converting region 10 is to allow the charge carriers that are generated in the carrier generating region 11 to recombine at the light emitting region 13; it is not intended to extract the generated carriers directly to the exterior. Accordingly, in the wavelength converting region 10, unlike in conventional hot carrier solar cells, there is no need to have the carriers move all the way to the electrode, so that it is made possible to markedly reduce the energy loss during movement. In particular, by controlling the size and thickness of the carrier generating region 11, and thereby setting the movement length of carriers from the generation in the carrier generating region 11 until they reach the carrier selective transfer region 12 to about 10 nm or less, it becomes possible to greatly reduce energy loss during movement. Moreover, by using a semiconductor material in the carrier generating region 11, it becomes possible to considerably broaden the wavelength range of light that can be utilized for generating carriers as compared to conventional down-conversion solar cells that use fluorescent materials. Furthermore, in the solar cell 100 wherein the monochromatic light generated at the wavelength converting region 10 is input to the photoelectric conversion region 20, the energy of the monochromatic light input to the photoelectric conversion region 20 is fixed at E2. The energy loss is thus easily reduced by using in the photoelectric conversion region 20 a semiconductor material having an energy gap corresponding to E2. Accordingly, with the invention, it is possible to provide a solar cell 100, with which it is possible to increase the photoelectric conversion efficiency. In the solar cell 100, the photoelectric conversion efficiency is easily increased by increasing the efficiency of the wavelength converting region 10 that converts light to monochromatic light.

In the solar cell 100, the energy gap E1 of the semiconductor material making up the carrier generating region 11 may be set to, for example, at least 0.4 eV and not more than 1.2 eV. In cases where the movement length of the carriers generated in the carrier generating region 11 is set to 10 nm or less, due to quantum effects, the energy gap of the carrier generating region 11 becomes larger than the energy gap of the bulk material. Examples of the semiconductor material of which the carrier generating region 11 may be composed include PbSe, InAs, PbS, Ge, GaSb, GaAsSb, GaInAs and Si. In cases where the carrier generating region 11 is composed of a group IV element such as Ge or Si or a group III-V compound such as InAs, GaSb, GaAsSb or GaInAs, the carrier generating region 11 may be fabricated by a vapor phase growth process such as metal organic chemical vapor deposition (MOCVD) or molecular beam epitaxy (MBE). Alternatively, in cases where the carrier generating region 11 is composed of a group IV-VI compound such as PbSe or PbS, the carrier generating region 11 may be fabricated by a vacuum deposition process that includes ion plating, by a vapor phase growth process such as sputtering, or by chemical synthesis such as a sol-gel process or solvothermal synthesis.

If the carrier selective transfer region 12 is given a quantum well structure, the thickness of the quantum well layer may be set to, for example, at least 2 nm and not more than 10 nm, and the energy gap of the semiconductor material making up the quantum well layer may be set to, for example, at least 0.6 eV and not more than 1.6 eV. Examples of the semiconductor material of which the quantum well layer may be composed include Ge, GaSb, InPAs, GaAsSb, GaInAs, Si, InP, GaAs, CdTe, CdSe, AlGaAs, GaInP, AlAs, ZnTe, GaP, CdS and ZnSe. In cases where the quantum well layer is composed of a IV group element such as Ge or Si, or a group III-V compound such as GaSb, GaAsSb, GaInAs, InP, GaAs, AlGaAs, GaInP, AlAs or GaP, the quantum well layer may be fabricated by a vapor phase growth process such as MOCVD or MBE. Alternatively, in cases where the quantum well layer is composed of a group II-VI compound such as CdTe, CdSe, ZnTe, CdS or ZnSe, the quantum well layer may be fabricated by a vacuum deposition process that includes ion plating, by a vapor phase growth process such as sputtering, or by chemical synthesis such as a sol-gel process or solvothermal synthesis.

If the carrier selective transfer region 12 is given a quantum well structure, the thickness of barrier layers on either side of the quantum well layer may be set to, for example, at least 2 nm and not more than 10 nm; and the energy gap of the semiconductor material making up the barrier layers may be set to, for example, at least 1.2 eV and not more than 4.0 eV. Examples of the semiconductor material of which the barrier layers may be composed include InP, GaAs, CdTe, CdSe, AlGaAs, GaInP, AlAs, ZnTe, GaP, CdS, ZnSe, GaN and ZnS. In cases where the barrier layers are composed of a group III-V compound such as InP, GaAs, AlGaAs, GaInP, AlAs, GaP or GaN, the barrier layers may be fabricated by a vapor phase growth process such as MOCVD or MBE. Alternatively, in cases where the barrier layers are composed of a group II-VI compound such as CdTe, CdSe, ZnTe, CdS, ZnSe or ZnS, the barrier layers may be fabricated by a vacuum deposition process that includes ion plating, by a vapor phase growth process such as sputtering, or by chemical synthesis such as a sol-gel process or solvothermal synthesis.

The energy E2 of the monochromatic light generated at the light emitting region 13 may be set to, for example, at least 0.6 eV and not more than 1.6 eV. The thickness of the light emitting region 13 may be set to at least 2 nm and not more than 20 nm. Examples of the semiconductor material of which the light emitting region 13 may be composed include Ge, GaSb, InPAs, GaAsSb, GaInAs, Si, InP, GaAs, CdTe, CdSe, AlGaAs, GaInP, AlAs, ZnTe, GaP, CdS and ZnSe. In cases where the light emitting region 13 is composed of a group IV element such as Ge or Si, or a group III-V compound such as GaSb, GaAsSb, GaInAs, InP, GaAs, AlGaAs, GaInP, AlAs or GaP, the light emitting region 13 may be fabricated by a vapor phase growth process such as MOCVD or MBE. Alternatively, in cases where the light emitting region 13 is composed of a group II-VI compound such as CdTe, CdSe, ZnTe, CdS or ZnSe, the light emitting region 13 may be fabricated by a vacuum deposition process that includes ion plating, by a vapor phase growth process such as sputtering, or by chemical synthesis such as a sol-gel process or solvothermal synthesis.

The energy gap E3 of the semiconductor material included in the photoelectric conversion region 20 may be set to, for example, at least 0.5 eV and not more than 1.6 eV. Examples of the semiconductor material of which the photoelectric conversion region 20 may be composed include Ge, GaSb, GaAsSb, GaInAs, Si, InP, GaAs and CdTe. In the photoelectric conversion region 20, the n layer 21 may be fabricated by adding an available n-type dopant to these semiconductor materials, and the p layer 22 may be fabricated by adding an available p-type dopant to these semiconductor materials. The thickness of the n layer 21 may be set to, for example, about 100 nm, and the thickness of the p layer 22 may be set to, for example, about 2 μm. In cases where the photoelectric conversion region 20 is made of a group IV element such as Ge or Si, or a group III-V compound such as GaSb, GaAsSb, GaInAs, InP or GaAs, the photoelectric conversion region 20 may be fabricated by a vapor phase growth process such as MOCVD or MBE. Alternatively, in cases where the photoelectric conversion region 20 is composed of a group II-VI compound such as CdTe, the photoelectric conversion region 20 may be fabricated by a vacuum deposition process that includes ion plating, by a vapor phase growth process such as sputtering, or by chemical synthesis such as a sol-gel process or solvothermal synthesis. The surface electrode 24 and the back electrode 25 may be fabricated by a conventional method such as a vapor deposition process. An available material that can be employed as a solar cell electrode, examples of which include comb-shaped metallic materials such as Al, Ag and Au, and transparent electrically conductive films such as indium-tin oxide (ITO), aluminum-doped zinc oxide (AZO) and fluorine-doped tin oxide (FTO), may be suitably used for the surface electrode 24. An available material that can be employed as a solar cell electrode, examples of which include Al, Ag and Au, may be suitably used for the back electrode 25. The thicknesses of the surface electrode 24 and the back electrode 25 may be set to, for example, about 1 to 10 μm in the case of a metal material, and about 0.1 to 1 μm in the case of a transparent electrically conductive film.

In the foregoing explanation of the solar cell 100, an embodiment was described in which the photoelectric conversion region 20 has a p-n junction. However, the photoelectric conversion device according to the first embodiment of the invention (a down-conversion type photoelectric conversion device; the same applies below) is not limited to this form. The photoelectric conversion region provided in the photoelectric conversion device according to the first embodiment of the invention may have a p-i-n junction.

Also, in the foregoing explanation of the solar cell 100, an embodiment has been described in which the junction interface between the n layer 21 and the p layer 22 is planar. However, the photoelectric conversion device according to the first embodiment of the invention is not limited to this form. The photoelectric conversion region provided in the photoelectric conversion device according to the first embodiment of the invention, as is subsequently described, may have a junction interface with surface irregularities (a three-dimensionally joined region) as in the manner of a bulk heterostructure.

Figure 2A:
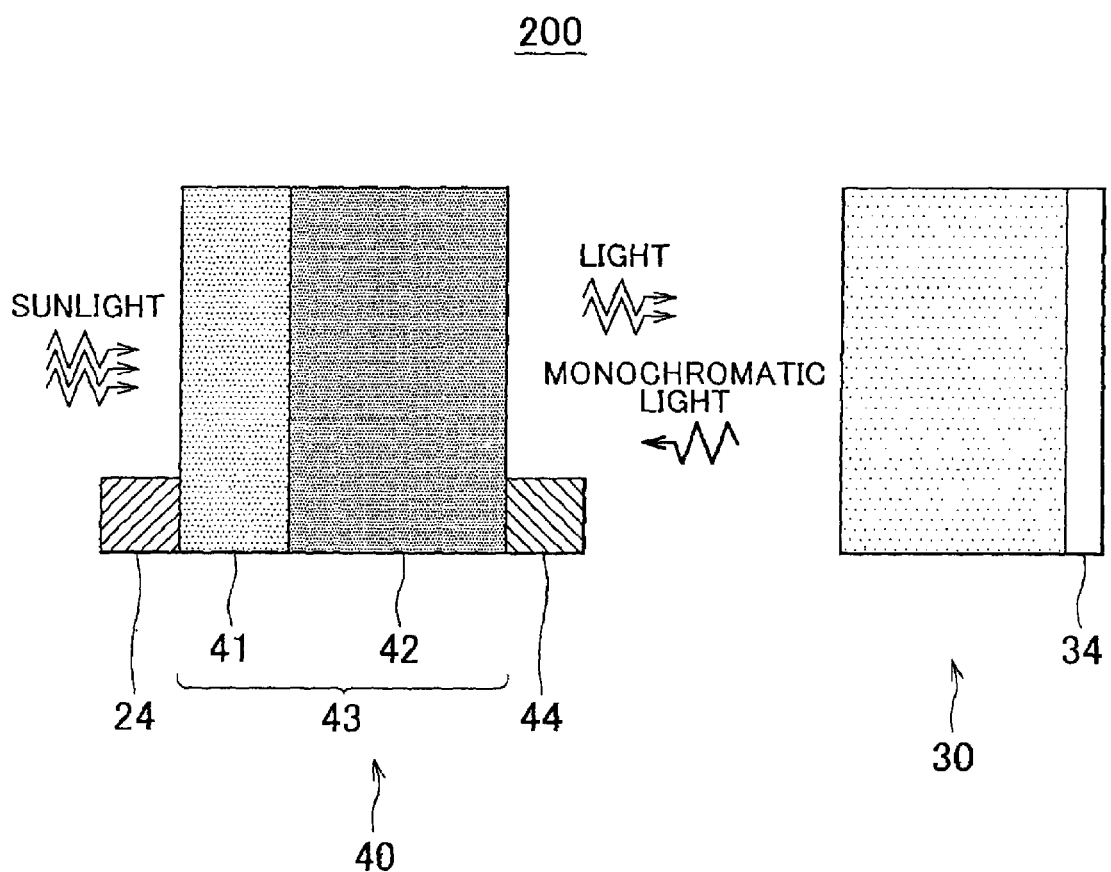
FIG. 2A is a sectional view of a solar cell according to a second embodiment of the invention.
Figure 2B:
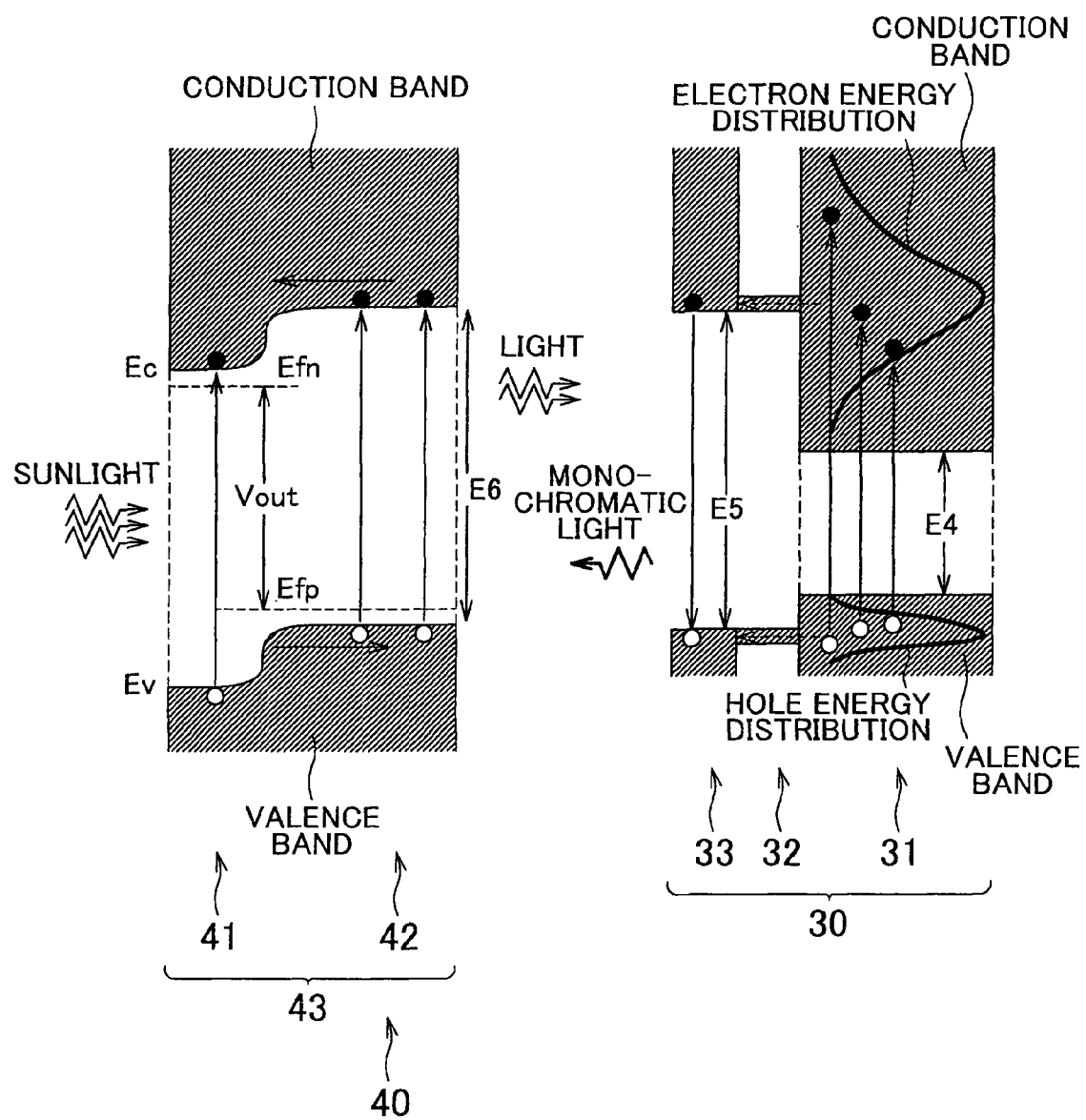
FIG. 2B is a diagram showing the band structure for the solar cell in FIG. 2A.

FIG. 2A is a sectional view showing a solar cell 200 according to a second embodiment of the invention, and FIG. 2B is a diagram illustrating the band structure of the solar cell 200. In FIG. 2A, description of a carrier generating region 31, a earner selective transfer region 32 and a light emitting region 33 has been omitted. In FIG. 2B, an upper region of the diagram indicates a higher energy of an electron, and a lower region of the diagram indicates a higher energy of a hole. Also, in FIG. 2B, the closed circles (•) represent electrons, and the open circles (○) represent holes. In FIG. 2B, E4 is the energy gap of a semiconductor material included in a wavelength converting region 30, E5 is the energy of monochromatic light generated in the wavelength converting region 30, and E6 is the energy gap of a semiconductor material included in a photoelectric conversion region 40. In FIGS. 2A and 2B, sunlight travels from the left side to the right side in the diagram. In FIG. 2A, elements similar to those in the above-described solar cell 100 are denoted by the same symbols as are used in FIG. 1A, and explanations of those elements are omitted below as appropriate.

As shown in FIGS. 2A and 2B, a solar cell 200 has a wavelength converting region 30 containing a semiconductor material and a photoelectric conversion region 40 containing a semiconductor material. The wavelength converting region 30 is disposed on the downstream side of the photoelectric conversion region 40 in the direction in which the sunlight travels. The solar cell 200 is an up-conversion solar cell. The wavelength converting region 30 has a carrier generating region 31 composed of a semiconductor material with an energy gap E4, a light emitting region 33 composed of a semiconductor material with an energy gap E5, a carrier selective transfer region 32 that selectively transfers electrons and holes having an energy difference E5 to the light emitting region 33, and a light reflecting region 34 that reflects the monochromatic light generated in the light emitting region 33 to the photoelectric conversion region 40 side. The light emitting region 33 has the function of generating monochromatic light having energy E5 by the combination of electrons and holes having the energy difference E5. The photoelectric conversion region 40 contains a semiconductor material having the energy gap E6. The photoelectric conversion region 40 has an n layer 41 composed of an n-type semiconductor for which the energy gap is E6 and a p layer 42 composed of a p-type semiconductor for which the energy gap is E6; joining the n layer 41 with the p layer 42 results in the formation of a p-n junction 43. A surface electrode 24 is connected to the n layer 41, and a back electrode 44 is connected to the p layer 42.

Sunlight that falls on the solar cell 200 enters the photoelectric converting region 40. The energy gap E6 of the semiconductor material included in the photoelectric conversion region 40 is adjusted so as to be capable of absorbing, of the sunlight that contains light having various energies, only high-energy light. As a result, when sunlight enters the semiconductor material included in the photoelectric conversion region 40, only that light having an energy equal to or greater than the energy gap E6 of this semiconductor material is absorbed. When light is absorbed in this way, electrons and holes are generated in the photoelectric conversion region 40. The generated electrons and holes are separated by an internal electrical field that is formed by the n layer 41 and the p layer 42. The electrons move to the n-layer 41 side and are collected at the surface electrode 24 connected to the n layer 41. The holes move to the p layer 42 side and are collected at the back electrode 44 connected to the p layer 42.

As described above, in the photoelectric conversion region 40, only that light included in the sunlight that has an energy equal to or greater than E6 is absorbed. Therefore, of the light included in sunlight, light having an energy that is less than E6 passes through the photoelectric conversion region 40 without being utilized in photoelectric conversion. The light that passes through the photoelectric conversion region 40 in this way enters the wavelength converting region 30 that is disposed on the downstream side in the direction in which the sunlight travels. The energy gap E4 of the semiconductor material making up the carrier generating region 31 of the wavelength converting region 30 is smaller than E6 and is adjusted so as to be capable of absorbing low-energy light included in the sunlight. As a result, when light enters the carrier generating region 31 of the wavelength-converting region 30, only that light having an energy equal to or greater than the energy gap E4 of the semiconductor material making up the carrier generating region 31 is absorbed. When light is thus absorbed, electrons having various energies are excited from the valence band to the conduction band, and holes having various energies form in the valence band. That is, when light enters the carrier generating region 31, an electron energy distribution like that shown in FIG. 2B forms in the conduction band of the semiconductor material making up the carrier generating region 31, and a hole energy distribution like that shown in FIG. 2B forms in the valence band of this semiconductor material.

As shown in FIG. 2B, the carrier selective transfer region 32 is a region that connects the carrier generating region 31 with the light emitting region 33, and has the function of selectively transferring to the light emitting region 33, from among the electrons and holes having various energies that are generated at the carrier generating region 31, only those electrons having specific energies and those holes having specific energies that result in an energy difference of E5. Such a function of the carrier selective transfer region 32 can be achieved by the use of, for example, a quantum well structure. The electrons and holes that are transferred from the carrier generating region 31 to the light emitting region 33 via the carrier selective transfer region 32 combine at the light emitting region 33. By passing through such a process, the wavelength converting region 30 generates monochromatic light having energy E5.

Here, in conventional up-conversion solar cells that use fluorescent materials, the electrons and holes capable of interacting have been limited to electrons and holes having separated energy levels. By contrast, because the carrier generating region 31 is composed of a semiconductor material, electrons having various energies are able to mutually interact and holes having various energies are able to mutually interact. By allowing electrons and holes having an energy difference E5 that have passed through the carrier selective transfer region 32 to recombine in the light emitting region 33, monochromatic light having the energy E5 can be generated. At least part of the monochromatic light thus generated in the light emitting region 33 is reflected by the light reflecting region 34 and travels toward the photoelectric conversion region 40.

The photoelectric conversion region 40 has an n layer 41 and a p layer 42, each of which has an energy gap of E6. Here, E6 is about 0.1 eV smaller than E5. As a result, monochromatic light having energy E5 generated in the light emitting region 33 is absorbed by the photoelectric conversion region 40, creating electrons and holes. The electrons and holes thus generated, owing to the small difference between E5 and E6 of about 0.1 eV are separated by the internal electrical field that is formed by the p-n junction 43 with substantially no loss of energy. The electrons move to the n layer 41 side and are collected at the surface electrode 24 connected to the n layer 41, and the holes move to the p layer 42 side and are collected at the back electrode 44 connected to the p layer 42.

With such a solar cell 200, the sunlight having an energy greater than the energy gap E6 of the semiconductor material included in the photoelectric conversion region 40 can be absorbed at the photoelectric conversion region 40 and converted into electricity. In addition, monochromatic light generated at the light emitting region 33 using the light that is not converted into electricity in the photoelectric conversion region 40 can be converted into electricity by being input to the photoelectric conversion region 40. By employing such an embodiment, it becomes possible to greatly expand the wavelength range of light utilized during conversion to electricity in the photoelectric conversion region 40. A purpose of the wavelength converting region 30 is to allow the carriers that are generated in the carrier generating region 31 to recombine at the light emitting region 33; it is not intended to extract the carriers directly to the exterior. Hence, in the wavelength converting region 30, unlike in conventional hot carrier solar cells in which a quantum structure is used, there is no need to have the carriers move all the way to the electrodes, so that it is made possible to markedly reduce the energy loss during movement. In particular, by controlling the size and thickness of the carrier generating region 31, and thereby setting the movement length of carriers from the generation in the carrier generating region 31 until the carriers reach the carrier selective transfer region 32 to about 10 nm or less, it becomes possible to greatly reduce energy loss during movement. Moreover, by using a semiconductor material in the carrier generating region 31, it becomes possible to considerably broaden the wavelength range of light that can be utilized for generating carriers as compared to conventional up-conversion solar cells that use fluorescent materials. In addition, in the solar cell 200 in which the monochromatic light generated at the wavelength converting region 30 is input to the photoelectric conversion region 40, the energy of the monochromatic light input to the photoelectric conversion region 40 is fixed at E5.

The energy loss is thus easily reduced by using in the photoelectric conversion region 40 a semiconductor material having an energy gap corresponding to E5. Accordingly, with the invention, it is possible to provide a solar cell 200, with which it is possible to increase the photoelectric conversion efficiency. In the solar cell 200, the photoelectric conversion efficiency is easily increased by increasing the efficiency of the wavelength converting region 30 that converts light to monochromatic light.

In the solar cell 200, the energy gap E4 of the semiconductor material making up the carrier generating region 31 may be set to, for example, at least 0.4 eV and not more than 1.6 eV. In cases where the movement length of the carriers generated in the carrier generating region 31 is set to 10 nm or less, due to quantum effects, the energy gap of the carrier generating region 31 becomes larger than the energy gap of the bulk material. Examples of semiconductor materials of which the carrier generating region 31 may be made include PbSe, InAs, PbS, Ge, GaSb, GaAsSb, GaInAs, Si, InP, GaAs and CdTe. In cases where the carrier generating region 31 is composed of a group IV element such as Ge or Si or a group III-V compound such as InAs, GaSb, GaAsSb, GaInAs, InP or GaAs, the carrier generating region 31 may be fabricated by a vapor phase growth process such as MOCVD or MBE. Alternatively, in cases where the carrier generating region 31 is composed of a group IV-VI compound such as PbSe or PbS or a group II-VI compound such as CdTe, the carrier generating region 31 may be fabricated by a vacuum deposition process that includes ion plating, by a vapor phase growth process such as sputtering, or by chemical synthesis such as a sol-gel process or solvothermal synthesis.

In cases where the carrier selective transfer region 32 is given a quantum well structure, the thickness of the quantum well layer may be set to, for example, at least 2 nm and not more than 10 nm; and the energy gap of the semiconductor material making up the quantum well layer may be set to, for example, at least 1.0 eV and not more than 3.0 eV. Examples of the semiconductor materials of which the quantum well layer may be composed are similar to those of the semiconductor materials of which the quantum well layer of the above-described carrier selective transfer region 12 may be composed. The quantum well layer of the carrier selective transfer region 32 may be fabricated by methods similar to those for the quantum well layer of the above-described carrier selective transfer region 12.

If the carrier selective transfer region 32 is given a quantum well structure, the thickness of the barrier layers on either side of the quantum well layer may be set to, for example, at least 2 nm and not more than 10 nm; and the energy gap of the semiconductor material making up the barrier layers may be set to, for example, at least 1.2 eV and not more than 4.0 eV. Examples of semiconductor materials of which the barrier layers may be composed are similar to those of the semiconductor materials of which the barrier layers of the above-described carrier selective transfer region 12 may be composed. The barrier layers of the carrier selective transfer region 32 may be fabricated by methods similar to those for the barrier layers of the above-described carrier selective transfer region 12.

The energy E5 of the monochromatic light generated at the light emitting region 33 may be set to, for example, at least 1.0 eV and not more than 3.0 eV. The thickness, constituent materials and method of fabrication for the light emitting region 33 may be made the same as the thickness, constituent materials and method of fabrication for the above-described light emitting region 13.

The light reflecting region 34 may be composed of a metal or the like, such as Ag or Al, having a high reflectance for visible light to infrared light. The thickness of the light reflecting region 34 may be set to, for example, about 1 μm, and the light reflecting region 34 may be fabricated by a conventional method such as a vapor deposition process.

The energy gap E6 of the semiconductor material included in the photoelectric conversion region 40 may be set to, for example, at least 0.9 eV and not more than 3.0 eV. Examples of semiconductor materials of which the photoelectric conversion region 40 may be composed include GaAsSb, GaInAs, Si, InP, GaAs, CdTe, CdSe, AlGaAs, GaInP, AlAs, ZnTe, GaP, CdS and ZnSe. In the photoelectric conversion region 40, the n layer 41 may be fabricated by adding an available n-type dopant to these semiconductor materials, and the p layer 42 may be fabricated by adding an available p-type dopant to these semiconductor materials. The thickness of the n layer 41 may be set to, for example, about 100 nm, and the thickness of the p layer 42 may be set to, for example, about 2 μm. In cases where the photoelectric conversion region 40 is made of a group IV element such as Si or a group III-V compound such as GaAsSb, GaInAs, InP, GaAs, AlGaAs, GaInP, AlAs or GaP, the photoelectric conversion region 40 may be fabricated by a vapor phase growth process such as MOCVD or MBE. Alternatively, in cases where the photoelectric conversion region 40 is composed of a group II-VI compound such as CdTe, CdSe, ZnTe, CdS or ZnSe, the photoelectric conversion region 40 may be fabricated by a vacuum deposition process that includes ion plating, by a vapor phase growth process such as sputtering, or by chemical synthesis such as a sol-gel process or solvothermal synthesis. An available material that can be employed as a solar cell electrode, examples of which include comb-shaped metallic materials such as Al, Ag and Au, and transparent electrically conductive films such as indium-tin oxide (ITO), aluminum-doped zinc oxide (AZO) and fluorine-doped tin oxide (FTO), may be suitably used for the back electrode 44. The thickness of the back electrode 44 may be set to about 1 to 10 μm in the case of a metal material, and to about 0.1 to 1 μm in the case of a transparent electrically conductive film. The back electrode 44 may be fabricated by a conventional method such as a vapor deposition process.

In the foregoing explanation of the solar cell 200, an embodiment has been described in which the photoelectric conversion region 40 has a p-n junction. However, the photoelectric conversion device according to the second embodiment of the invention (an up-conversion type photoelectric conversion device; the same applies below) is not limited to this form. The photoelectric conversion region provided in the photoelectric conversion device according to the second embodiment of the invention may have a p-i-n junction.

Also, in the foregoing explanation of the solar cell 200, an embodiment was described in which the junction interface between the n layer 41 and the p layer 42 is planar. However, the photoelectric conversion device according to the second embodiment of the invention is not limited to this form. The photoelectric conversion region provided in the photoelectric conversion device according to the second embodiment of the invention may, as subsequently described, have a junction interface with surface irregularities (a three-dimensionally joined region) as in the manner of a bulk heterostructure.

Also, in the above explanations of solar cells 100 and 200, embodiments of the invention has been described in which the wavelength converting region is disposed on only one side of the photoelectric conversion region. However, in the photoelectric conversion device of the invention, it is also possible to dispose wavelength converting regions in such a way that the photoelectric conversion region is sandwiched between a pair of wavelength converting regions.

A solar cell 100 in which a wavelength converting region 10 is disposed at a distance from a photoelectric conversion region 20, and a solar cell 200 in which a wavelength converting region 30 is disposed at a distance from a photoelectric conversion region 40 have been described above and illustrated in the diagrams. However, the photoelectric conversion device according to the first embodiment of the invention and the photoelectric conversion device according to the second embodiment of the invention are not limited to these forms. The photoelectric conversion device according to the first embodiment of the invention and the photoelectric conversion device according to the second embodiment of the invention may be disposed so as to bring the wavelength converting region and the photoelectric conversion region into mutual contact. In cases where the wavelength converting region and the photoelectric conversion region are disposed so as to not be in mutual contact, it suffices that a substance that allows light to pass through is placed between the wavelength converting region and the photoelectric conversion region. Examples of such a material include air, a clear plastic film or glass, etc. In cases where the wavelength converting region and the photoelectric conversion region are disposed so as not to be in mutual contact, the wavelength converting region is held stationary by fixing means (not shown). Conventional fixing means that can be used to hold the wavelength-converting region may be used as the fixing means.

In the above description, a solar cell 100 in which the surface of the wavelength converting region 10 on the photoelectric conversion region 20 side thereof is a smooth surface and a solar cell 200 in which the surface of the wavelength converting region 30 on the photoelectric conversion region 40 side thereof is a smooth surface have been depicted. However, the photoelectric conversion device according to the first embodiment of the invention and the photoelectric conversion device according to the second embodiment of the invention are not limited to these forms. In the photoelectric conversion device according to the first embodiment of the invention and the photoelectric conversion device according to the second embodiment of the invention, in order to, for example, provide an embodiment wherein the monochromatic light generated in the light emitting region is readily input to the photoelectric conversion region, it is preferable to provide surface irregularities on at least the surface of the wavelength converting region on the photoelectric conversion region side thereof in cases where the wavelength converting region and the photoelectric conversion region are not in contact with each other, and it is preferable to provide surface irregularities at the interface between the wavelength converting region and the photoelectric conversion region in cases where the wavelength converting region and the photoelectric conversion region are in contact with each other, By providing surface irregularities, it is possible reduce the proportion of the monochromatic light generated at the wavelength converting region that is reflected at the surface of the wavelength converting region on the photoelectric conversion region side thereof.

Figure 3:
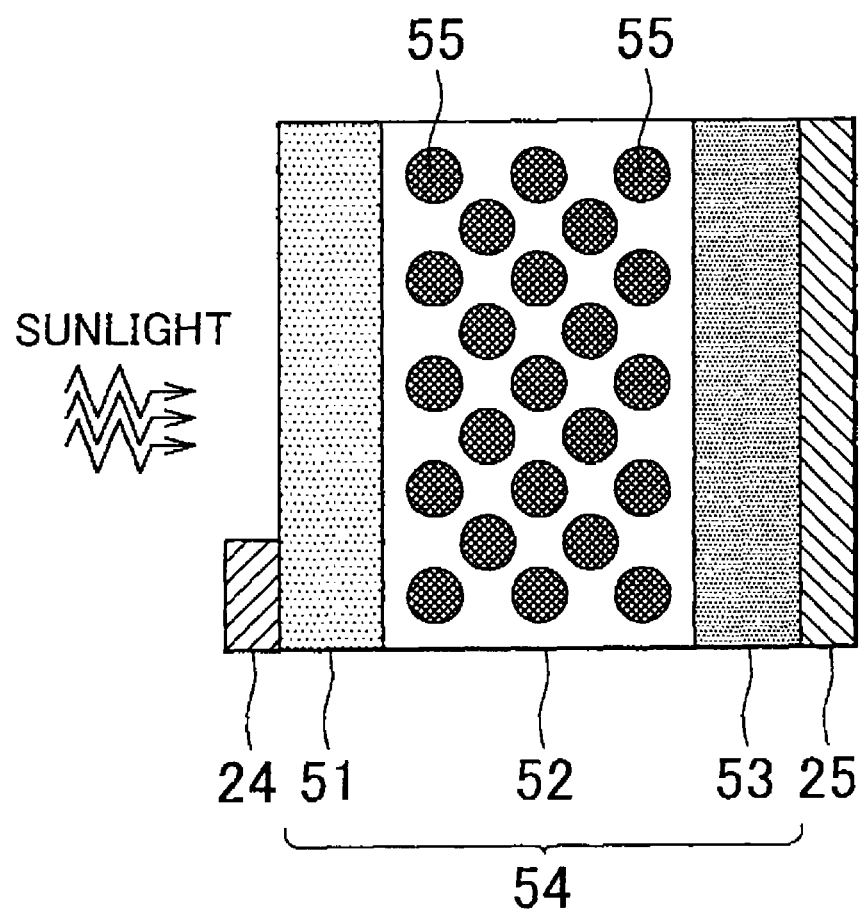
FIG. 3 is a sectional view of a solar cell according to a third embodiment of the invention.

FIG. 3 is a sectional view showing a solar cell 300 according to a third embodiment of the invention. In FIG. 3, elements similar to those in the above-described solar cell 100 are denoted by the same symbols as are used in FIG. 1A, and explanations of those elements are omitted below as appropriate. In FIG. 3, description of a carrier generating region, a carrier selective transfer region and a light emitting region has been omitted.

As shown in FIG. 3, a solar cell 300 has an n layer 51, an i layer 52 and a p layer 53. The n layer 51, i layer 52 and p layer 53 together form a p-i-n junction 54. In the solar cell 300, the i layer 52 functions primarily as a photoelectric conversion region, and a plurality of wavelength converting regions 55 containing a semiconductor material are dispersed within the i layer 52. In the solar cell 300, light that has passed through a portion of the i layer 52 enters the wavelength converting regions 55. The solar cell 300 is an up-conversion solar cell. Each of the wavelength converting regions 55 includes a carrier generating region composed of a semiconductor material having an energy gap E4, a light emitting region composed of a semiconductor material having an energy gap E5, and a carrier selective transfer region that selectively transfers electrons and holes generated in the carrier generating region and having an energy difference E5 to the light emitting region. The light emitting region has the function of generating monochromatic light having energy E5 by recombining the electrons and holes having the energy difference E5. The i layer 52 that functions as a photoelectric conversion region is composed of a semiconductor material having an energy gap E6 (E5−E6≅0.1 eV). The n layer 51, to which a surface electrode 24 is connected, is composed of an n-type semiconductor having an energy gap E6. The p layer 53, to which a back electrode 25 is connected, is composed of a p-type semiconductor having an energy gap E6.

The sunlight that falls on the solar cell 300 passes through the n layer 51 and enters, of the i layer 52, the semiconductor material disposed around the wavelength converting regions 55 (sometimes referred to below as "the photoelectric conversion region 52"). The energy gap E6 of this photoelectric conversion region 52 is adjusted so as to be capable of absorbing, from the sunlight that includes light having various energies, only high-energy light. As a result, when sunlight enters the photoelectric conversion region 52, only that light having an energy equal to or greater than the energy gap E6 of this photoelectric conversion region 52 is absorbed. When light is absorbed in this way, electrons and holes are generated in the photoelectric conversion region 52. The generated electrons and holes are separated by an internal electrical field that is formed by the n layer 51 and the p layer 53. The electrons move to the n layer 51 side and are collected at the surface electrode 24 connected to the n layer 51. The holes move to the p layer 53 side and are collected at the back electrode 25 connected to the p layer 53.

As described above, in the photoelectric conversion region 52, only that light included within the sunlight that has an energy equal to or greater than E6 is absorbed. Therefore, of the light included in sunlight, light having an energy less than E6 passes through the photoelectric conversion region 52 without being utilized in photoelectric conversion, and reaches the wavelength converting regions 55. The energy gap E4 of the semiconductor material making up the carrier generating region of the wavelength converting region 55 is smaller than E6 and is adjusted so as to be capable of absorbing low-energy light included in sunlight. As a result, when light enters the carrier generating regions of the wavelength converting regions 55, only that light having an energy equal to or greater than the energy gap E4 of the semiconductor material making up the carrier generating regions is absorbed. When light is thus absorbed, electrons having various energies are excited from the valence band to the conduction band, and holes having various energies form in the valence band. That is, when light enters the carrier generating regions of the wavelength converting regions 55, as in the case of the carrier generating region 31 of the solar cell 200 described above, an electron energy distribution like that shown in FIG. 2B forms in the conduction band of this semiconductor material and a hole energy distribution like that shown in FIG. 2B forms in the valence band of this semiconductor material.

The electrons and holes generated in the carrier generating regions of the wavelength converting regions 55 carry out energy transfer through mutual interactions between the electrons and mutual interactions between the holes. Electrons having specific energies and holes having specific energies such that the energy difference therebetween becomes E5 pass through the carrier selective transfer regions of the wavelength converting regions 55 and reach the light emitting regions of the wavelength converting regions 55. The carrier selective transfer region's function of selectively transferring to the light emitting region only those electrons having specific energies and only those holes having specific energies can be achieved by using a quantum well structure. The electrons and holes that have moved to the light emitting regions of the wavelength converting regions 55 recombine at this light emitting region. Through such a process, the wavelength converting regions 55 generate monochromatic light having energy E5. The monochromatic light thus generated at the wavelength converting regions 55 travels toward the photoelectric conversion region 52.

The energy gap of the photoelectric conversion region 52 is E6. Here, E6 is about 0.1 eV smaller than E5. Therefore, the monochromatic light having energy E5 generated in the wavelength converting regions 55 is absorbed by the photoelectric conversion region 52, resulting in the generation of electrons and holes in the photoelectric conversion region 52. Because of the small difference of about 0.1 eV between E5 and E6, the electrons and holes thus generated are separated, with substantially no loss of energy, by the internal electrical field that is formed by the p-i-n junction 54, and then the electrons move to the n layer 51 side and are collected at the surface electrode 24 connected to the n layer 51, and the holes move to the p layer 53 side and are collected at the back electrode 25 connected to the p layer 53.

Hence, with the solar cell 300, sunlight having an energy greater than the energy gap E6 of the photoelectric conversion region 52 can be absorbed by the photoelectric conversion region 52 and converted into electricity. In addition, monochromatic light generated at the wavelength converting regions 55 using the light that has not been converted into electricity at the photoelectric conversion region 52 can be converted into electricity by being input to the photoelectric conversion region 52. By employing such an embodiment, it becomes possible to greatly expand the wavelength range of light utilized during conversion to electricity at the photoelectric conversion region 52. A purpose of the wavelength converting regions 55 is to allow the carriers that are generated in the carrier-generating region to recombine at the light emitting region; they are not intended to output the generated carriers directly to the exterior. Hence, in the wavelength converting regions 55, unlike in conventional hot carrier solar cells that use a quantum structure, there is no need to have the carriers move all the way to the electrode, so that it is made possible to markedly reduce the energy loss during movement. In particular, by controlling the size and thickness of the carrier generating region in each wavelength converting region 55, and thereby setting the movement length of carriers from the generation in the carrier generating region of the wavelength converting region 55 until they reach the carrier selective transfer region of the wavelength converting region 55 to about 10 nm or less, it becomes possible to greatly reduce energy loss during movement. Moreover, by employing an embodiment in which a semiconductor material is used in the carrier generating region of the wavelength converting region 55, it is possible to considerably broaden the wavelength range of light that can be utilized for generating carriers as compared to conventional up-conversion solar cells that use fluorescent materials. In addition, in a solar cell 300 in which the monochromatic light generated at the wavelength converting regions 55 is input to the photoelectric conversion region 52, the energy of the monochromatic light input to the photoelectric conversion region 52 is fixed at E5. The energy loss is thus easily reduced by using in the photoelectric conversion region 52 a semiconductor material having an energy gap corresponding to E5. Thus, according to the invention, it is possible to provide a solar cell 300 capable of increasing the photoelectric conversion efficiency. In the solar cell 300, the photoelectric conversion efficiency is easily increased by increasing the efficiency of the wavelength converting regions 55 that convert light to monochromatic light.

In the solar cell 300, the energy gap E4 of the semiconductor material making up the carrier generating regions of the wavelength converting regions 55 may be set to, for example, at least 0.4 eV and not more than 1.6 eV. In cases where the movement length of the carriers generated in the carrier generating regions of the wavelength converting regions 55 is set to 10 nm or less, due to quantum effects, the energy gap of the carrier generating region becomes larger than the energy gap of the bulk material. The carrier generating regions of the wavelength converting regions 55 in the present embodiment of the invention may be fabricated using a material and a process similar to those used for the above-described carrier generating region 31.

The carrier selective transfer regions of the wavelength converting regions 55 in the present embodiment of the invention may be fabricated using a material and a process similar to those used for the above-described carrier selective transfer region 32. Also, the light emitting regions of the wavelength converting regions 55 in the present embodiment of the invention may be fabricated using a material and a process similar to those used for the above-described light emitting region 33.

The plurality of wavelength-converting regions 55 constructed in this way are dispersed on the surface of the photoelectric conversion region 52 after a portion of the photoelectric conversion region 52 has been fabricated. Next, by repeatedly carrying out the operation of fabricating a portion of the photoelectric conversion region 52 onto the surfaces of the dispersed wavelength-converting regions 55, the plurality of wavelength-converting regions 55 can be dispersed within the i layer 52.

The energy gap E6 of the n layer 51, the photoelectric conversion region 52 and the p layer 53 may be set to, for example, at least 0.9 eV and not more than 3.0 eV, and materials similar to those used for the above-described photoelectric conversion region 40 may be used for the n layer 51, the photoelectric conversion region 52 and the p layer 53. The thicknesses of the n layer 51 and the p layer 53 may be set to, for example, about 100 nm, and the thickness of the i layer 52 may be set to, for example, about 0.1 to about 1 μm. Moreover, the n layer 51, the photoelectric conversion region 52 and the p layer 53 may be fabricated by methods similar to those used for the above-described photoelectric conversion region 40.

In the above explanation of the solar cell 300, an embodiment in which a plurality of wavelength-converting regions 55 are dispersed only in the i layer 52 has been described. However, the photoelectric conversion device according to the third embodiment of the invention (an up-conversion type photoelectric conversion device; the same applies below) is not limited to this form. In the photoelectric conversion device according to the third embodiment of the invention, wavelength converting regions may be dispersed not only in the i layer, but also in the n layer and/or the p layer.

Embodiments of wavelength converting regions that may be used in the photoelectric conversion devices according to the first to third embodiments of the invention will be described below.

Figure 4:
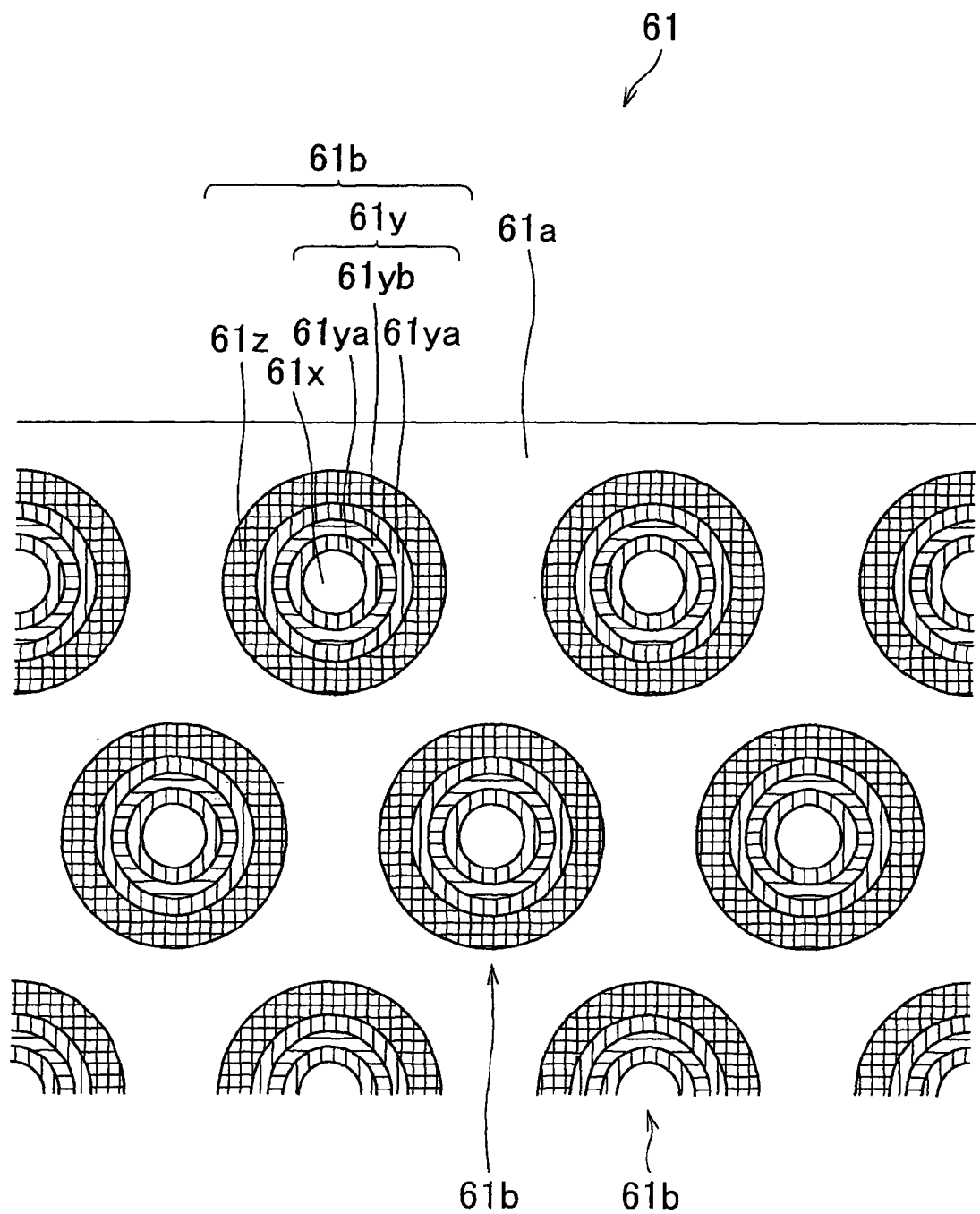
FIG. 4 is a sectional view of a wavelength converting region that can be used in the above embodiments.

FIG. 4 is a sectional view illustrating an embodiment of a wavelength converting region 61. FIG. 4 shows an enlarged view of a portion of a wavelength converting region 61. As shown in FIG. 4, the wavelength converting region 61 has a transparent material 61*a* and a plurality of wavelength converting particles 61*b*, which plurality of wavelength converting particles 61*b* are dispersed in and held by the transparent material 61*a*. The transparent material region 61*a* is composed of a transparent material (e.g., a transparent material having an energy gap of at least 4.0 eV) that allows light to pass through and does not absorb the light that is to be absorbed by the wavelength converting particles 61*b*. Each wavelength converting particle 61*b* has at the center thereof a carrier generating region 61*x*, and includes, arranged concentrically from the center outward, a carrier generating region 61*x*, a carrier selective transfer region 61*y* and a light emitting region 61*z*. The carrier generating region 61*x*, the carrier selective transfer region 61*y* and the light emitting region 61*z* are each composed of semiconductor materials. The carrier selective transfer region 61*y* includes, arranged concentrically from the center side outward, a barrier layer 61*ya*, a quantum well layer 61*yb* and a barrier layer 61*ya*, each of the barrier layers 61*ya* being set to a thickness such that carriers can pass therethrough by tunneling conduction. The barrier layer 61*ya* disposed on the center side is formed on the surface of the carrier generating region 61*x*, the quantum well layer 61*yb* is formed on the surface of the barrier layer 61*ya* disposed on the center side, and the barrier layer 61*ya* disposed on the outer side is formed on the surface of the quantum well layer 61*yb*. The energy gap of the semiconductor material making up the barrier layers 61*ya* is larger than the energy gap of the semiconductor material making up the quantum well layer 61*yb*, and discrete energy levels owing to quantum confinement effects are formed in the conduction and valence bands of the quantum well layer 61*yb*. In the carrier selective transfer region 61*y*, the energy difference between the lowest discrete energy level in the conduction band of the quantum well layer 61*yb* and the lowest discrete energy level in the valence band of the quantum well layer 61*yb* is about 0.1 eV larger than the energy gap of the semiconductor material making up the light emitting region 61*z*. Moreover, in the case of a band diagram drawn such that an upper region of the diagram indicates a higher energy of an electron, the lowest discrete energy level in the conduction band of the quantum well layer 61*yb* is located 0.05 eV above the bottom edge of the conduction band for the semiconductor material making up the light emitting region 61*z*, and the lowest discrete energy level in the valence band of the quantum well layer 61*yb* is located 0.05 eV below the top edge of the valence band for the semiconductor material making up the light emitting region 61*z*.

When light falls on the wavelength converting region 61 constructed in this way, the light passes through the transparent material region 61*a*, reaching the wavelength converting particles 61*b*. When light enters a wavelength converting particle 61*b*, that light having a larger energy than the energy gap of the carrier generating region 61*x* is absorbed, and electrons and holes having various energies are generated in the carrier generating region 61*x*.

Here, the barrier layer 61*ya* disposed on the center side is set to a thickness such that carriers generated in the carrier generating region 61*x* can move to the quantum well layer 61*yb* by tunneling conduction, and the barrier layer 61*ya* disposed on the outer side is set to a thickness such that carriers located in the quantum well layer 61*yb* can move to the light emitting region 61*z* by tunneling conduction. Therefore, of the electrons and holes generated in the carrier generating region 61*x*, those electrons and holes having energies that correspond to the discrete energy levels formed in the conduction band or valence band of the quantum well layer 61*yb* are able to reach the light emitting region 61*z* via discrete energy levels of the quantum well layer 61*yb* by tunneling conduction. The electrons and holes that have moved in this way to the light emitting region 61*z* recombine at the light emitting region 61*z*, becoming monochromatic light. Of the electrons that are generated in the carrier generating region 61*x*, some of the electrons that have energies differing from the discrete energy levels formed in the conduction band of the quantum well layer 61*yb* come to have, by mutual energy transfer with other electrons generated in the carrier generating region 61*x*, the same energy as a discrete energy level formed in the conduction band of the quantum well layer 61*yb*. Similarly, of the holes that are generated in the carrier generating region 61*x*, some of the holes that have energies differing from the discrete energy levels formed in the valence band of the quantum well layer 61*yb* come to have, by mutual energy transfer with other holes generated in the carrier generating region 61*x*, the same energy as a discrete energy level formed in the valence band of the quantum well layer 61*yb*. The electrons and holes that have come to have the same energies as discrete energy levels formed in the conduction band and the valence band of the quantum well layer 61*yb* are able to reach the light emitting region 61*z* by tunneling conduction via discrete energy levels of the quantum well layer 61*yb*, and recombine at the light emitting region 61*z*, becoming monochromatic light. Monochromatic light can be generated in this way in cases where the wavelength converting region 61 is used in photoelectric conversion devices according to the first to third embodiments of the invention.

In the wavelength converting region 61, the transparent material 61*a* may be $SiO_2$ or $SiN_x$, or may be resin such as polystyrene, polyvinyl alcohol, polypropylene, or a methacrylate polymer (acrylic). Alternatively, in this invention, it is possible to use as the transparent material 61*a* an insulating material together with a semiconductor material that does not absorb the light that is to be absorbed by the carrier generating region 61*x*.

The diameter of the carrier generating region 61*x* in the wavelength converting particle 61*b*, from the standpoint of, for example, having a size at which light is absorbed and carriers are generated, is set to at least 2 nm and, from the standpoint of, for example, being able to obtain quantum confinement effects and shortening the carrier movement length, is set to not more than 20 nm. The energy gap of the semiconductor material making up the carrier generating region 61*x* may be set to, for example, at least 0.4 eV and not more than 1.6 eV. When the carrier generating region 61*x* is set to the above size, owing to quantum effects, the energy gap of the carrier generating region 61*x* becomes larger than the energy gap of the bulk material. Materials similar to the semiconductor materials that may be used to construct the above-described carrier generating region 31 may be used in the carrier generating region 61*x* according to the present embodiment, and the carrier generating region 61*x* of the present embodiment may be fabricated by a process similar to that used for fabricating the above-described carrier generating region 31.

From the standpoint of, for example, providing thicknesses at which the carriers are able to move by tunneling conduction, the thicknesses of the barrier layers 61*ya* may be set to, e.g., at least 2 nm and not more than 10 nm. The energy gap of the semiconductor material making up the barrier layers 61*ya* may be set to, for example, at least 1.2 eV and not more than 4.0 eV. A material similar to the semiconductor materials that may constitute the barrier layers of the above-described carrier selective transfer region 12 may be used for the barrier layers 61*ya*, and the these barrier layers 61*ya* may be fabricated by a method similar to that used to fabricate the barrier layer in the above-described carrier selective transfer region 12.

From the standpoint of providing a thickness at which a limited number of discrete energy levels can be formed in the conduction band and the valence band, the thickness of the quantum well layer 61*yb* may be set to, for example, at least 2 nm and not more than 10 nm, and the energy gap of the semiconductor material making up the quantum well layer 61*yb* may be set to at least 0.6 eV and not more than 3.0 eV. When the quantum well layer 61*yb* is set to the above thickness, owing to quantum effects, the energy gap of the quantum well layer 61*yb* becomes larger than the energy gap of the bulk material. Moreover, a material similar to the semiconductor material that may constitute the quantum well layer of the above-described carrier selective transfer region 12 may be used for the quantum well layer 61*yb*, and the quantum well layer 61*yb* may be fabricated by a method similar to that used to fabricate the quantum well layer in the above-described carrier selective transfer region 12.

The thickness of the light emitting region 61*z* may be set to at least 2 nm in order to provide a thickness such that electrons and holes that have moved to the light emitting region 61*z* can recombine, and not more than 20 nm in order to provide a thickness such that the monochromatic light generated in the light emitting region 61*z* can easily travel to the photoelectric conversion region. The energy gap of the semiconductor material making up the light emitting region 61*z* may be set to, for example, at least 0.6 eV and not more than 3.0 eV. A material similar to the semiconductor material that may constitute the light emitting region of the above-described carrier selective transfer region 12 may be used for the light emitting region 61*z*, and the light emitting region 61*z* may be fabricated by a method similar to that used to fabricate the light emitting region in the above-described carrier selective transfer region 12.

An exemplary method of fabricating the wavelength converting particles 61*b* by chemical synthesis will be described below for a case in which PbSe is used for the carrier generating region 61*x*, ZnS is used for the barrier layers 61*ya*, and CdTe is used for the quantum well layer 61*yb* and the light emitting region 61*z*.

(Synthesis of Carrier Generating Region 61*x*)

A flask (referred to as "the first flask" in the following description concerning a method of fabricating the wavelength converting particles 61*b*) was charged with phenyl ether (as a solvent), oleic acid, trioctylphosphine, and lead acetate (as a lead source), and the lead acetate was dissolved by heating to about 85° C. in an inert gas, following which the flask contents were cooled to about 45° C. Next, trioctylphosphine selenide as a selenium source was added to the first flask. A separate flask (referred to as "the second flask" in the following description concerning a method of fabricating the wavelength converting particles 61*b*) from the first flask was charged with phenyl ether, and heated to about 200° C. in an inert gas. Next, the solution in the first flask to which the selenium source had been added was poured into the heated second flask, and the contents of the second flask were cooled to about 120° C. Carrier generating regions 61*x* (PbSe quantum dots) having a diameter of about 8 nm can be produced by the foregoing operation. The energy gap of PbSe is 0.27 eV in the bulk material, but becomes about 0.7 eV due to quantum effects.

(Synthesis of Barrier Layer 61*ya*)

A flask (referred to as "the third flask" in the following description concerning a method of fabricating the wavelength converting particles 61*b*) was charged with trioctylphosphine, then dimethylzinc (as a zinc source) and bis (trimethylsilyl) sulfide (as a sulfur source) were added, and the flask contents were heated to about 300° C. Next, the solution in the third flask was added to the second flask that had been reheated to about 200° C., and the contents were cooled to about 100° C. Through the foregoing operation, a barrier layer 61*ya* (ZnS layer) having a thickness of about 3 nm was formed around the carrier generating region 61*x*. The energy gap of the ZnS layer thus formed was 3.58 eV.

(Synthesis of Quantum Well Layer 61*yb*)

A flask (referred to as "the fourth flask" in the following description concerning a method of fabricating the wavelength converting particles 61*b*) was charged with trioctylphosphine, ditnethylcadmium (as a cadmium source), and trioctylphosphine-tellurium (as a tellurium source), and dissolution was carried out by heating to about 220° C. Next, the solution in the fourth flask was added to the second flask that had been reheated to about 240° C. Through the foregoing operation, a quantum well layer 61*yb* (CdTe layer) having a thickness of about 5 nm was formed around the barrier layer 61*ya*. The energy gap of CdTe is 1.44 eV in the bulk material, but becomes about 1.65 eV due to quantum effects.

(Synthesis of Barrier Layer 61*ya*)

A flask (referred to as "the fifth flask" in the following description concerning a method of fabricating the wavelength converting particles 61*b*) was charged with trioctylphosphine, then dimethylzinc (as a zinc source) and bis (trimethylsilyl) sulfide (as a sulfur source) were added, and the flask contents were heated to about 300° C. Next, the solution in the fifth flask was added to the second flask that had been reheated to about 200° C., and the contents were cooled to about 100° C. Through the foregoing operation, a barrier layer 61*ya* (ZnS layer) having a thickness of about 3 nm was thereby formed around the quantum well layer 61*yb*. The energy gap of the ZnS layer thus formed was 3.58 eV.

(Synthesis of Light Emitting Region 61*z*)

A flask (referred to as "the sixth flask" in the following description concerning a method of fabricating the wavelength converting particles 61*b*) was charged with trioctylphosphine, then dimethylcadmium (as a cadmium source) and trioctylphosphine-tellurium (as a tellurium source) were added, and dissolution was carried out by heating to about 220° C. Next, the solution in the sixth flask was added to the second flask that had been reheated to about 240° C. Through the foregoing operation, a light emitting region 61z (CdTe layer) having a thickness of about 10 nm was formed around the barrier layer 6lya. When a light emitting region 61z is thus formed, wavelength converting particles 61b can be obtained via, for example, a step in which washing is carried out using methanol.

Once the wavelength converting particles 61b are fabricated in this way, a transparent material 61a composed of the substance described above is placed in an organic solvent, and the wavelength converting particles 61b are dispersed therein. The solution, in which the transparent material 61a and the wavelength converting particles 61b are dispersed, is then applied, by a coating process such as spin coating or dip coating or by a printing process such as screen printing or ink-jet printing, onto the surface of the substance, on which the wavelength converting region 61 is to be formed, following which annealing treatment is carried out. The wavelength converting region 61 can be fabricated by repeatedly applying the dispersion and carrying out annealing treatment; i.e., by carrying out these operations a plurality of times.

Figure 5A:
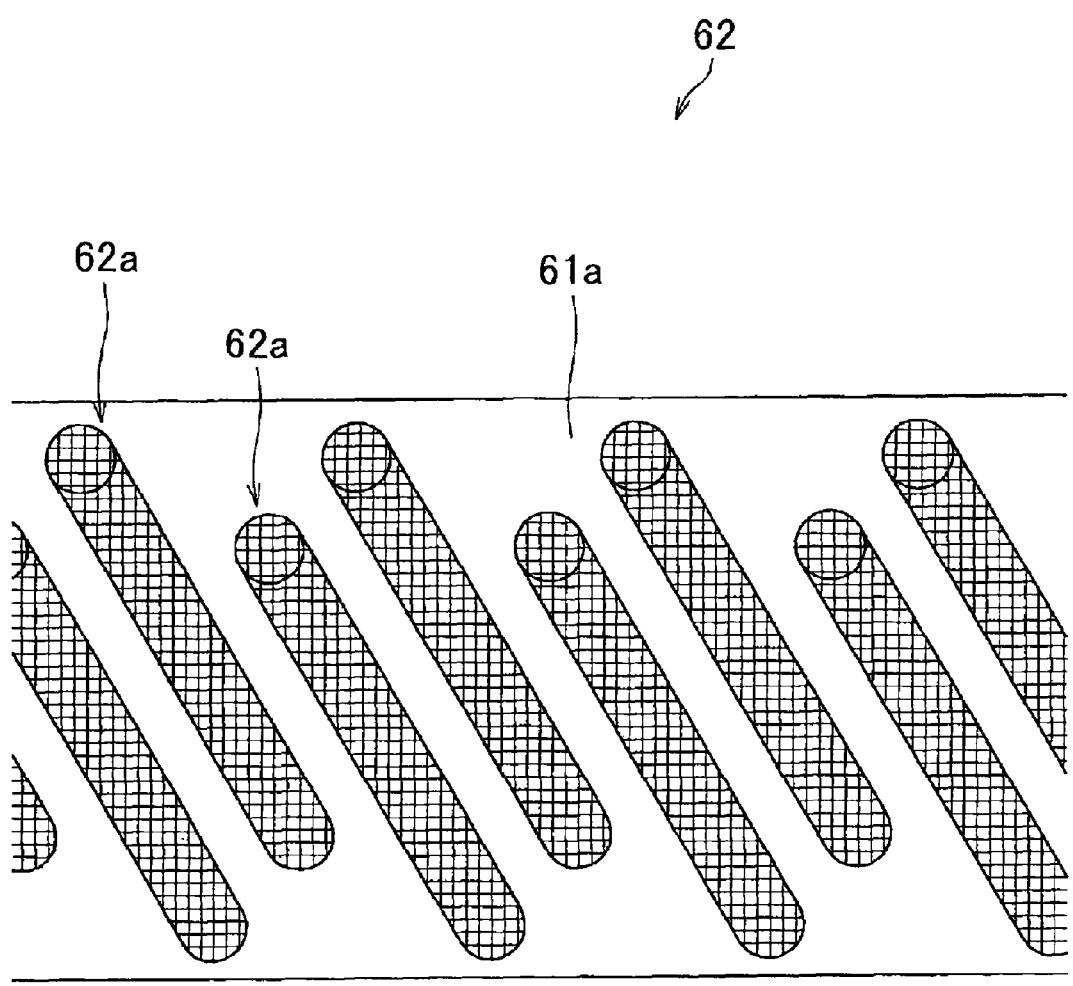
FIG. 5A is a sectional view of a wavelength converting region that can be used in the above embodiments.
Figure 5B:
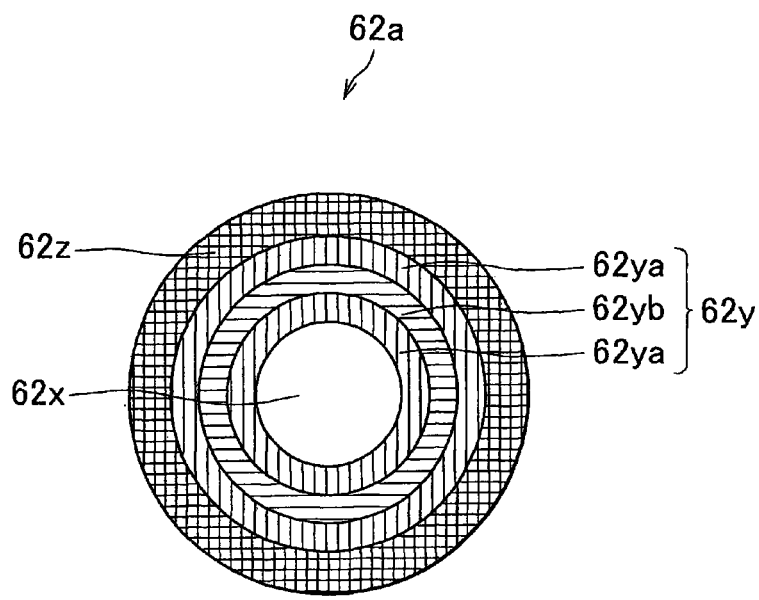
FIG. 5B is a sectional view of a wavelength converting fiber in the wavelength converting region shown in FIG. 5 A.

FIG. 5A is a sectional view showing an embodiment of a wavelength converting region 62, and FIG. 5B is a sectional view showing an embodiment of a wavelength converting fiber 62a. The front/back direction relative to the sheet, on which FIG. 5B is drawn, is the axial direction of the wavelength converting fiber 62a. In FIG. 5A, a portion of the wavelength converting region 62 is shown enlarged, and a plurality of wavelength converting fibers 62a are schematically shown. In FIG. 5A, elements similar to those in the above-described wavelength converting region 61 are denoted by the same symbols as are used in FIG. 4, and explanations of those elements are omitted below as appropriate.

As shown in FIG. 5A, the wavelength converting region 62 has a transparent material 61a and a plurality of wavelength converting fibers 62a, which wavelength converting fibers 62a are dispersed in and held by the transparent material 61a. The transparent material region 61a is composed of a transparent material (e.g., a transparent material having an energy gap of at least 4.0 eV) that allows light to pass through and does not absorb the light that is to be absorbed by the wavelength converting fibers 62a. As shown in FIG. 5B, each wavelength converting fiber 62a has a carrier generating region 62x at the center and also has, arranged concentrically from the center outward, a carrier generating region 62x, a carrier selective transfer region 62y and a light emitting region 62z. The carrier generating region 62x, the carrier selective transfer region 62y and the light emitting region 62z are each composed of semiconductor materials. The carrier selective transfer region 62y includes, arranged concentrically from the center side outward, a barrier layer 62ya, a quantum well layer 62yb and a barrier layer 62ya, each of the barrier layers 62ya being set to a thickness such that carriers can pass therethrough by tunneling conduction. The barrier layer 62ya disposed on the center side is formed on the surface of the carrier generating region 62x, the quantum well layer 62yb is formed on the surface of the barrier layer 62ya disposed on the center side, and the barrier layer 62ya disposed on the outer side is formed on the surface of the quantum well layer 62yb. The energy gap of the semiconductor material making up the barrier layers 62ya is larger than the energy gap of the semiconductor material making up the quantum well layer 62yb, and discrete energy levels owing to quantum confinement effects are formed in the conduction and valence bands of the quantum well layer 62yb. In the carrier selective transfer region 62y, the energy difference between the lowest discrete energy level in the conduction band of the quantum well layer 62yb and the lowest discrete energy level in the valence band of the quantum well layer 62yb is about 0.1 eV larger than the energy gap of the semiconductor material making up the light emitting region 62z. Moreover, in a band diagram drawn such that an upper region of the diagram indicates a higher energy of an electron, the lowest discrete energy level in the conduction band of the quantum well layer 62yb is located 0.05 eV above the bottom edge of the conduction band for the semiconductor material making up the light emitting region 62z, and the lowest discrete energy level in the valence band of the quantum well layer 62yb is located 0.05 eV below the top edge of the valence band for the semiconductor material making up the light emitting region 62z.

When light falls on a wavelength converting region 62 constructed in this way, the light passes through the transparent material region 61a, reaching the wavelength converting fibers 62a. When light enters the wavelength converting fibers 62a, light having an energy that is larger than the energy gap of the carrier generating region 62x is absorbed, and electrons and holes having various energies are generated in the carrier generating region 62x.

Here, the barrier layer 62ya disposed on the center side is set to a thickness such that carriers generated at the carrier generating region 62x can move to the quantum well layer 62yb by tunneling conduction, and the barrier layer 62ya disposed on the outer side is set to a thickness such that carriers located in the quantum well layer 62yb can move to the light emitting region 62z by tunneling conduction. Therefore, of the electrons and holes generated in the carrier generating region 62x, those electrons and holes having energies that correspond to the discrete energy levels formed in the conduction band or valence band of the quantum well layer 62yb are able to reach the light emitting region 62z via discrete energy levels of the quantum well layer 62yb by tunneling conduction. The electrons and holes that have moved in this way to the light emitting region 62z recombine at the light emitting region 62z, becoming monochromatic light. Of the electrons that are generated in the carrier generating region 62x, some of the electrons that have energies differing from the discrete energy levels formed in the conduction band of the quantum well layer 62yb come to have, by mutual energy transfer with other electrons generated in the carrier generating region 62x, the same energy as a discrete energy level formed in the conduction band of the quantum well layer 62yb. Similarly, of the holes that are generated in the carrier generating region 62x, some of the holes that have energies differing from the discrete energy levels formed in the valence band of the quantum well layer 62yb come to have, by mutual energy transfer with other holes generated in the carrier generating region 62x, the same energy as a discrete energy level formed in the valence band of the quantum well layer 62yb. The electrons and holes that have come to have the same energies as discrete energy levels formed in the conduction band and the valence band of the quantum well layer 62yb are able to reach the light emitting region 62z by tunneling conduction via discrete energy levels of the quantum well layer 62yb, and recombine at the light emitting region 62z, becoming monochromatic light. Monochromatic light can be generated in this way in cases where the wavelength converting region 62 is used in photoelectric conversion devices according to the first to third embodiments of the invention.

In the wavelength converting region 62, for the same reasons as mentioned above in connection with the above-described carrier generating region 61*x*, the diameter of the carrier generating region 62*x* in the wavelength converting fibers 62*a* may be set to, for example, at least 2 nm and not more than 20 nm, and the energy gap of the semiconductor material making up the carrier generating region 62*x* may be set to, for example, at least 0.4 eV and not more than 1.6 eV. When the carrier generating region 62*x* is set to the foregoing thickness, owing to quantum effects, the energy gap of the carrier generating region 62*x* becomes larger than the energy gap of the bulk material. Materials similar to the semiconductor materials used for the above-described carrier generating region 31 may be used for this carrier generating region 62*x*, and this carrier generating region 62*x* may be fabricated by a method similar to that used for the above-described carrier generating region 31. In cases where a layer composed of the wavelength converting fibers 62*a* buried in a transparent material is formed, the thickness of this layer will presumably be not more than about 1 μm, and so it is desirable to keep the wavelength converting fibers 62*a* from breaking through this layer. Accordingly, it is preferable to set the axial length of the wavelength converting fibers 62*a* to, for example, at least 20 nm and not more than 500 nm.

For the same reasons as mentioned above in connection with the barrier layers 61*ya* of the preceding embodiment, the thicknesses of the barrier layers 62*ya* of the present embodiment may be set to, for example, at least 2 nm and not more than 10 nm, and the energy gap of the semiconductor material making up these barrier layers 62*ya* may be set to, for example, at least 1.2 eV and not more than 4.0 eV. A material similar to the semiconductor materials used for the barrier layers of the above-described carrier selective transfer region 12 may be used for the barrier layers 62*ya*, and these barrier layers 62*ya* may be fabricated by a method similar to that used to fabricate the barrier layers in the above-described carrier selective transfer region 12.

For the same reasons as mentioned above in connection with the quantum well layer 61*yb* of the preceding embodiment, the thickness of the quantum well layer 62*yb* may be set to, for example, at least 2 nm and not more than 10 nm, and the energy gap of the semiconductor material making up the quantum well layer 62*yb* may be set to at least 0.6 eV and not more than 3.0 eV. When the quantum well layer 62*yb* is set to the above thickness, owing to quantum effects, the energy gap of the quantum well layer 62*yb* becomes larger than the energy gap of the bulk material. Moreover, a material similar to the semiconductor material used for the quantum well layer of the above-described carrier selective transfer region 12 may be used for the quantum well layer 62*yb*, and the quantum well layer 62*yb* may be fabricated by a method similar to that used to fabricate the quantum well layer in the above-described carrier selective transfer region 12.

For the same reasons as mentioned above in connection with the light emitting region 61*z* of the preceding embodiment, the thickness of the light emitting region 62*z* may be set to at least 2 nm and not more than 20 nm. The energy gap of the semiconductor material making up the light emitting region 62*z* may be set to, for example, at least 0.6 eV and not more than 3.0 eV. A material similar to the semiconductor material used for the light emitting region of the above-described carrier selective transfer region 12 may be used for the light emitting region 62*z*, and the light emitting region 62*z* may be fabricated by a method similar to that used to fabricate the light emitting region in the above-described carrier selective transfer region 12.

An exemplary method of fabricating the wavelength converting fibers 62*a* by chemical synthesis will be described below for a case in which PbSe is used for the carrier generating region 62*x*, ZnS is used for the barrier layers 62*ya*, and CdTe is used for the quantum well layer 62*yb* and the light emitting region 62*z*.

(Synthesis of Carrier Generating Region 62*x*)

A flask (referred to as "the first flask" in the following description concerning a method of fabricating the wavelength converting fibers 62*a*) was charged with phenyl ether (as a solvent), oleic acid and lead acetate (as a lead source), and the lead acetate was dissolved by heating to about 150° C. in an inert gas, following which the flask contents were cooled to about 60° C. Next, trioctylphosphine selenide as a selenium source and trioctylphosphine were added to the first flask. A separate flask (referred to as "the second flask" in the following description concerning a method of fabricating the wavelength converting fibers 62*a*) from the first flask was charged with phenyl ether and tetradecylphosphine, and heated to about 250° C. (the temperature of the added solution) in an inert gas. Next, the solution in the first flask to which the selenium source had been added was poured into the heated second flask, and the contents of the second flask were held at about 180° C. (the reaction temperature). Carrier-generating regions 62*x*(PbSe fibers) having a thickness of about 6 nm can be produced by the foregoing operation. Here, as the temperature of the added solution and the reaction temperature become higher and the concentration ratio Pb/Se of the starting materials in the solution becomes larger, it becomes more likely to form fibers instead of particles. The energy gap of PbSe is 0.27 eV in the bulk material, but becomes about 0.7 eV due to quantum effects.

(Synthesis of Barrier Layer 62*ya*)

A flask (referred to as "the third flask" in the following description concerning a method of fabricating the wavelength converting fibers 62*a*) was charged with trioctylphosphine, then dimethylzinc (as a zinc source) and bis(trimethylsilyl) sulfide (as a sulfur source) were added, and the flask contents were heated to about 300° C. Next, the solution in the third flask was added to the second flask that had been reheated to about 200° C., and the contents were cooled to about 100° C. Through the foregoing operation, a barrier layer 62*ya* (ZnS layer) having a thickness of about 3 nm was formed around the carrier generating region 62*x*. The energy gap of the ZnS layer thus formed was 3.58 eV.

(Synthesis of Quantum Well Layer 62*yb*)

A flask (referred to as "the fourth flask" in the following description concerning a method of fabricating the wavelength converting fibers 62*a*) was charged with trioctylphosphine, dimethylcadmium (as a cadmium source), and trioctylphosphine-tellurium (as a tellurium source), and dissolution was carried out by heating to about 220° C. Next, the solution in the fourth flask was added to the second flask that had been reheated to about 240° C. Through the foregoing operation, a quantum well layer 62*yb* (CdTe layer) having a thickness of about 5 nm was formed around the barrier layer 62*ya*. The energy gap of CdTe is 1.44 eV in the bulk material, but becomes about 1.65 eV due to quantum effects.

(Synthesis of Barrier Layer 62*ya*)

A flask (referred to as "the fifth flask" in the following description concerning a method of fabricating the wavelength converting fibers 62*a*) was charged with trioctylphosphine, then dimethylzinc (as a zinc source) and bis(trimethylsilyl) sulfide (as a sulfur source) were added, and the flask contents were heated to about 300° C. Next, the solution in the fifth flask was added to the second flask that had been reheated to about 200° C., and the contents were cooled to about 100° C. Through the foregoing operation, a barrier layer 62ya (ZnS layer) having a thickness of about 3 nm was formed around the quantum well layer 62yb. The energy gap of the ZnS layer thus formed was 3.58 eV.

(Synthesis of Light Emitting Region 62z)

A flask (referred to as "the sixth flask" in the following description concerning a method of fabricating the wavelength converting fibers 62a) was charged with trioctylphosphine, then dimethylcadmium (as a cadmium source) and trioctylphosphine-tellurium (as a tellurium source) were added, and dissolution was carried out by heating to about 220° C. Next, the solution in the sixth flask was added to the second flask that had been reheated to about 240° C. Through the foregoing operation, a light emitting region 62z (CdTe layer) having a thickness of about 10 nm was formed around the barrier layer 62ya. When a light emitting region 62z is thus formed, wavelength converting fibers 62a can be obtained via, for example, a step in which washing is carried out using methanol.

Once the wavelength converting fibers 62a are fabricated in this way, a transparent material 61a composed of the substance described above is placed in an organic solvent, and the wavelength converting fibers 62a are dispersed therein. The solution, in which the transparent material 61a and the wavelength converting fibers 62a are dispersed, is then applied, by a coating process such as spin coating or dip coating or by a printing process such as screen printing or ink-jet printing, onto the surface of the substance, on which the wavelength converting region 62 is to be formed, following which annealing treatment is carried out. The wavelength converting region 62 can be fabricated by repeatedly applying the dispersion and carrying out annealing treatment; i.e., by carrying out these operations a plurality of times.

In wavelength converting regions 61 and 62, no particular limitation is imposed on the number of wavelength converting particles 61b or wavelength converting fibers 62a that are held in the transparent material 61a. However, in order to absorb at least 60%, and preferably at least 80%, of the photons in the wavelength range at and above the energy gap of the carrier generating region 61x or 62x, it is required to set the total thickness of the carrier generating regions 61x or 62x in the wavelength converting region 61 or 62 (that is, the thickness in the direction of travel of sunlight; the same applies below) to at least about 100 nm and not more than about 500 nm. In cases where the diameter of the carrier generating region 61x or 62x is at least 2 nm and not more than 20 nm, the total thickness of the carrier generating regions 61x or 62x can be set to at least about 100 nm and not more than about 500 nm by stacking about 5 to 250 layers of the wavelength converting particles 61b or the wavelength converting fibers 62a. For example, in a case where the diameter of the carrier generating region 61x or 62x is about 10 nm, from about 10 to about 50 layers of the wavelength converting particles 61b or the wavelength converting fibers 62a may be stacked.

Also, in wavelength converting regions 61 and 62, although no limitation is imposed on the spacing between neighboring wavelength converting particles 61b or wavelength converting fibers 62a held in the transparent material 61a, from the standpoint of, for example, obtaining an embodiment that readily increases the photoelectric conversion efficiency, it is preferable for the spacing to be set to at least about 0.2 times but not more than about 2 times the diameter of the wavelength converting particles 61b or the wavelength converting fibers 62a. For example, in a case where the diameter of the wavelength converting particles 61b or the wavelength converting fibers 62a is 20 nm, the spacing may be set to at least about 4 nm but not more than about 40 nm.

Moreover, in wavelength converting regions 61 and 62, with regard to the volumetric ratio of the transparent material 61a to the wavelength converting particles 61b or the wavelength converting fibers 62a that are mixed together during fabrication, the volume of the transparent material 61a may be set to a value of at least about 0.5 and not more than about 20 when the volume of the wavelength converting particles 61b or the wavelength converting fibers 62a is assumed to be one.

In the above explanations of the wavelength converting regions 61 and 62, embodiments have been described in which wavelength converting particles 61b or wavelength converting fibers 62a are dispersed in a transparent material 61a. However, the wavelength converting region of the invention is not limited to these embodiments. The photoelectric conversion device of the invention may have a wavelength converting region composed of both wavelength converting particles 61b and wavelength converting fibers 62a dispersed in a transparent material 61a. Yet another possible embodiment of the photoelectric conversion device of the invention is one that does not use a transparent material 61a, and instead has a wavelength converting region formed by, for example, subjecting the wavelength converting particles 61b and/or the wavelength converting fibers 62a to a pressing operation. However, in order to obtain an embodiment in which the shape of the wavelength converting region is easily defined, an embodiment having a wavelength converting region composed of wavelength converting particles 61b and/or wavelength converting fibers 62a dispersed in a transparent material 61a is preferable.

Figure 6:
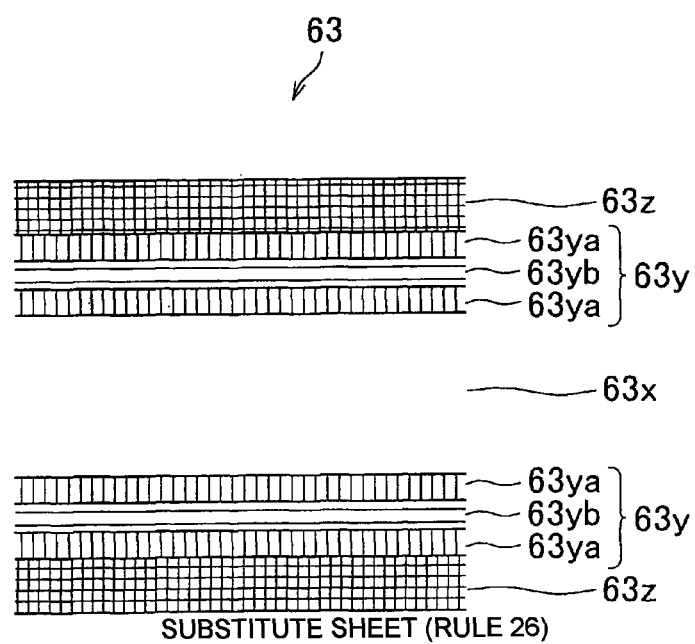
FIG. 6 is a sectional view of a wavelength converting region that can be used in a solar cell according to a fourth embodiment of the invention.

FIG. 6 is a sectional view showing an embodiment of a wavelength converting region 63. The vertical direction in FIG. 6 is the direction of travel of light and is also the thickness direction of the wavelength converting region 63. As shown in FIG. 6, a wavelength converting region 63 has a earner generating region 63x disposed at the center in the thickness direction thereof, a pair of carrier selective transfer regions 63y disposed so as to sandwich the carrier generating region 63x, and a pair of light emitting regions 63z disposed so as to additionally sandwich from outside the carrier generating region 63x that is sandwiched by the pair of carrier selective transfer regions 63y. The carrier generating region 63x, the pair of carrier selective transfer regions 63y, and the pair of light emitting regions 63z are respectively composed of semiconductor materials. Each of the respective carrier selective transfer regions 63y has, disposed in order from the carrier generating region 63x side toward the respective light emitting region 63z sides, a barrier layer 63ya, a quantum well layer 63yb, the barrier layers 63ya being set to thicknesses such that carrier can pass there through by tunneling conduction. The energy gap of the semiconductor material making up the barrier layers 63ya is larger than the energy gap of the semiconductor material making up the carrier generating region 63x and larger than the energy gap of the semiconductor material making up the respective quantum well layers 63yb, as a result of which discrete energy levels owing to quantum confinement effects form in the conduction and valence bands of the quantum well layers 63yb. In the carrier selective transfer regions 63y, the energy difference between the lowest discrete energy level in the conduction band of the quantum well layers 63 yb and the lowest discrete energy level in the valence band of the quantum well layers 63yb is about 0.1 eV larger than the energy gap of the semiconductor material making up the light emitting regions 63z. Moreover, in a band diagram drawn such that an upper region of the diagram indicates a higher energy of an electron, the lowest discrete energy level in the conduction band of the quantum well layers 63yb is located 0.05 eV above the bottom edge of the conduction band for the semiconductor material making up the light emitting regions 63z, and the lowest discrete energy level in the valence band of the quantum well layers 63yb is located 0.05 eV below the top edge of the valence band for the semiconductor material making up the light emitting regions 63z. The wavelength converting region 63 can be fabricated as follows. For example, after forming the light emitting region 63z located on the bottom side in FIG. 6, a carrier selective transfer region 63y can be formed on the top surface of the light emitting region 63z by forming a barrier layer 63ya on the top surface of the light emitting region 63z, forming a quantum well layer 63yb on the top surface of the barrier layer 63ya, and forming a barrier layer 63ya on the top surface of the quantum well layer 63yb. Once the carrier selective transfer region 63y is thus formed, a carrier generating region 63x may be formed on the top surface thereof. Next, a carrier selective transfer region 63y is formed on the top surface of the carrier generating region 63 x by forming a barrier layer 63ya on the top surface of the carrier generating region 63x, forming a quantum well layer 63yb on the top surface of the barrier layer 63ya, and forming a, barrier layer 63ya on the top surface of the quantum well layer 63yb. A light emitting region 63z is then formed on the top surface of the carrier selective transfer region 63y that has been thus formed. Through this sequence of steps, it is possible to fabricate a wavelength converting region 63 having a multilayer construction.

Figure 7:
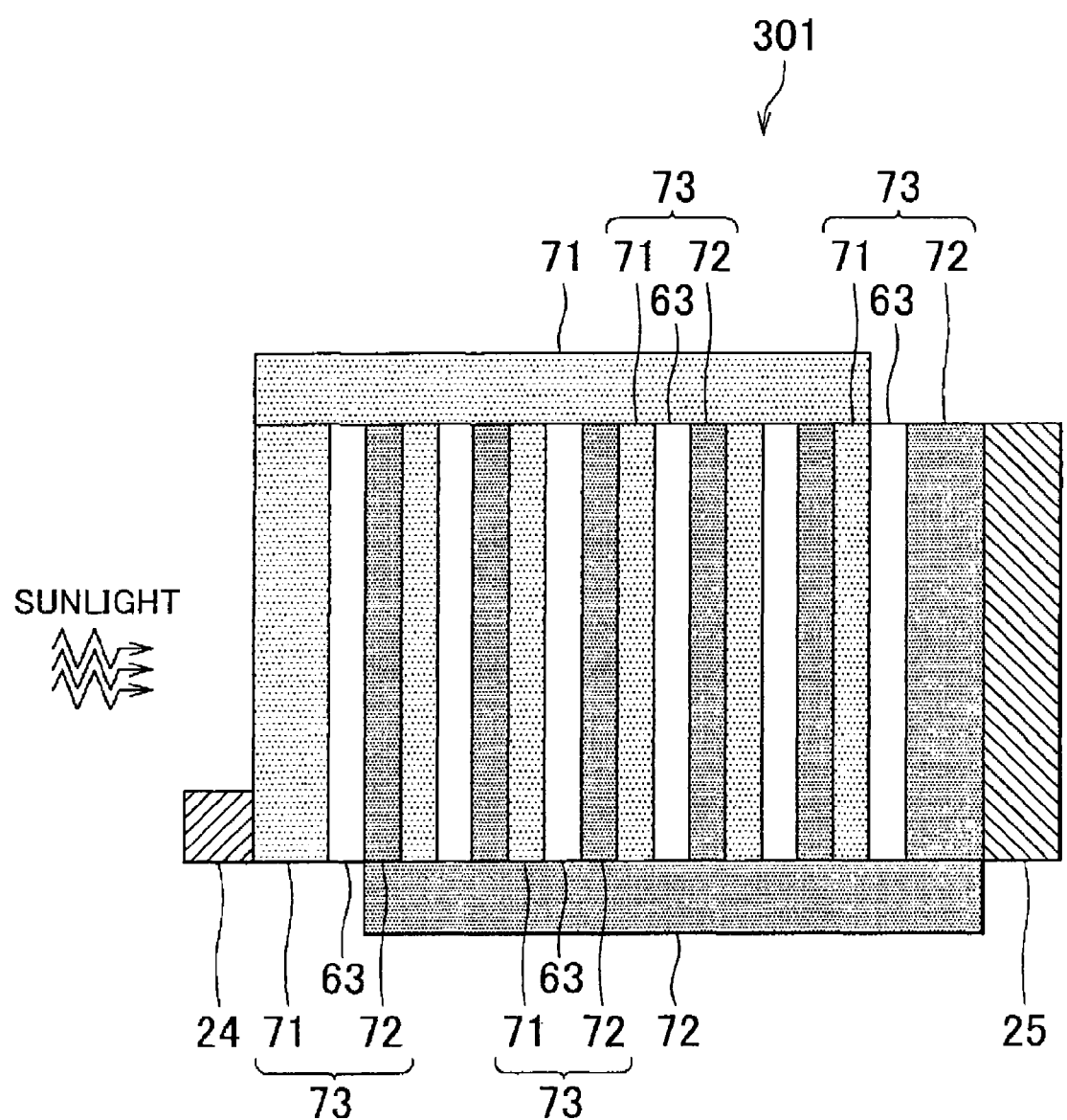
FIG. 7 is a sectional view of a solar cell according to the fourth embodiment of the invention.

The wavelength converting region 63 thus constructed may be disposed inside, for example, a photoelectric conversion region. FIG. 7 is a sectional view showing a solar cell 301 according to another embodiment of the invention that is provided with a photoelectric conversion region 73 having a plurality of wavelength converting regions 63 at the interior thereof. The lateral direction in FIG. 7 is the direction in which light travels and is also the thickness direction of the wavelength converting region 63. In FIG. 7, the wavelength converting regions 63 are schematically shown. Elements in FIG. 7 that are similar to those in the above-described solar cell 100 are denoted by the same symbols as are used in FIG. 1A and explanations of those elements are omitted below as appropriate.

The solar cell 301 shown in FIG. 7 has a surface electrode 24, a back electrode 25, a plurality of n layers 71 connected to the surface electrode 24, a plurality of p layers 72 connected to the back electrode 25, and a plurality of wavelength converting regions 63 disposed between the n layers 71 and the p layers 72. An n layer 71 is situated at an end of the solar cell 301 where the surface electrode 24 is disposed on an upstream side in the traveling direction of the light, and a p layer 72 is situated at an end of the solar cell 301 where the back electrode 25 is disposed on the downstream side in the direction in which the light travels. A plurality of stacked layers 73, each of which is composed of an n layer 71, a wavelength converting region 63 and a p layer 72 arranged in this order from the upstream side in the direction in which light travels, are disposed successively between the surface electrode 24 and the back electrode 25. The n layers 71 included in the stacked layers 73 are connected together by an n layer 71 disposed on the top side in FIG. 7, and the p layers 72 included in the stacked layers 73 are connected together by a p layer 72 disposed on the bottom side in FIG. 7. In the solar cell 301, the energy gap of the semiconductor material making up the n layers 71 and the energy gap of the semiconductor material up the p layers 72 are each about 0.1 eV smaller than the energy of the monochromatic light generated in the light emitting regions 63z. In the solar cell 301, the light that is not absorbed by the n layers 71 or the p layers 72 is absorbed by the wavelength converting region 63, and the monochromatic light generated at the light emitting regions 63z of the wavelength converting regions 63 is absorbed by the n layers 71 and the p layers 72.

When light falls on the solar cell 301, the light passes through the n layer 71 or the n layers 71 and the p layers 72, and reaches the plurality of wavelength converting regions 63 (also referred to below as simply "the wavelength converting regions 63"). When the light reaches the n layers 71 and/or the p layers 72, some of the light is absorbed, creating carriers. The electrons thus generated are collected at the surface electrode 24 via the n layer 71 connected to the surface electrode 24, and the holes thus generated are collected at the back electrode 25 via the p layer 72 connected to the back electrode 25.

When light enters one of the wavelength converting regions 63, light having a larger energy than the energy gap of the carrier generating region 63x is absorbed, and electrons and holes having various energies are generated in the carrier generating region 63x. Here, the barrier layers 63ya disposed on either side of the carrier generating region 63 x are set to thicknesses such that the carriers can move to the quantum well layers 63yb by tunneling conduction, and the barrier layers 63ya disposed between the quantum well layers 63yb and the light-emitting regions 63z are set to thicknesses such that the carriers can move to the light emitting regions 63z by tunneling conduction. Therefore, of the electrons and holes that are generated in the carrier generating region 63x, those electrons and holes having energies that correspond to discrete energy levels formed in the conduction band or valence band of the quantum well layers 63yb are able, by tunneling conduction, to reach the light emitting regions 63z via the discrete energy levels of the quantum well layers 63yb. The electrons and holes that have thus moved to the light emitting regions 63 z recombine at the light emitting regions 63z, becoming monochromatic light. On the other hand, of the electrons generated in the carrier generating region 63x, some of the electrons having energies that differ from discrete energy levels formed in the conduction bands of the quantum well layers 63yb, by carrying out mutual energy transfer with other electrons generated in the carrier generating region 63x, come to have the same energy as discrete energy levels formed in the conduction band of the quantum well layers 63yb. Similarly, of the holes generated in the carrier generating region 63x, some of the holes having energies that differ from the discrete energy levels formed in the valence bands of the quantum well layers 63yb, by carrying out mutual energy transfer with other holes generated in the earner generating region 63x, come to have the same energy as discrete energy levels formed in the valence band of the quantum well layers 63yb. The electrons and holes that have thus come to have the same energies as discrete energy levels formed in the conduction band and valence band of the quantum well layers 63yb are able, by tunneling conduction, to reach the light emitting regions 63z via the discrete energy levels of the quantum well layers 63yb and recombine at the light emitting regions 63z, becoming monochromatic light. The monochromatic light generated in the light emitting regions 63z reaches an n layer 71 or a p layer 72 located adjacent to the wavelength converting region 63, and is absorbed by the n layer 71 or p layer '72. Electrons generated by absorption of the monochromatic light pass through the n layer 71 situated on the top side in FIG. 7 and are collected at the surface electrode 24, and holes generated by absorption of the monochromatic light pass through the p layer 72 situated on the bottom side in FIG. 7 and are collected at the back electrode 25.

With this solar cell 301 that thus absorbs light and collects electrons and holes, it becomes possible to greatly expand the wavelength range of the light utilized during conversion to electricity in the n layers 71 or p layers 72. Moreover, a purpose of the wavelength converting regions 63 is to allow the carriers that are generated in the carrier generating regions 63x to recombine at the light emitting regions 63z; it is not intended to extract the generated carriers directly to the exterior. Therefore, in the wavelength converting regions 63, unlike in conventional hot carrier solar cells that use a quantum structure, there is no need to have the carriers move all the way to the electrode, so that it is made possible to markedly reduce the energy loss during movement. In particular, by controlling the thickness of the carrier generating regions 63x, and thereby setting the movement length of carriers from the generation in the carrier generating regions 63x until they reach the carrier selective transfer regions 63y to about 10 nm or less, it is possible to greatly reduce energy loss during movement. Moreover, in an embodiment where a semiconductor material is used for the carrier generating regions 63x, it becomes possible to considerably broaden the wavelength range of light that can be utilized for generating carriers as compared to conventional up-conversion solar cells that use fluorescent materials. In addition, in a solar cell 301 wherein the monochromatic light generated in the wavelength converting regions 63 is input to the n layers 71 or the p layers 72, the energy of the light input to the n layers 71 or the p layers 72 is fixed. Thus, the energy loss is easily reduced by using for the n layers 71 or the p layers 72 a semiconductor material having an energy gap corresponding to the fixed energy. Accordingly, it is possible to increase the photoelectric conversion efficiency with this solar cell 301 as well. In this solar cell 301 as well, the photoelectric conversion efficiency is easily increased by increasing the efficiency of the wavelength converting regions 63 that convert light to monochromatic light.

In the solar cell 301, the thickness of the carrier generating region 63x, for the same reasons as mentioned above concerning the above-described carrier generating regions 61x and 62x, may be set to, for example, at least 2 nm and not more than 20 nm, and the energy gap of the semiconductor material making up the carrier generating region 63x may be set to, for example, at least 0.4 eV and not more than 1.6 eV. By giving the carrier generating region 63x the foregoing thickness, owing to quantum effects, the energy gap of the carrier generating region 63x becomes larger than the energy gap of the bulk material. Also, a material similar to the semiconductor material used for the above-described carrier generating region 31 may be used for this carrier generating region 63x. In cases where the carrier generating region 63x is composed of a group IV element such as Ge or Si, or a group III-V compound such as InAs, GaSb, GaAsSb, GaInAs, InP or GaAs, the carrier generating region 63x may be fabricated by a vapor phase growth process such as MOCVD or MBE. In cases where the carrier generating region 63x is composed of a group IV-VI compound such as PbSe or PbS or a group II-VI compound such as CdTe, the carrier generating region 63x may be fabricated by a vacuum deposition process that includes ion plating, by a vapor phase growth process such as sputtering, or by chemical synthesis such as a sol-gel process or chemical bath deposition. Alternatively, fabrication may be carried out by, following the synthesis of particles by a sol-gel process, a solvothermal process or the like, mixing the particles in an organic solvent and applying the resulting mixture, using a coating process such as spin coating or dip coating or a printing process such as screen printing or ink-jet printing, onto the surface of the substance, on which the carrier generating region 63x is to be formed, then carrying out annealing treatment.

The thicknesses of the barrier layers 63ya in this embodiment, for the same reasons as mentioned above in connection with the barrier layers 61ya and the barrier layers 62ya in the above-described embodiments, may be set to, for example, at least 2 nm and not more than 20 nm, and the energy gap of the semiconductor material making up the barrier layers 63ya may be set to, for example, at least 1.2 eV and not more than 4.0 eV. Also, materials similar to the semiconductor materials used for the barrier layers of the above-described carrier selective transfer region 12 may be used for the barrier layers 63ya of the present embodiment. In cases where the barrier layers 63ya are composed of a group III-V compound such as InP, GaAs, AlGaAs, GaInP, AlAs, GaP or GaN, the barrier layers 63ya may be fabricated by a vapor phase growth process such as MOCVD or MBE. In cases where the barrier layers 63ya are composed of a group II-VI compound such as CdTe, CdSe, ZnTe, CdS, ZnSe or ZnS, the barrier layers 63ya may be fabricated by a vacuum deposition process that includes ion plating, by a vapor phase growth process such as sputtering, or by chemical synthesis such as a sol-gel process or chemical bath deposition. Alternatively, fabrication may be carried out by, following the synthesis of particles by a sol-gel process, a solvothennal process or the like, mixing the particles in an organic solvent and applying the resulting mixture, using a coating process such as spin coating or dip coating or a printing process such as screen printing or ink-jet printing, onto the surface of the substance, on which the barrier layer 63ya is to be formed (a light emitting region 63z, a quantum well layer 63yb, or the carrier generating region 63x), then carrying out annealing treatment.

The thickness of the quantum well layer 63yb, for the same reasons as mentioned above concerning the quantum well layers 61yb and 62yb in the above-described embodiments, may be set to, for example, at least 2 nm and not more than 10 nm, and the energy gap of the semiconductor material making up the quantum well layer 63yb may be set to, for example, at least 1.0 eV and not more than 3.0 eV. When the quantum well layer 63yb is set to the foregoing thickness, owing to quantum effects, the energy gap of the quantum well layer 63yb becomes larger than the energy gap of the bulk material. Also, a material similar to the semiconductor material used for the quantum well layer of the above-described carrier selective transfer region 12 may be used for this quantum well layer 63yb. In cases where the quantum well layer 63yb is composed of a group IV element such as Ge or Si, or a group III-V compound such as GaSb, GaAsSb, GaInAs, InP, GaAs, AlGaAs, GaInP, AlAs or GaP, the quantum well layer 63yb may be fabricated by a vapor phase growth process such as MOCVD or MBE. In cases where the quantum well layer 63yb is composed of a group II-VI compound such as CdTe, CdSe, ZnTe, CdS or ZnSe, the quantum well layer 63yb may be fabricated by a vacuum deposition process that includes ion plating, by a vapor phase growth process such as sputtering, or by chemical synthesis such as a sol-gel process or chemical bath deposition. Alternatively, fabrication may be carried out by, following the synthesis of particles by a sol-gel process, a solvothermal process or the like, mixing the particles in an organic solvent and applying the resulting mixture, using a coating process such as spin coating or dip coating or a printing process such as screen printing or ink jet printing, onto the surface of the barrier layer 63ya, on which the quantum well layer 63yb is to be formed, then carrying out annealing treatment.

The thickness of the light emitting region 63z, for the same reasons as mentioned above concerning the light emitting regions 61z and 62z in the above-described embodiments, may be set to, for example, at least 2 nm and not more than 20 nm, and the energy gap of the semiconductor material making up the light emitting region 63z may be set to, for example, at least 1.0 eV and not more than 3.0 eV. A material similar to the semiconductor material used for the light emitting region of the above-described carrier selective transfer region 12 may be used for this light emitting region 63z. In cases where the light emitting region 63z is composed of a group IV element such as Ge or Si, or a group III-V compound such as GaSb, GaAsSb, GaInAs, InP, GaAs, AlGaAs, GaInP, AlAs or GaP, the light emitting region 63z may be fabricated by a vapor phase growth process such as MOCVD or MBE. In cases where the light emitting region 63z is composed of a group II-VI compound such as CdTe, CdSe, ZnTe, CdS or ZnSe, the light emitting region 63z may be fabricated by a vacuum deposition process that includes ion plating, by a vapor phase growth process such as sputtering, or by chemical synthesis such as a sol-gel process or chemical bath deposition. Alternatively, fabrication may be carried out by, following the synthesis of particles by a sol-gel process, a solvothermal process or the like, mixing the particles in an organic solvent and applying the resulting mixture, using a coating process such as spin coating or dip coating or a printing process such as screen printing or ink-jet printing, onto the surface of the material (including the barrier layer 63ya), on which the light emitting region 63z is to be formed, then carrying out annealing treatment.

In the foregoing explanation of the solar cell 301, an embodiment has been described in which a plurality of stacked layers 73 are successively arranged. However, the photoelectric conversion device of the invention having a wavelength converting region 63 is not limited to this embodiment. The photoelectric conversion device of the invention may also be implemented in a form, in which a wavelength converting region 63 is disposed at each interface between an n layer and a p layer that are adjacent to each other.

The energy gaps of the n layer 71 and the p layer 72 may be set to, for example, at least 0.9 eV and not more than 3.0 eV. A material similar to the photoelectric conversion region 40 may be used for the n layers 71 and the p layers 72. The thicknesses of the n layers 71 and the p layers 72 may be set to about 100 nm. The n layers 71 and the p layers 72 may be fabricated by methods similar to those for the photoelectric conversion region 40.

Figure 8A:
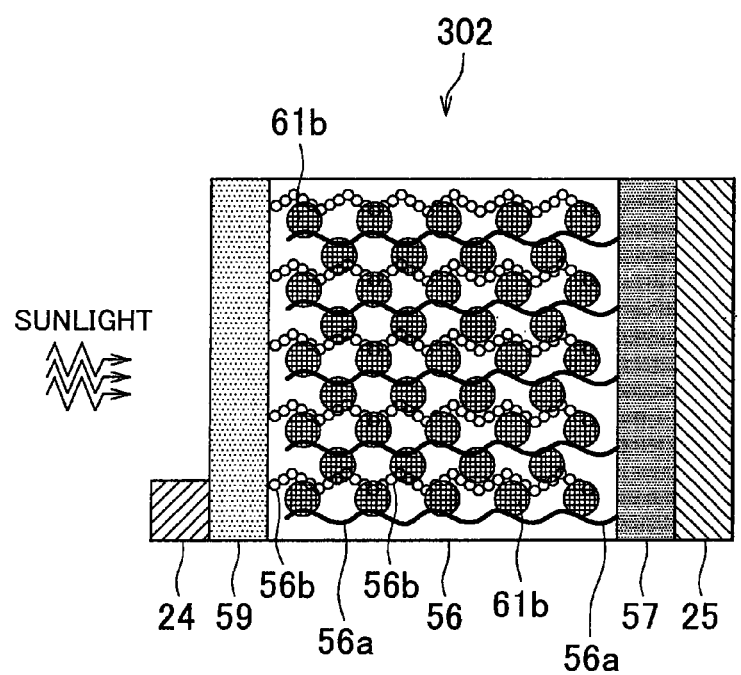
FIG. 8A is a sectional view of a solar cell according to a fifth embodiment of the invention.

FIG. 8A is a sectional view showing a solar cell 302 according to another embodiment of the invention. The lateral direction in FIG. 8A is the direction of travel of light. In FIG. 8A, a plurality of wavelength converting particles 61b, a plurality of p-type materials 56a, and a plurality of n-type materials 56b are schematically shown. In FIG. 8A, elements similar to those in the above-described solar cell 300 are denoted by the same symbols as are used in FIG. 3, and explanations of those elements are omitted below as appropriate.

As shown in FIG. 8A, the solar cell 302 has an n layer 59 and a p layer 57, and also has a mixed p-n junction layer 56 disposed between the n layer 59 and the p layer 57. A surface electrode 24 is connected to the n layer 59, and a back electrode 25 is connected to the p layer 57. In the mixed p-n junction layer 56, a plurality of p-type materials 56a that function as p-type semiconductors and a plurality of n-type materials 56b that function as n-type semiconductors are mixed at a nanoscale level and have a bulk heterojunction structure with p-n junction interfaces dispersed throughout the mixed p-n junction layer 56. In addition, a plurality of wavelength converting particles 61b are dispersed in the mixed p-n junction layer 56. At least some of the p-type materials 56a within the mixed p-n junction layer 56 are in mutual contact, and some of the p-type materials 56a are in contact with the p layer 57. Likewise, at least some of the n-type materials 56b within the mixed p-n junction layer 56 are in mutual contact, and some of the n-type materials 56b are in contact with the n layer 59. In the solar cell 302, the energy gaps of the semiconductor materials making up the n layer 59, the p-type material 56a, the n-type material 56b and the p layer 57 are about 0.1 eV smaller than the energy of the monochromatic light generated in a light emitting region 61z of the wavelength converting particles 61b. In the solar cell 302, light that is not absorbed by the n layer 59, p-type material 56a, n-type material 56b or p layer 57 is absorbed by the wavelength converting particles 61b, and monochromatic light that are generated by the light emitting region 61z in the wavelength converting particles 61b is absorbed by the n layer 59, p-type material 56a, n-type material 56b and p layer 57.

When light falls on the solar cell 302, the light passes through the n layer 59. The light that h¾s not been absorbed by the n layer 59 reaches the wavelength converting particles 61 b. When the light reaches the wavelength converting particles 61b, that light having an energy larger than the energy gap of a carrier generating region 61 x is absorbed, creating electrons and holes having various energies in the carrier generating region 61 x. Of the electrons and holes that are generated, those electrons and holes having energies that correspond to discrete energy levels formed in the conduction band or valence band of a quantum well layer 61 yb are able to reach the light emitting region 61 z via discrete energy levels in the quantum well layer 61 yb by tunneling conduction, and recombine at the light emitting region 61 z, becoming monochromatic light. Of the electrons generated at the carrier generating region 61 x, some of the electrons having energies that differ from the discrete energy levels formed in the conduction bands of the quantum well layer 61 yb, by carrying out mutual energy transfer with other electrons generated at the carrier generating region 61x, come to have the same energy as discrete energy levels formed in the conduction band of the quantum well layer 61 yb. Similarly, of the holes generated at the carrier generating region 61 x, some of the holes having energies that differ from the discrete energy levels formed in the valence bands of the quantum well layer 61 yb, by carrying out mutual energy transfer with other holes generated at the carrier generating region 61x, come to have the same energy as discrete energy levels formed in the valence band of the quantum well layer 61 yb. The electrons and holes that have thus come to have the same energy as discrete energy levels formed in the conduction band and valence band of the quantum well layer 61 yb are able, by tunneling conduction, to reach the light emitting region 61 z via discrete energy levels of the quantum well layer 61 yb and recombine at the light emitting region 61 z, becoming monochromatic light.

The monochromatic light generated in the light emitting region 61z is absorbed by the p-type material 56a or n-type material 56b that are present, together with the wavelength converting particles 61b, within the mixed p-n junction layer 56. The energy gaps of the semiconductor materials making up the p-type material 56a and the n-type material 56b are about 0.1 eV lower than the energy of the monochromatic light generated in the light emitting region 61z. Hence, the monochromatic light generated in the light emitting region 61z is absorbed by the p-type material 56a or n-type material 56b, and electrons and holes are generated in the p-type material 56a or n-type material 56b. Since the difference between the energy of the monochromatic light and the energy gaps of the semiconductor materials making up the p-type material 56a and the n-type material 56b is only about 0.1 eV, the electrons and holes thus generated are separated, with substantially no loss of energy, by an internal electrical field formed by the p-n junction of the p-type material 56a and the n-type material 56b, so that the electrons move through the n-type material 56b to the n layer 59 and are collected at the surface electrode 24 connected to the n layer 59, and the holes move through the p-type material 56a to the p layer 57 and are collected at the back electrode 25 connected to the p layer 57.

With this solar cell 302 that thus absorbs light and collects electrons and holes, it becomes possible to greatly expand the wavelength range of the light utilized during conversion to electricity. Moreover, a purpose of the wavelength converting particles 61b is to allow the carriers that are generated in the carrier generating region 61x to recombine at a light emitting region 61z; it is not intended to extract the generated carriers directly to the exterior. Therefore, in the wavelength converting particles 61b, unlike in conventional hot carrier solar cells that use a quantum structure, there is no need to have the carriers move all the way to the electrode, so that it is made possible to markedly reduce the energy loss during movement. In particular, by controlling the diameter of the carrier generating region 61x, and thereby setting the movement length of carriers from the generation in the carrier generating region 61x until they reach the carrier selective transfer region 61y to about 10 nm or less, it becomes possible to greatly reduce energy loss during movement. Moreover, by employing an embodiment in which a semiconductor material is used for the carrier generating region 61x, it becomes possible to considerably broaden the wavelength range of light that can be utilized for generating carriers as compared to conventional up-conversion solar cells that use fluorescent materials. In addition, in the solar cell 302 in which the monochromatic light generated in the wavelength converting particles 61b is absorbed by the p-type material 56a or the n-type material 56b, the energy of the light input to the p-type material 56a or n-type material 56b is fixed. Thus, the energy loss is easily reduced by using for the p-type material 56a or the n-type material 56b a semiconductor material having an energy gap corresponding to the fixed energy. Accordingly, also with this solar cell 302 it is possible to increase the photoelectric conversion efficiency. In this solar cell 302 as well, the photoelectric conversion efficiency is easily increased by increasing the efficiency of the wavelength converting particles 61b that convert light to monochromatic light.

In this solar cell 302, electron donor molecules such as polyhexylthiophene (P3HT), polyalkylthiophene (P3AT) and pentacene may be used as the p-type material 56a. The p-type material 56a may be rendered into a particulate, molecular or polymeric form. Electron acceptor molecules such as fullerene and fullerene derivatives (PCBM) may be used as the n-type material 56b. The n-type material 56b may be rendered into a particulate, molecular or polymeric form. Also, the n layer 59 may be composed of a material similar to the n layer 51, and the p layer 57 may be composed of a material similar to the p layer 53.

No particular limitation is imposed on the mixing ratio among the wavelength converting particles 61b, p-type material 56a and n-type material 56b included in the mixed p-n junction layer 56. The weight ratio may be set as follows: the wavelength converting particles 61b: the p-type material 56a: the n-type material 56b=2:1:1. The mixing ratio of the wavelength converting particles 61b, the p-type material 56a, and the n-type material 56b may be suitably varied within a range such that each proportion is from 0.1 to 10.

The energy gaps of the n layer 59 and the p layer 57 may be set to, for example, at least 0.9 eV and not more than 3.0 eV. Materials similar to those for the above-described photoelectric conversion region 40 may be used for the n layer 59 and the p layer 57. The thicknesses of the n layer 59 and the p layer 57 may be set to, for example, about 100 nm, and the n layer 59 and the p layer 57 may be fabricated by a method similar to that used for the above-described photoelectric conversion region 40.

An embodiment of a method of fabricating the solar cell 302 thus constructed will be described below. Fabrication of the solar cell 302 involves first the formation of, on an available substrate such as glass or plastic and by a conventional method such as vapor deposition, a back electrode 25 made of a metal material such as Al, Ag or Au or a transparent electrically conductive film such as ITO, aluminum-doped zinc oxide (AZO) or fluorine-doped tin oxide (FTO). Next, a p layer-forming composition prepared by mixing about 1 to 10 wt % of a p-type semiconductor material for the p layer 57 with an organic solvent (e.g., xylene, chloroform, chlorobenzene; the same applies below) is applied onto the surface of the back electrode 25 by a method such as spin coating or dip coating. The applied composition is then held at room temperature for a period of from several tens of minutes to about 2 hours, or in a drying oven at about 100° C. for about 10 minutes, causing the organic solvent to evaporate, thereby forming the p layer 57. Once the p layer 57 has thus been formed, a mixed p-n junction layer-forming composition is prepared by adding wavelength converting particles 61b, p-type material 56a and n-type material 56b in a total amount of about 1 to 10 wt % to an organic solvent. The wavelength converting particles 61b may be fabricated by the method described above. Next, the mixed p-n junction layer-forming composition is applied onto the surface of the p layer 57 by a method such as spin coating or dip coating. The applied composition is then held at room temperature for a period of from several tens of minutes to about 2 hours, or in a drying oven at about 100° C. for about 10 minutes, causing the organic solvent to evaporate, thereby forming the mixed p-n junction layer 56. Once the mixed p-n junction layer 56 has thus been formed, an n layer 59 composed of ZnO, $SnO_2$, $TiO_2$ or the like is formed on the surface of the mixed p-n junction layer 56 by a conventional method such as vapor deposition. Alternatively, an n layer-forming composition prepared by mixing about 1 to 10 wt % of an n-type semiconductor material for the n layer 59 with an organic solvent is applied onto the surface of the mixed p-n junction layer 56 by a method such as spin coating or dip coating. The applied composition is then held at room temperature for a period of from several tens of minutes to about 2 hours, or in a drying oven at about 100° C. for about 10 minutes, causing the organic solvent to evaporate, thereby forming the n layer 59. Once the n layer 59 has thus been formed, a surface electrode 24 composed of a comb-shaped metallic material such as Al, Ag or Au, or a transparent electrically conductive film such as indium tin oxide (ITO), aluminum-doped zinc oxide (AZO) or fluorine-doped tin oxide (FTO), is formed on the surface of the n layer 59 by a conventional method such as vacuum deposition. This is one process that may be used to fabricate the solar cell 302. During production of the solar cell 302, the drying atmosphere is preferably an inert gas atmosphere such as nitrogen gas or argon gas.

Figure 8B:
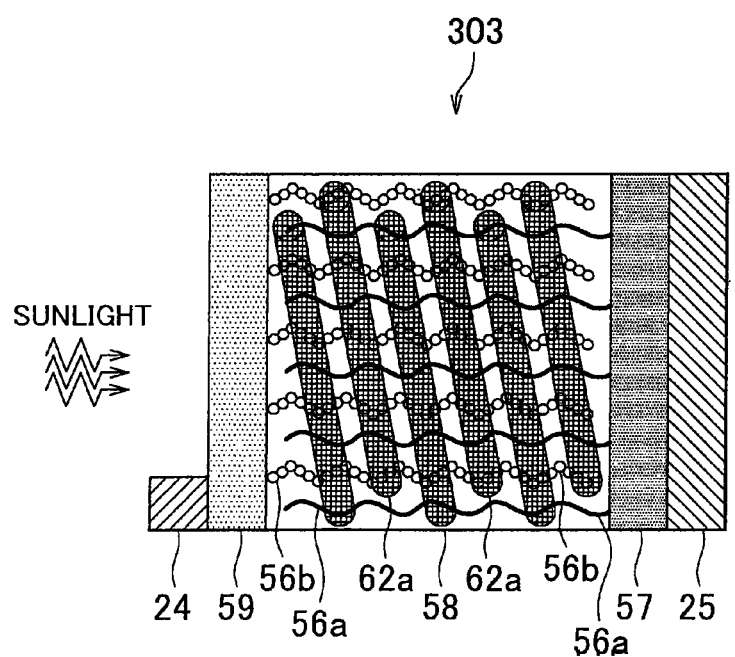
FIG. 8B is a sectional view of a solar cell according to a sixth embodiment of the invention.

FIG. 8B is a sectional view showing a solar cell 303 according to another embodiment of the invention. The lateral direction in the plane of the diagram in FIG. 8B is the direction of travel of light. FIG. 8B schematically shows a plurality of wavelength converting fibers 62a, a plurality of p-type materials 56a, and a plurality of n-type materials 56b. In FIG. 8B, elements similar to those in the above-described solar cell 302 are denoted by the same symbols as are used in FIG. 8A, and explanations of those elements are omitted below as appropriate.

As shown in FIG. 8B, the solar cell 303 has an n layer 59 and a p layer 57, and also has a mixed p-n junction layer 58 disposed between the n layer 59 and the p layer 57. The p-type materials 56a and the n-type materials 56b are mixed at a nanoscale level in the mixed p-n junction layer 58 and have a bulk heterojunction structure with p-n junction interfaces dispersed throughout the mixed p-n junction layer 58. In addition, a plurality of wavelength converting fibers 62a are dispersed in the mixed p-n junction layer 58. At least some of the p-type materials 56a within the mixed p-n junction layer 58 are in mutual contact, and some of the p-type materials 56a are in contact with the p layer 57. Likewise, at least some of the n-type materials 56b within the mixed p-n junction layer 58 are in mutual contact, and some of the n-type materials 56b are in contact with the n layer 59. In the solar cell 303, the energy gaps of the semiconductor materials making up the n layer 59, the p-type material 56a, the n-type material 56b and the p layer 57 are about 0.1 eV smaller than the energy of the monochromatic light generated in the light emitting region 62z of the wavelength converting fibers 62a. In the solar cell 303, light that is not absorbed by the n layer 59, p-type material 56a, n-type material 56b or p layer 57 is absorbed by the wavelength converting fibers 62a, and the monochromatic light that is generated by the light emitting regions 62z of the wavelength converting fibers 62a is absorbed by the n layer 59, p-type material 56a, n-type material 56b and p layer 57. That is, except wavelength converting fibers 62a being dispersed instead of wavelength converting particles 61b, this solar cell 303 has a construction that is similar to that of the above-described solar cell 302.

As mentioned above, the wavelength converting fibers 62a of the present embodiment, like the wavelength converting particles 61b of the preceding embodiment, are able to generate monochromatic light. Therefore, as in the case of the solar cell 302r, it is possible to increase the photoelectric conversion efficiency with the solar cell 303 of the present embodiment in which wavelength converting fibers 62a are dispersed instead of wavelength converting particles 61b. In this solar cell 303 as well, the photoelectric conversion efficiency is easily increased by increasing the efficiency of the wavelength converting fibers 62a that convert light into monochromatic light. Except the use of wavelength converting fibers 62a instead of wavelength converting particles 61b, the solar cell 303 of the present embodiment having such features may be fabricated by methods similar to those for the above-described solar cell 302.

Figure 9:
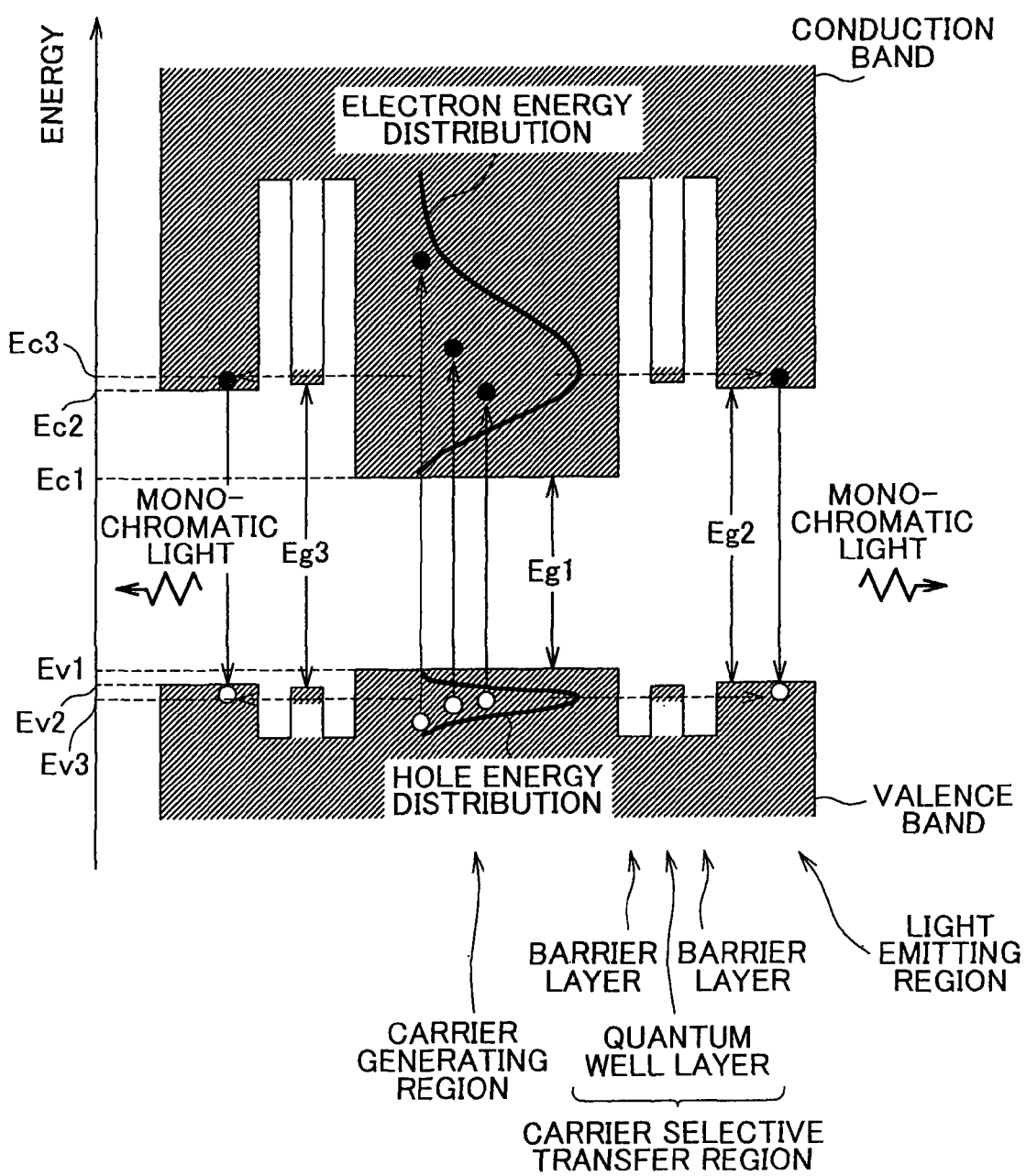
FIG. 9 is a diagram showing a band structure of the wavelength converting material of the solar cells according to the above embodiments of the invention.

FIG. 9 is a diagram showing the band structure of wavelength converting particles 61b, wavelength converting fibers 62a and wavelength converting regions 63 (these are sometimes referred to collectively below as "wavelength converting materials"). The band structure of wavelength converting materials will be described below with reference to FIGS. 4, 5B, 6 and 9.

As shown in FIG. 9, a wavelength converting material has a difference (energy gap) Eg1 between the energy Ec1 at the bottom edge of the conduction band and the energy Ev1 at the top edge of the valence band for the semiconductor material making up the carrier generating region, and has a difference (energy gap) Eg2 between the energy Ec2 at the bottom edge of the conduction band and the energy Ev2 at the top edge of the valence band for the semiconductor material making the light emitting region. In addition, the energy of the lowest discrete energy level in the conduction band for the material making up the carrier selective transfer region (specifically, the semiconductor material making up the quantum well layer; the same applies below) is Ec3, the energy of the lowest discrete energy level in the valence band for the same material is Ev3, and the energy gap for the material making up the carrier selective transfer region is Eg3. The wavelength converting material having the band structure shown in FIG. 9 satisfies the following relationships:

$$Eg1 < Eg2 \leq Eg3$$

$$Ec1 < Ec2 \leq Ec3$$

$$Ev3 \leq Ev2 \leq Ev1$$

$$Ec3 - Ec2 \cong 0.05 \text{ eV}$$

$$|Ev2 - Ev3| \cong 0.05 \text{ eV}$$

When light reaches the wavelength converting material, that light having an energy larger than the energy gap Eg1 for the carrier generating region is absorbed, and electrons and holes having various energies are generated in the carrier generating region. Discrete energy levels are formed at the quantum well layer of the carrier selective transfer region, and the electrons and holes generated in the carrier generating region move to the light emitting region via these discrete energy levels. Of the electrons that are generated in the carrier generating region, those electrons that have an energy that corresponds to the lowest discrete energy level Ec3 in the conduction band for the quantum well layer, and those electrons that have come to have an energy that corresponds to this lowest discrete energy level Ec3 as a result of carrying out energy transfer with other electrons, reach the light emitting region via that discrete energy level of the quantum well layer by tunneling conduction. At the same time, of the holes that are generated in the carrier generating region, those holes that have an energy that corresponds to the lowest discrete energy level Ev3 in the valence band for the quantum well layer, and those holes that have come to have an energy that corresponds to this lowest discrete energy level Ev3 as a result of carrying out energy transfer with other holes, reach the light emitting region via that discrete energy level of the quantum well layer by tunneling conduction. The electrons and holes that have thus moved to the light emitting region recombine at the light emitting region, becoming monochromatic light having energy Eg2.

In the wavelength converting material, by adjusting the material selection and composition for the barrier layers and the quantum well layers, and by also adjusting the thickness of the quantum well layer, it is possible to adjust Ec3 and Ev3 at will. By adjusting the Ec3 and Ev3, the energies of the electrons and holes that move to the light emitting region can be adjusted. Moreover, by adjusting Ec3 and Ev3, and also adjusting the material selection and composition of the light emitting region, it is possible to freely adjust the energy Eg2 of the monochromatic light.

In the wavelength converting material, because discrete energy levels are formed in the conduction band and the valence band for the quantum well layer, the energy loss is easily reduced. Moreover, by setting energy levels so as to satisfy the relations, $Ec3-Ec2 \cong 0.05$ eV and $|Ev2-Ev3| \cong 0.05$ eV, energy loss in the light emitting region is easily reduced.

Figure 10:
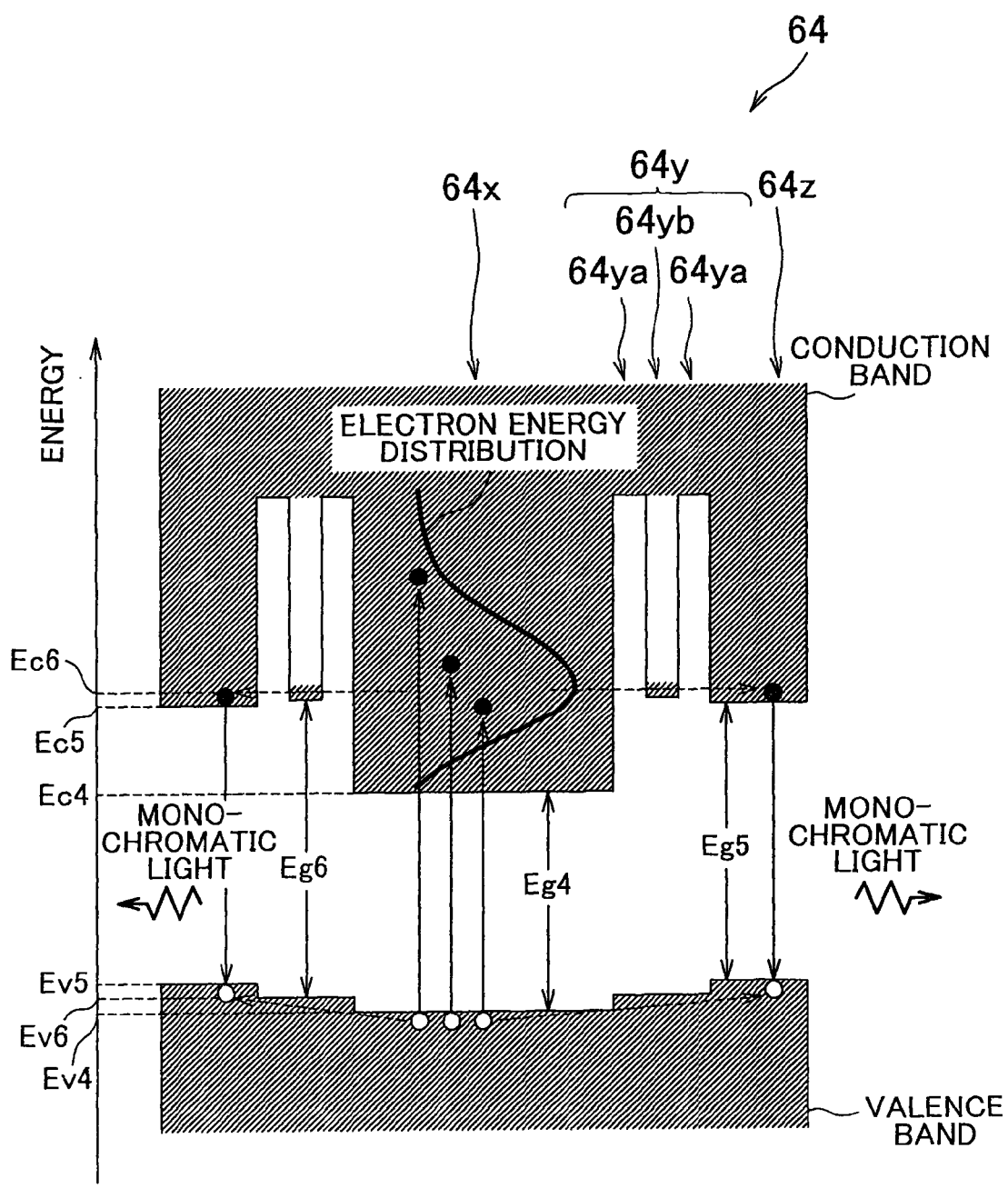
FIG. 10 is a diagram showing a band structure of the wavelength converting material of the solar cells according to the above embodiments of the invention.

FIG. 10 is a diagram, corresponding to FIG. 9, which shows a band structure of wavelength converting particles, wavelength converting fibers, and wavelength converting regions having a multilayer film structure that may be used in the wavelength converting region of the invention (these are sometimes referred to collectively below as "the wavelength converting material 64").

The wavelength converting material 64 has, in order from the center side outward, a carrier generating region 64x, a carrier selective transfer region 64y, and a light emitting region 64z. The carrier selective transfer region 64y has, from the carrier generating region 64x side toward the light emitting region 64z side, a barrier layer 64ya, a quantum well layer 64yb, and a barrier layer 64ya. The carrier generating region 64x, carrier selective transfer region 64y and light emitting region 64z are each composed of semiconductor materials. In the wavelength converting material 64, the difference (energy gap) between the energy Ec4 at the bottom edge of the conduction band and the energy Ev4 at the top edge of the valence band for the semiconductor material making up the carrier generating region 64x is Eg4, and the difference (energy gap) between the energy Ec5 at the bottom edge of the conduction band and the energy Ev5 at the top edge of the valence band for the semiconductor material making up the light emitting region 64z is Eg5. In addition, the energy of the lowest discrete energy level in the conduction band for the semiconductor material making up the quantum well layer 64yb is Ec6, the energy at the top edge of the valence band for the same material is Ev6, and the energy gap for the semiconductor material making up the quantum well layer 64yb is Eg6. The wavelength converting material 64 satisfies the following relationships:

$Eg4 < Eg5 \leq Eg6$ $EG4 < Ec5 \leq Ec6$ $Ev4 \leq Ev6 \leq Ev5$ $Ec6-Ec5 \cong 0.05$ eV $|Ev5-Ev6| \cong 0.05$ eV $|Ev6-Ev4| \cong 0.05$ eV When light reaches the wavelength converting material 64, that light having an energy larger than the energy gap Eg4 of the carrier generating region 64x is absorbed, and electrons and holes having various energies are generated in the carrier generating region 64x. In the quantum well layer 64yb, discrete energy levels are formed only on the conduction band side. Therefore, of the electrons generated in the carrier generating region 64x, those electrons that have an energy that corresponds to the lowest discrete energy level Ec6 in the conduction band for the quantum well layer 64yb and those electrons that have come to have an energy that corresponds to this lowest discrete energy level Ec6 as a result of carrying out energy transfer with other electrons, reach the light emitting region 64z via that discrete energy level of the quantum well layer 64yb by tunneling conduction. By contrast, discrete energy levels are not formed in the valence band of the carrier selective transfer region 64y. Therefore, there is no quantum confinement effect on the holes generated in the carrier generating region 64x, and therefore the holes generated in the carrier generating region 64x immediately move to the light emitting region 64z via the carrier selective transfer region 64y. The electrons and holes that have moved to the light emitting region 64z recombine at the light emitting region 64z, becoming monochromatic light having energy Eg5.

In the wavelength converting material 64, discrete energy levels are formed on the conduction band side for the quantum well layer 64yb, but discrete energy levels are not formed on the valence band side. Hence, of the electrons and holes that are generated in the carrier generating region 64x, there is the quantum confinement effect on the electrons, but there is no, quantum confinement effect on the holes. Therefore, the wavelength converting material 64 has a function of confining only the electrons to make the electrons interact with each other. Because the holes generated in the carrier generating region 64x move immediately to the light emitting region 64z, the hole density in the carrier generating region 64x greatly decreases. That is, since it is possible to reduce the number of holes that recombine with electrons in the carrier generating region 64x, the lifetime of hot carriers can be extended. Also, in the wavelength converting material 64 where discrete energy levels are not formed on the valence band side, because it is difficult to make holes interact with each other, the energy loss of the holes tends to become larger than in a wavelength converting material having the band structure shown in FIG. 9. However, since the energy distribution width of the holes in the carrier generating region 64x is smaller than the energy distribution width of the electrons, the influence of this energy loss is slight. With such a wavelength converting material 64, the energy loss can be reduced by allowing the electrons to interact with each other. Hence, the photoelectric conversion device according to the invention that uses this wavelength converting material 64 also makes it possible to increase the photoelectric conversion efficiency.

In the wavelength converting material 64, by adjusting the material selection and composition for the barrier layers 64ya and the quantum well layer 64yb, and by also adjusting the thickness of the quantum well layer 64yb, Ec6 can be adjusted at will. By adjusting Ec6, the energies of the electrons and holes that move to the light emitting region can be adjusted. Moreover, by adjusting Ec6 and also adjusting the material selection and composition of the light emitting region 64z, it is possible to adjust the energy Eg5 of the monochromatic light at will.

In the wavelength converting material 64, by setting energy levels so as to satisfy the relations, $Ec6-Ec5 \cong 0.05$ eV, $|Ev5-Ev6| \cong 0.05$ eV, and $|Ev6-Ev4| \cong 0.05$ eV, the energy lost when the carriers move from the carrier generating region 64x to the light emitting region 64z is easily reduced.

Also, in the wavelength converting material 64, since there is no need to form discrete energy levels on the valence band side for the carrier selective transfer region 64y, the optimal value of Ec6 is easily adjusted, and the material options readily increase. Therefore, this wavelength converting material 64 has a tendency to be easier to fabricate than wavelength converting materials having the band structure shown in FIG. 9.

For example, the wavelength converting material 64 having the band structure shown in FIG. 10 can be fabricated by respectively using InAs for the carrier generating region 64x, GaAs for the barrier layers 64ya, and GaAsSb for the quantum well layer 64yb, and by using a semiconductor material having an energy gap that is about 0.1 eV smaller than that of GaAsSb for the light emitting region 64z. Alternatively, the wavelength converting material 64 having the band structure shown in FIG. 10 can be fabricated by respectively using PbS for the carrier generating region 64x, ZnS for the barrier layers 64ya, and CdTe for the quantum well layer 64yb, and by using a semiconductor material having an energy gap that is about 0.1 eV smaller than that of CdTe for the light emitting region 64z. The wavelength converting material 64 having the band structure shown in FIG. 10 may be fabricated by respectively using CdSe for the carrier generating region 64x, ZnSe for the barrier layers 64ya, and CdS for the quantum well layer 64yb, and by using a semiconductor material having an energy gap that is about 0.1 eV smaller than that of CdS for the light emitting region 64z. In the wavelength converting material 64, adjustment of the energy band can be carried out by doping the carrier generating region 64x or the quantum well layer 64yb with an n-type element.

In the foregoing explanation concerning the wavelength converting material 64, an embodiment has been described in which, by modifying the combination of materials in, for example, the carrier generating region 64x, the barrier layers 64ya and the quantum well layer 64yb, discrete energy levels are not formed on the valence band side of the carrier selective transfer region 64y, as a result of which the holes generated in the carrier generating region 64x immediately move to the light emitting region 64z. In this invention, embodiments in which holes generated in the carrier generating region are allowed to immediately move to the light emitting region are not limited to the form of the wavelength converting material 64. For example, when wavelength converting particles or wavelength converting fibers are fabricated by the methods described above, lattice defects such as vacancies are sometimes present at the surface of the wavelength converting particles or wavelength converting fibers. When the proportion of the wavelength converting particle or wavelength converting fiber surface area occupied by the lattice defect sites is set to, for example, at least about 1% and not more than about 20%, there can be obtained an embodiment in which discrete energy levels are formed on the conduction band side of the quantum well layer and discrete energy levels are not formed on the valence band side of the quantum well layer. Embodiments of the photoelectric conversion device of the invention that include such wavelength converting particles or wavelength converting fibers may also be adopted.

Figure 11:
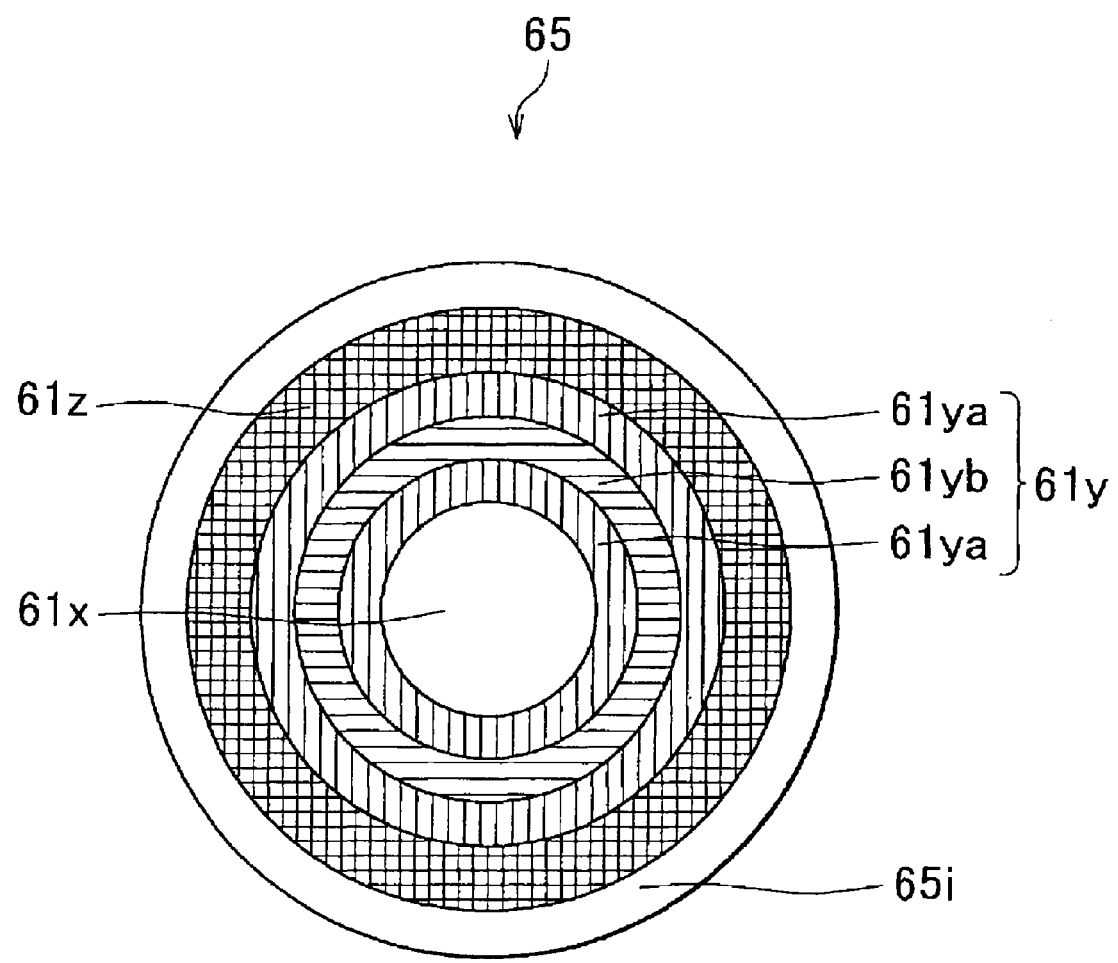
FIG. 11 is a sectional view of a modification of a wavelength converting region.

FIG. 11 is a sectional view showing an embodiment of a wavelength converting region 65. In FIG. 11, elements similar to those in the above-described wavelength converting particles 61b are denoted by the same symbols as are used in FIG. 4, and explanations of those elements are omitted below as appropriate. As shown in FIG. 11, the wavelength converting region 65 has at the center thereof a carrier generating region 61x, and includes, arranged concentrically from the center outward, a carrier generating region 61x, a carrier selective transfer region 61y, a light emitting region 61z, and a transparent, electrically insulating region 65i. That is, the wavelength converting region 65 is in a form where the surface of the light emitting region 61z in a wavelength converting particle 61b is covered with a transparent insulating region 65i. By covering the surface of the light emitting region 61z with a transparent insulating region 65i, it is possible to reduce defects at the surface of the light emitting region 61z. By reducing defects, it is possible to reduce the electrons and holes that are captured by the defects and do not combine, so that it is made possible to increase the light emission efficiency of the light emitting region 61z. Therefore, by employing an embodiment having such a wavelength converting region 65, it becomes possible to increase the photoelectric conversion efficiency.

In the wavelength converting region 65, in order to keep a tunneling current from occurring while at the same time ensuring that the proportion of the volume of the carrier generating region 61x to the whole of the wavelength converting region 65 does not become too small, the thickness of the transparent insulating region 65i may be set to, for example, at least 2 nm and not more than 100 nm. In order to achieve an embodiment that can be easily fabricated, it is preferable to set the thickness of the transparent insulating region 65i to at least 10 nm and not more than 50 nm.

The transparent insulating region 65i may be, for example, $SiO_2$ or $SiN_x$, or may be resin such as polystyrene, polyvinyl alcohol, polypropylene, or a methacrylate polymer (acrylic). A transparent insulating region 65i composed of such a material can be fabricated by a vacuum deposition process that includes ion plating, by a vapor phase growth process such as sputtering, or by chemical synthesis such as a sol-gel process or solvothermal synthesis.

In the foregoing description relating to the wavelength converting region 65, an embodiment in which the surface of the light emitting region is covered with a transparent insulating material has been mentioned by way of illustration. However, wavelength converting regions that can be employed in the photoelectric conversion device of the invention are not limited to this embodiment. The surface of the light emitting region may be covered with an available transparent semiconductor material having an energy gap of a size that does not absorb the light to be absorbed by the carrier generating region (e.g., at least 3.0 eV, and preferably at least 4.0 eV).

Moreover, a wavelength converting region 65 in a particulate form has been illustrated as an example in the foregoing description of the wavelength converting region 65. However, the wavelength converting region covered with an insulating material and/or a semiconductor material that does not absorb the light to be absorbed by the carrier generating region is not limited to this form, and may also be in a linear form such as the wavelength converting fibers 62a or in a multilayer film form such as the wavelength converting region 63. In the case of a linear form, the surface of the light emitting region 62z should be covered with an insulating material and/or a semiconductor material that does not absorb the light to be absorbed by the carrier generating region. In the case of a multilayer film form, a layer composed of an insulating material and/or a semiconductor material that does not absorb the light to be absorbed by the carrier generating region should be provided on the outer side of each of the light emitting regions 63z by covering the surfaces of the light emitting regions 63z with an insulating material and/or a semiconductor material that does not absorb the light to be absorbed by the carrier generating region.

Figure 12A:
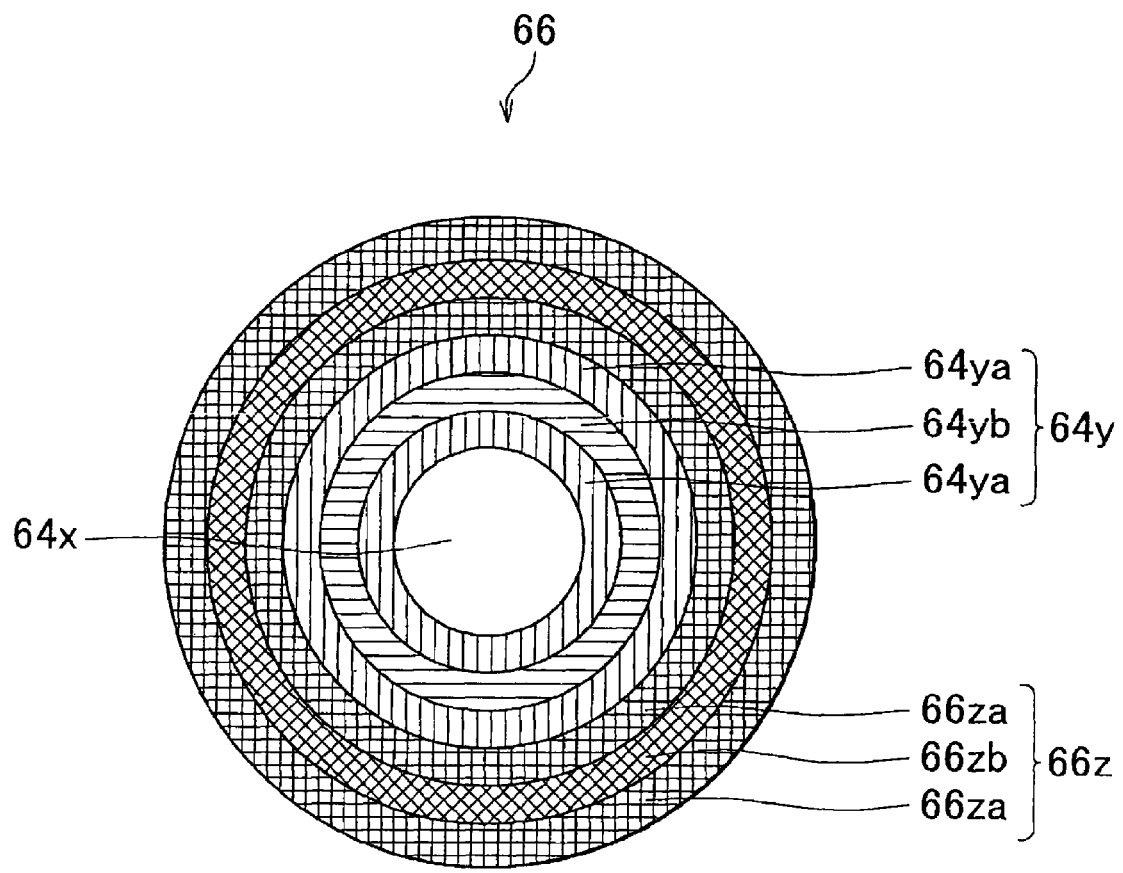
FIG. 12A is a sectional view of another modification of a wavelength converting region.
Figure 12B:
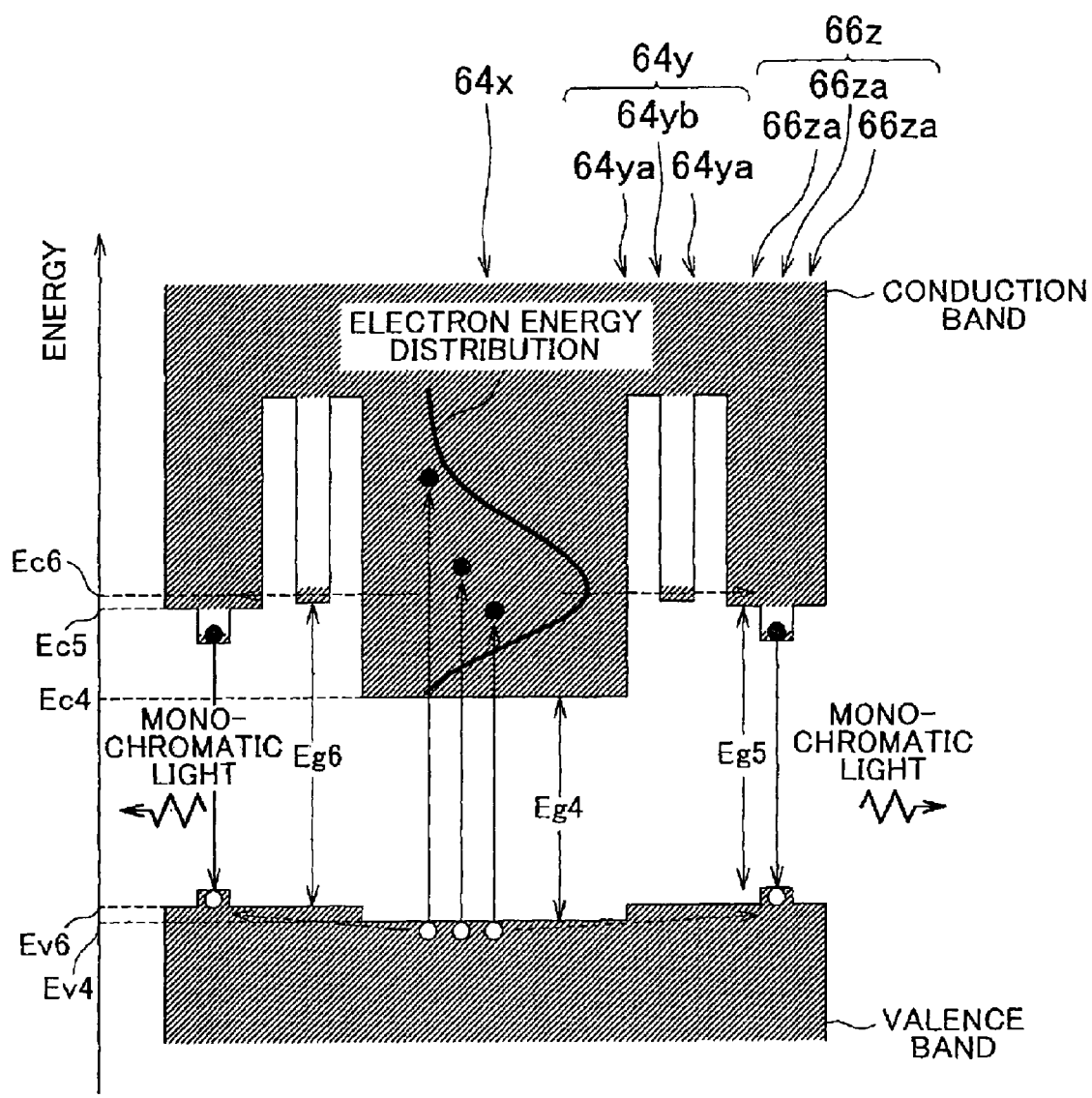
FIG. 12B is a diagram showing a band structure of the wavelength converting region shown in FIG. 12 A.

FIG. 12A is a sectional view showing an embodiment of a wavelength converting region 66. FIG. 12B is a diagram showing the band structure of the wavelength converting region 66. In FIGS. 12A and 12B, elements similar to those in the above-described wavelength converting material 64 are denoted by the same symbols as are used in FIG. 10, and explanations of those elements are omitted below as appropriate.

As shown in FIG. 12A, the wavelength converting region 66 has a carrier generating region 64x at the center and has, concentrically from the center outward, a carrier generating region 64x, a carrier selective transfer region 64y, and a light emitting region 66z. The light emitting region 66z has, concentrically from the carrier selective transfer region 64y side outward, a barrier layer 66za, a quantum well layer 66zb, and a barrier layer 66za. The barrier layers 66za and the quantum well layer 66zb are composed of semiconductor materials. That is, the wavelength converting region 66 is in a form that uses a different light emitting region 66z instead of the light emitting region 64z in the wavelength converting material 64. As shown in FIG. 12B, within the wavelength converting region 66, the bottom edge of the conduction band for the barrier layers 66za is positioned above the bottom edge of the conduction band for the quantum well layer 66zb, and the top edge of the valence band for the barrier layers 66za is positioned below the top edge of the valence band for the quantum well layer 66zb.

When light reaches the wavelength converting region 66, that light having a larger energy than the energy gap Eg4 of the carrier generating region 64x is absorbed, creating electrons and holes having various energies in the carrier generating region 64x. Of the electrons generated in the carrier generating region 64x, those electrons that have an energy that corresponds to the lowest discrete energy level Ec6 in the conduction band for the quantum well layer 64yb and those electrons that have come to have an energy that corresponds to the lowest discrete energy level Ec6 by carrying out energy transfer with other electrons, reach the light emitting region 66z via these discrete energy levels of the quantum well layer 64yb by tunneling conduction. By contrast, since there is no quantum confinement effect on the holes generated at the carrier generating region 64x, the holes generated at the carrier generating region 64x immediately move to the light emitting region 66z through the carrier selective transfer region 64y. Here, in the light emitting region 66z, the bottom edge of the conduction band for the barrier layers 66za is positioned above the bottom edge of the conduction band for the quantum well layer 66zb, and the top edge of the valence band for the barrier layers 66za is positioned below the top edge of the valence band for the quantum well layer 66zb. Hence, the electrons and holes that move to the light emitting region 66z collect and combine at the quantum well layer 66zb, becoming monochromatic light.

In this wavelength converting region 66, it is possible to collect electrons and holes at the quantum well layer 66zb, so that it is made easy to combine the electrons and holes. By employing such an embodiment, the time required until the electrons and holes combine at the light emitting region 66z can be reduced, so that it is made possible to allow the electrons and holes to combine and generate monochromatic light before they undergo annihilation by non-radiative recombination. That is, with the wavelength converting region 66, it becomes possible to reduce energy loss and increase the light emitting efficiency.

In the wavelength converting region 66, a semiconductor material like that for the quantum well layer 64yb may be used for the barrier layers 66za and the quantum well layer 66zb, and the band gap difference between the semiconductor material making up the barrier layers 66za and the semiconductor materials making up the quantum well layer 66zb may be set to at least about 0.05 eV and not more than about 0.3 eV. Also, the thickness of the barrier layers 66za may be set to at least 2 nm in order to, for example, make it easier to suppress electron and hole combination at defects in the surface of the wavelength converting region 66, and may be set to not more than about 20 nm so as to, for example, keep the proportion of the carrier generating region 64x relative to the wavelength converting region 66 from becoming too small. Also, the thickness of the quantum well layer 66zb may be set to at least about 2 nm and not more than about 10 nm so as to, for example, make it possible to exhibit quantum confinement effects. If the wavelength converting region 66 is in a particulate form, the light emitting region 66z having thus constituted barrier layers 66za and quantum well layer 66zb may be fabricated by a method similar to that used for the above-described carrier selective transfer region 61y. If the wavelength converting region 66 is in a linear form, the light emitting region 66z may be fabricated by a method similar to that used for the above-described carrier selective transfer region 62y.

In the foregoing description of the invention, embodiments provided with a carrier generating region, a carrier selective transfer region, and a wavelength converting region having a light emitting region (wherein the carrier selective transfer region and the light emitting region are separately constructed, and both are connected to the wavelength converting region) have been cited. However, the photoelectric conversion device of the invention is not limited to such embodiments. The photoelectric conversion device of the invention may be implemented by an embodiment provided with a wavelength converting region having a carrier generating region and a light emitting region that also functions as a carrier selective transfer region (a wavelength converting region having a light emitting region that functions as both a carrier selective transfer region and a light emitting region). Accordingly, a wavelength converting region in a form having a carrier generating region and a light emitting region that functions also as a carrier selective transfer region will be described below.

Figure 13A:
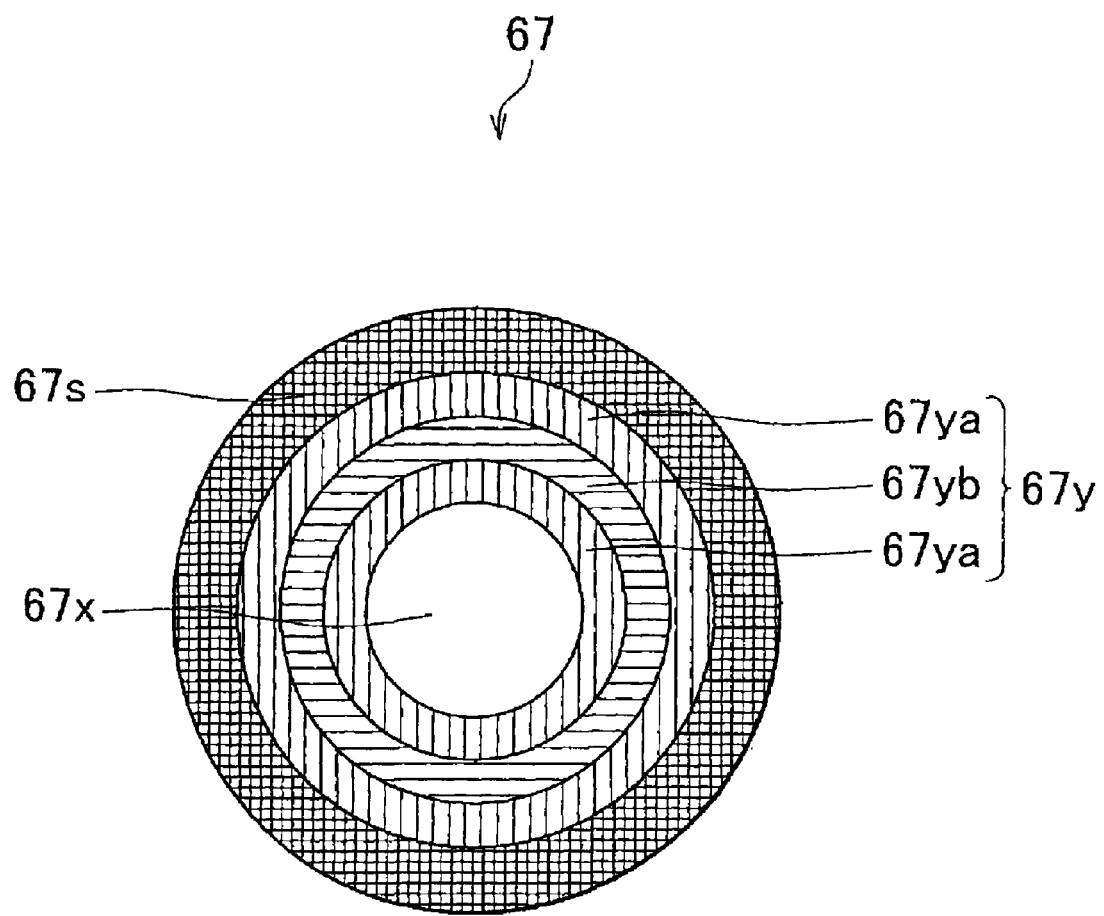
FIG. 13A is a sectional view of a modification of a wavelength converting particle.
Figure 13B:
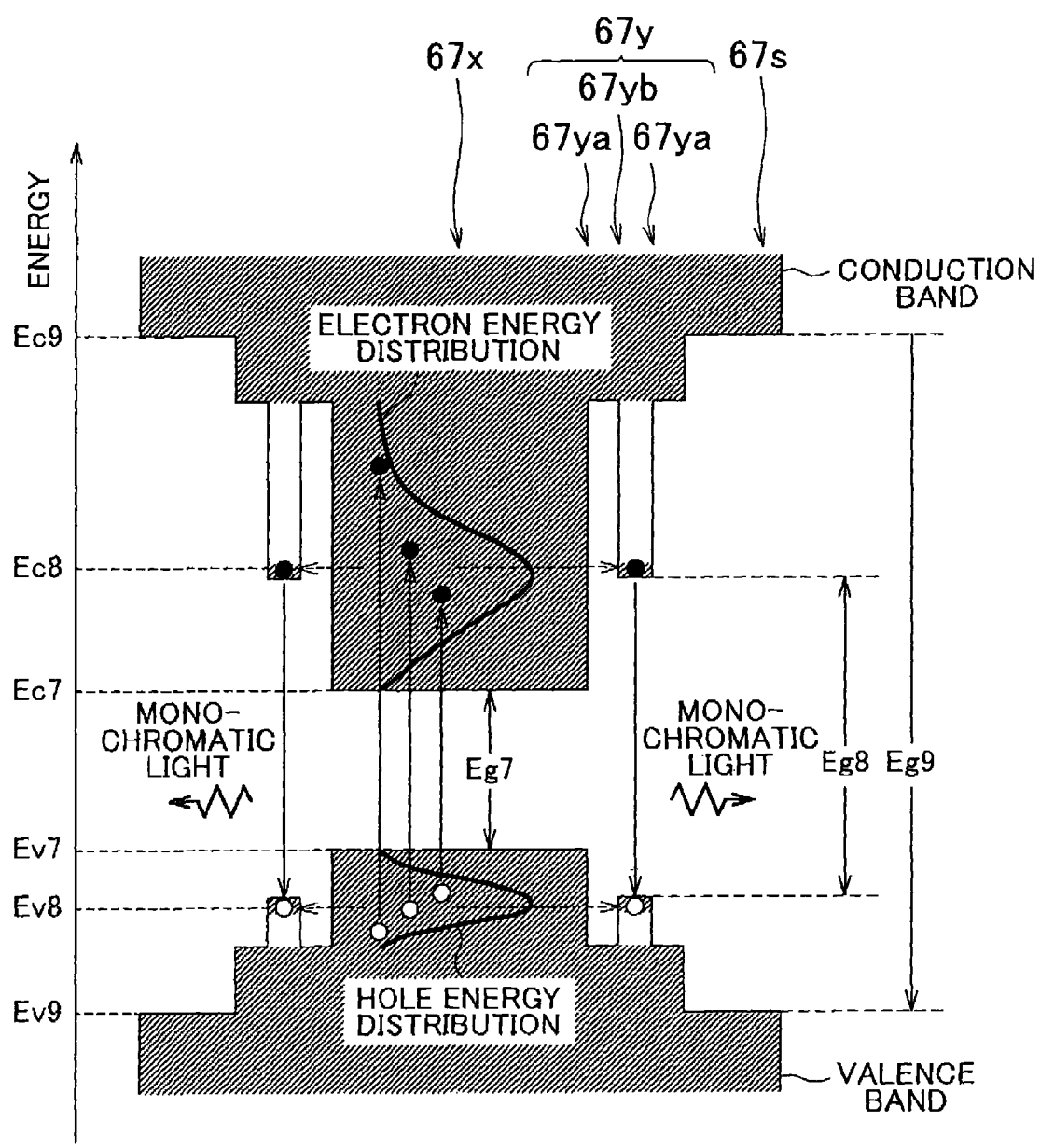
FIG. 13B is a diagram showing a band structure of the wavelength converting particle shown in FIG. 13 A.

FIG. 13A is a sectional view showing an embodiment of a wavelength converting particle 67 having a carrier generating region 67x and a light emitting region 67y that also functions as a carrier selective transfer region. FIG. 13B is a diagram showing the band structure of the wavelength converting particle 67. The wavelength converting region that uses this wavelength converting particle 67 is in a form where, for example, a plurality of the wavelength converting particles 67 are dispersed and held within a transparent material.

The wavelength converting particle 67 has a carrier generating region 67x at the center, and includes, concentrically from the center outward, the carrier generating region 67x, a light emitting region 67y, and an outside material region 67s. The carrier generating region 67x, the light emitting region 67y, and the outside material region 67s are each composed of semiconductor materials. The light emitting region 67y has, disposed concentrically outward from the center side, a barrier layer 67ya, a quantum well layer 67yb, and a barrier layer 67ya. At least the barrier layer 67ya situated on the center side has a thickness such that carriers can move therethrough by tunneling conduction. The barrier layer 67ya situated on the center side is formed on the surface of the carrier generating region 67x, and the quantum well layer 67yb is formed on the surface of this barrier layer 67ya. The barrier layer 67ya situated on the outside is formed on the surface of the quantum well layer 67yb, and the outside material region 67s is formed on the surface of the barrier layer 67ya situated on the outside. In the wavelength converting particle 67, the outside material region 67s is set to a thickness through which carriers cannot pass by tunneling conduction.

As shown in FIG. 13B, the energy gap of the semiconductor material making up the barrier layers 67ya is larger than the energy gap Eg8 of the semiconductor material making up the quantum well layer 67yb, and discrete energy levels owing to quantum confinement effects are formed in the conduction and valence bands for the quantum well layer 67yb. The energy gap Eg8 of the semiconductor material making up the quantum well layer 67yb is larger than the energy gap Eg7 of the semiconductor material making up the carrier generating region 67x, and the energy gap Eg9 of the semiconductor material making up the outside material region 67s is larger than the energy gap of the semiconductor material making up the barrier layers 67ya. The energy gap Eg9 of the semiconductor material making up the outside material region 67s is set to a size that does not absorb the light to be absorbed by the carrier generating region 67x. Here, assuming that Ec7 is the energy at the bottom edge of the conduction band for the semiconductor material making up the carrier generating region 67x, Ev7 is the energy at the top edge of the valence band for the same semiconductor material, Ec8 is the energy of the lowest discrete energy level formed in the conduction band for the semiconductor material making up the quantum well layer 67yb, Ev8 is the energy of the lowest discrete energy level formed in the valence band for the same semiconductor material, Ec9 is the energy at the bottom edge of the conduction band for the semiconductor material making up the outside material region 67s, and Ev9 is the energy at the top edge of the valence band for the same semiconductor material, the wavelength converting particle 67 satisfies the following relationships.

$Eg7 < Eg8 < Eg9$ $Ec7 < Ec8 < Ec9$ $Ev9 < Ev8 < Ev7$

When light falls on the wavelength converting particle 67, the light passes through the outside material region 67s, reaching the carrier generating region 67x. When the light reaches the carrier generating region 67x, that light that has an energy larger than the energy gap Eg7 of the carrier generating region 67x is absorbed, and electrons and holes having various energies are generated in the carrier generating region 67x.

Here, the barrier layer 67ya formed on the surface of the carrier generating region 67x is set to a thickness such that carriers can move to the quantum well layer 67yb by tunneling conduction. Therefore, of the electrons and holes generated in the carrier generating region 67x, those electrons and holes that have energies that correspond to discrete energy levels formed in the conduction band or valence band for the quantum well layer 67yb are able to reach the discrete energy levels of the quantum well layer 67yb via tunneling conduction. On the other hand, since the outside material region 67s is set to a thickness through which carriers cannot pass by tunneling conduction, in the wavelength converting particle 67, those electrons and holes that have moved to the quantum well layer 67yb cannot move to the outside material region 67s side. Therefore, the electrons and holes that have moved to the quantum well layer 67yb combine at the quantum well layer 67yb, becoming monochromatic light having an energy that corresponds to the energy difference between the lowest discrete energy level in the conduction band and the lowest discrete energy level in the valence band for the quantum well layer 67yb. On the other hand, of the electrons generated in the carrier generating region 67x, some of those electrons having energies that differ from the discrete energy levels formed in the conduction band for the quantum well layer 67yb, by carrying out mutual energy transfer with other electrons generated in the carrier generating region 67x, come to have the same energies as discrete energy levels formed in the conduction band for the quantum well layer 67yb. Similarly, of the holes generated in the carrier generating region 67x, some of those holes having energies that differ from discrete energy levels formed in the valence band for the quantum well layer 67yb, by carrying out mutual energy transfer with other holes generated in the carrier generating region 67x, come to have the same energies as discrete energy levels formed in the valence band for the quantum well layer 67yb. The electrons and holes that have come to have the same energies as discrete energy levels formed in the conduction band and valence band for the quantum well layer 67yb are able to reach the discrete energy levels of the quantum well layer 67yb by tunneling conduction and, by combining at the quantum well layer 67yb, become monochromatic light having an energy that corresponds to the energy difference between the lowest discrete energy level in the conduction band and the lowest discrete energy level in the valence band for the quantum well layer 67yb. When such wavelength converting particles 67 are used in the photoelectric conversion device of the invention, monochromatic light can be generated in this way. The monochromatic light generated in this way is absorbed by the photoelectric conversion region provided in the photoelectric conversion device, whereby the monochromatic light is converted into electricity.

With the photoelectric conversion device of the invention including wavelength converting particles 67, it is possible to greatly expand the wavelength range of light utilized during conversion into electricity at the photoelectric conversion region. A purpose of the wavelength converting particle 67 is to allow the carriers that are generated in the carrier generating region 67x to recombine at the light emitting region 67y; it is not intended to extract the generated carriers directly to the exterior. Hence, in the wavelength converting particle 67, unlike in conventional hot carrier solar cells in which a quantum structure is used, there is no need to have the carriers move all the way to the electrodes, so that it is made possible to markedly reduce the energy loss during movement. Moreover, the wavelength converting particles 67 make it possible to shorten the carrier movement path more than in an embodiment in which a carrier generating region, a carrier selective transfer region, and a light emitting region are provided. Hence, by employing an embodiment having a carrier generating region 67x and a light emitting region 67y that also functions as a carrier selective transfer region, it becomes easy to reduce energy loss during carrier movement. In particular, by controlling the size of the carrier generating region 67x and setting the movement length from the generation of the carrier in the carrier generating region 67x until the carriers reach the light emitting region 67y to about 10 nm or less, it becomes easy to significantly reduce the energy loss during movement. In addition, in an embodiment that uses a semiconductor material for the carrier generating region 67x, it is possible to greatly expand the wavelength range of light that can be used for generating carriers as compared to conventional up-conversion solar cells and down-conversion solar cells in which fluorescent materials have been used. Additionally, in photoelectric conversion devices that input to a photoelectric conversion region the monochromatic light generated at a wavelength converting particle 67, the energy of the monochromatic light input to the photoelectric conversion region is fixed. Thus, it is made easy to reduce the energy loss by using for the photoelectric conversion region a semiconductor material having an energy gap corresponding to the energy of the monochromatic light that is to be input. Accordingly, an embodiment having wavelength converting particles 67 can also provide a photoelectric conversion device in which the photoelectric conversion efficiency can be increased. In the photoelectric conversion device of the invention, by increasing the efficiency of the wavelength converting particle 67 that converts light into monochromatic light, it is made easy to increase the photoelectric conversion efficiency.

In this invention, by placing the wavelength converting particles 67 on the upstream side of the photoelectric conversion region in the direction in which light travels, solar cells that use the wavelength converting particles 67 can be rendered into down-conversion solar cells. Alternatively, by placing the wavelength converting particles 67 on the downstream side of the photoelectric conversion region in the direction in which light travels, or within the photoelectric conversion region, solar cells that use the wavelength converting particles 67 can be rendered into up-conversion solar cells. Moreover, in cases where the wavelength converting particles 67 are disposed on the downstream side of the photoelectric conversion region in the direction in which light travels, an embodiment may be employed in which there is provided, in the wavelength converting region having wavelength converting particles 67, a light reflecting region that reflects, to the photoelectric conversion region side, the monochromatic light generated at the wavelength converting particles 67.

In the wavelength converting particles 67, the carrier generating region 67x may be fabricated using materials and processes both similar to those used for the carrier generating region 61x described above. The diameter of the carrier generating region 67x may be similar to that of the carrier generating region 61x. Moreover, the light generating region 67y may be fabricated using materials and processes both similar to those used for the carrier selective transfer region 61y described above. Also, in order to set the total thickness of the outside material region 67s and the barrier layer 67ya to a thickness that does not allow carriers to pass through by tunneling conduction, the thickness of the outside material region 67s may be set to at least 10 nm, and, in order to ensure that the proportion of the volume of the carrier generating region 67x to the whole of the wavelength converting particle 67 does not become too small, the thickness of the outside material region 67s may be set to not more than 100 nm. The semiconductor material making up the outside material region 67s may be, for example, GaAs, CdTe, AlGaAs, GaInP, AlAs, ZnTe, GaP, CdS, ZnSe, GaN or ZnS. The outside material region 67s may be fabricated by a method similar to that used for the light emitting region 61z described above.

In the above explanation of the wavelength converting particle 67, an embodiment has been described in which an outside material region 67s composed of a semiconductor material is provided. However, the invention is not limited to this embodiment. The outside material region may be composed of an available transparent insulating material that does not absorb light. Examples of such insulating materials include $SiO_2$ and $SiN_x$.

In the foregoing explanation concerning a wavelength converting region in a form having a carrier generating region and a light emitting region that also functions as a carrier selective transfer region, an embodiment involving the use of wavelength converting particles 67 has been described by way of illustration. However, the invention is not limited to this embodiment. As in the case of the wavelength converting regions that may be used in the above-described first to third embodiments of the invention, it is also possible to use a linear wavelength converting material (wavelength converting fibers) and a wavelength converting material having a multilayer film structure (wavelength converting film). In cases where wavelength converting fibers are used in an embodiment of the wavelength converting region having a carrier generating region and a light emitting region that also functions as a carrier selective transfer region, the embodiment employed may be one having a carrier generating region that, except being made rod-like, is constructed like the above-described carrier generating region 67x, a light emitting region that, except being made tubular, is constructed like the above-described light-emitting region 67y, and an outside material region that, except being made tubular, is constructed like the above-described outside material region 67s. In such cases, the wavelength converting region that uses wavelength converting fibers may be rendered into a form in which a plurality of wavelength converting fibers are dispersed and held within a transparent material. In cases where a wavelength converting film is used as the wavelength converting region in a form having a carrier generating region and a light emitting region that also functions as a carrier selective transfer region, the embodiment employed may be one having a carrier generating region that, except being film-like, is constructed like the above-described carrier generating region 67x, a light emitting region that, except being film-like, is constructed like the above-described light-emitting region 67y and an outside material region that, except being film-like, is constructed like the above-described outside material region 67s.

Moreover, the wavelength converting region in a form having a carrier generating region and a light emitting region that also functions as a carrier selective transfer region may be dispersed inside a photoelectric conversion region having a bulk heterojunction structure in which p-n junctions are dispersed throughout the entire layer. When such an embodiment is employed, a photoelectric conversion device that uses wavelength converting particles as the wavelength converting region in a form having a carrier generating region and a light emitting region that also functions as a carrier selective transfer region has a cross-section similar to that shown in FIG. 8A. The cross-section of a photoelectric conversion device that uses wavelength converting fibers as the wavelength converting region in a form having a carrier generating region and a light emitting region that also functions as a carrier selective transfer region is similar to that shown in FIG. 8B.

The invention has been described above with reference to what, at the present time, are thought to be practical and preferred embodiments. However, it should be understood that the invention is not limited to the foregoing embodiments described in the specification of the present application, that various modifications and changes may be made thereto without departing from the gist of the invention or inventive ideas as set forth in the appended claims and the entire specification, and that photoelectric conversion devices, in which such modifications and changes are made, are also encompassed within the technical scope of the invention.

The invention claimed is:

1. A photoelectric conversion device comprising:
a wavelength converting region that absorbs ambient light to generate electrons and holes, and recombines the generated electrons and holes to generate monochromatic light; and
a photoelectric conversion region that has a p-n junction or p-i-n junction, absorbs the monochromatic light generated in the wavelength converting region to generate electrons and holes, and separates and moves the electrons and holes generated by absorption of the monochromatic light, wherein
the wavelength converting region includes:
a carrier generating region that generates the electrons and holes;
a light emitting region that generates the monochromatic light; and
a carrier selective transfer region that is disposed between the carrier generating region and the light emitting region and that moves, of the electrons and holes generated in the carrier generating region, an electron and a hole having a specific energy difference therebetween to the light emitting region, and wherein
assuming that Eg1 is an energy gap for a material making up the carrier generating region, Eg2 is an energy gap for a material making up the light emitting region;
and Eg3 is an energy gap for a material making up the carrier selective transfer region in a shape in which the material is incorporated within the wavelength converting region, a following relation is satisfied:

$Eg1<Eg2 \leq Eg3$, wherein the wavelength converting region includes wavelength converting particles each having, in sequence concentrically from a center side outward: the carrier generating region, the carrier selective transfer region, and the light emitting region.

2. The photoelectric conversion device according to claim 1, wherein
the wavelength converting region is disposed on an upstream side of the photoelectric conversion region in a traveling direction of the ambient light.

3. The photoelectric conversion device according to claim 1, wherein
the wavelength converting particles are dispersed and held in a transparent material included in the wavelength converting region, and
the transparent material is at least one of an electrically insulating material and a semiconductor material having a larger energy gap than a material making up the carrier generating region of the wavelength converting particles.

4. The photoelectric conversion device according to claim 1, wherein
the wavelength converting region includes a wavelength converting film having the carrier generating region, the carrier selective transfer region and the light emitting region that are stacked so that the carrier selective transfer region is disposed between the carrier generating region and the light emitting region.

5. The photoelectric conversion device according to claim 1, wherein
the p-n junction has sites where a p-type material and an n-type material are three-dimensionally joined.

6. The photoelectric conversion device according to claim 1, wherein, assuming that
Ec1 and Ev1 are, respectively, a conduction-band minimum, and a valence-band maximum for the material making up the carrier generating region;
Ec2 and Ev2 are, respectively, a conduction-band minimum, and a valence-band maximum for the material making up the light emitting region; and
Ec3 and Ev3 are, respectively, an energy at a lowest discrete energy level in a conduction band, and an energy at a lowest discrete energy level in a valence band for the material making up the carrier selective transfer region in the shape in which the material is incorporated within the wavelength converting region,
following relations are satisfied:

$Ec1<Ec2 \leq Ec3$; and $Ev3 \leq Ev2 \leq Ev1$.

7. The photoelectric conversion device according to claim 1, wherein
a surface of the light emitting region is covered with an insulator or a semiconductor material having a larger energy gap than a material making up the carrier generating region.

8. The photoelectric conversion device according to claim 1, wherein
the light emitting region includes:
a pair of first semiconductor regions composed of a first semiconductor; and
a second semiconductor region that is disposed between the pair of first semiconductor regions, and is composed of a second semiconductor having a smaller energy gap than the first semiconductor.

9. The photoelectric conversion device according to claim 1, wherein
the carrier selective transfer region includes:
a pair of wide-gap semiconductor regions composed of a wide-gap semiconductor; and
a narrow-gap semiconductor region that is disposed between the pair of wide-gap semiconductor regions, and is composed of a narrow-gap semiconductor having a smaller energy gap than the wide-gap semiconductor.

10. A photoelectric conversion device comprising:
a wavelength converting region that absorbs ambient light to generate electrons and holes, and recombines the generated electrons and holes to generate monochromatic light; and
a photoelectric conversion region that has a p-n junction or p-i-n junction, absorbs the monochromatic light generated in the wavelength converting region to generate electrons and holes, and separates and moves the electrons and holes generated by absorption of the monochromatic light, wherein
the wavelength converting region includes:
a carrier generating region that generates the electrons and holes;
a light emitting region that generates the monochromatic light; and a carrier selective transfer region that is disposed between the carrier generating region and the light emitting region and that moves, of the electrons and holes generated in the carrier generating region, an electron and a hole having a specific energy difference therebetween to the light emitting region, and wherein assuming that Eg1 is an energy gap for a material making up the carrier generating region, Eg2 is an energy gap for a material making up the light emitting region; and Eg3 is an energy gap for a material making up the carrier selective transfer region in a shape in which the material is incorporated within the wavelength converting region, a following relation is satisfied:

$Eg1 < Eg2 \leq Eg3$, wherein the wavelength converting region includes wavelength converting fibers each having, in sequence concentrically from a center side outward: the carrier generating region, the carrier selective transfer region, and the light emitting region.

11. The photoelectric conversion device according to claim 10, wherein the wavelength converting fibers are dispersed and held in a transparent material included in the wavelength converting region, and the transparent material is at least one of an electrically insulating material and a semiconductor material having a larger energy gap than a material making up the carrier generating region of the wavelength converting fibers.

\* \* \* \* \*